United States Patent
Nikam et al.

(10) Patent No.: US 6,794,402 B2
(45) Date of Patent: Sep. 21, 2004

(54) BICYCLIC CYCLOHEXYLAMINES AND THEIR USE AS NMDA RECEPTOR ANTAGONISTS

(75) Inventors: Sham Shridhar Nikam, Ann Arbor, MI (US); Ian Leslie Scott, Delanson, NY (US); Brian Alan Sherer, Ballston Spa, NY (US); Lawrence David Wise, Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 10/276,054

(22) PCT Filed: May 8, 2001

(86) PCT No.: PCT/US01/14763

§ 371 (c)(1),
(2), (4) Date: Nov. 12, 2002

(87) PCT Pub. No.: WO01/92239

PCT Pub. Date: Dec. 6, 2001

(65) Prior Publication Data

US 2003/0236252 A1 Dec. 25, 2003

Related U.S. Application Data

(60) Provisional application No. 60/208,241, filed on May 31, 2000.

(51) Int. Cl.$^7$ .................. A61K 31/423; C07D 263/58

(52) U.S. Cl. ........................................ 514/375; 548/221
(58) Field of Search ........................... 548/221; 514/375

(56) References Cited

FOREIGN PATENT DOCUMENTS

| | | |
|---|---|---|
| DE | 4438055 | 5/1996 |
| EP | 0982026 | 3/2000 |
| WO | 9948891 | 9/1999 |

*Primary Examiner*—Laura L. Stockton
(74) *Attorney, Agent, or Firm*—David R. Kurlandsky; Charles W. Ashbrook; Mehdi Ganjeizadeh

(57) ABSTRACT

Described are bicycle-substituted cyclohexylamines of Formula I and their pharmaceutically acceptable salts thereof:

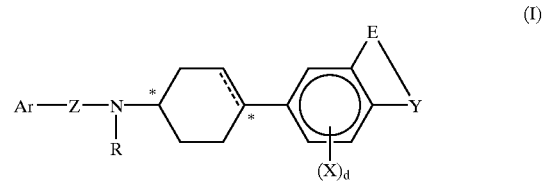

The compounds are antagonists of NMDA receptor channel complexes useful for treating cerebral vascular disorders such as, for example, cerebral ischemia, cardiac arrest, stroke, and Parkinson's disease. The substituents are defined in the specification.

12 Claims, No Drawings

BICYCLIC CYCLOHEXYLAMINES AND THEIR USE AS NMDA RECEPTOR ANTAGONISTS

This application claims the benefit of PCT/US01/14763 filed May 8, 2001, which claims the benefit of U.S. Provisional Application No. 60/208,241 filed May 31, 2000; the entire contents of each of which are hereby incorporated herein by reference.

FIELD OF THE INVENTION

The invention pertains to bicycle-substituted cyclohexylamine derivatives as N-Methyl-D-Aspartate Antagonists (NMDA).

BACKGROUND OF THE INVENTION

Over excitation of NMDA receptor channel complexes on postsynaptic neurons following excessive release of glutamic acid from synaptosomes and glutamic acid from synaptosomes and glial cells results in excessive calcium ion influx into the neuronal cells, which leads to their death. This is believed to occur under ischemic or hypoxic conditions such as stroke, hypoglycemic, cardiac arrest and physical trauma. An NMDA receptor antagonist might be therapeutically useful because it may minimize damage of the central nervous system induced by ischemic or hypoxic conditions. The NMDA receptor channel complex consists of at least three binding domains including a glutamic acid (or NMDA) recognition site, a channel blocking binding site, and a strychnine-insensitive glycine binding type. Physiologically, a blockade of at least one of these sites terminates the channel opening of the NMDA receptor to prevent a calcium ion influx. (Nagata R., et al., *J. Med. Chem.*, 1994;37:3956–3968)

Excessive excitation of NMDA receptor channel complexes by neurotransmitters may be responsible for the loss of neurons in cerebral vascular disorders such as cerebral ischemia or cerebral infarction resulting in a range of conditions such as thromboembolic or hemorrhagic stroke, cerebral vasospasm, hypoglycemia, cardiac arrest, status epilepticus, perinatal asphyxia, anoxia, such as from near drowning, pulmonary surgery and cerebral trauma, as well as lathyrism, Alzheimer's disease, and Huntington's disease. Such conditions likewise suggest the use of agents that may act as antagonists in the receptors identified above may lead to treatment of amyotrophic lateral sclerosis (ALS), schizophrenia, Parkinsonism, epilepsy, anxiety, pain, and drug addiction. (PCT/EPO 94/01492 having publication number WO 94/26747 published Nov. 24, 1994, Watjen et al.)

L-glutamic acid, L-aspartic acid, and a number of other closely related amino acids have the ability to activate neurons in the nervous system, and therefore the vast majority of excitatory neurons in the mammalian CNS. Interaction with glutamic acid mediated neurotransmission is considered a useful approach in the treatment of neurological and psychiatric diseases. (WO 94/26746, published Nov. 24, 1994, Jacobsen et al.)

Excitatory amino acid receptor antagonists that block NMDA receptors are recognized for usefulness in the treatment of a variety of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's disease (Klockgether T., Turski L., *Ann. Neurol.*, 1993;34:585–59), human immunodeficiency virus (HIV) related neuronal injury, amyotrophic lateral sclerosis (ALS), Alzheimer's disease (Francis P. T., Sims N. R, Procter A. W., Bowen D. M., *J. Neurochem.*, 1993;60(5);1589–1604), and Huntington's disease (see Lipton S., *TINS*, 1993;16(12):527–532; Lipton S. A., Rosenberg P. A., *New Eng. J. Med.*, 1994;330 (9):613–622; and Bigge C. F., *Biochem. Pharmacol.*, 1993;45: 1547–1561 and references cited therein). NMDA receptor antagonists may also be used to prevent tolerance to opiate analgesia or to help control withdrawal symptoms from addictive drugs (European Patent Application 488, 959A).

Many of the properties of native NMDA receptors are seen in recombinant homomeric NR1 receptors. These properties are altered by the NR2 subunits. Recombinant NMDA receptors expressed in Xenopus Oocytes have been studied by voltage-clamp recording, and have been found to exhibit developmental and regional expression of the mRNAs encoding NMDA receptor subunits. Electrophysiological assays were utilized to characterize the actions of compounds at NMDA receptors expressed in Xenopus Oocytes. The compounds were assayed at four subunit combinations at cloned rat NMDA receptors, corresponding to three putative NMDA receptor subtypes (Moriyoshi et al., *Nature*, 1991;354:31–37; Monyer et al., *Science*, 1992;256:1217–1221; Kutsuwada et al., *Nature*, 1992:358;36–41; Sugihara et al., *Biochem. Biophys Res. Commun.*, 1992;185:826–832).

Expression cloning of the first NMDA receptor subunit, NMDAR1 (NR1) in Nakanishi's lab in 1991 provided an initial view of the molecular structure of the NMDA receptor (Moriyoshi et al., supra, 1991). There are several other structurally related subunits (NMDAR2A through NMDAR2D) that join NR1 in heteromeric assemblies to form the functional ion channel complex of the receptor (*Annu. Rev. Neurosci.*, 1994;17:31–108). The molecular heterogeneity of NMDA receptors implies a future potential for agents with subtype selective pharmacology.

SUMMARY OF THE INVENTION

Described are bicycle-substituted cyclohexyl amines of Formula I and their pharmaceutically acceptable salts thereof

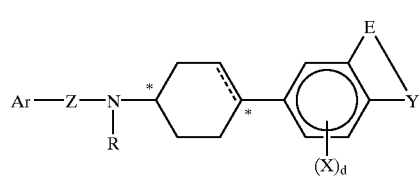

wherein:

Ar is substituted 1 to 3 times or unsubstituted aryl or substituted 1 to 3 times or unsubstituted heteroaryl, which heteroaryl is from 5 to 14 atoms having from 1 to 2 heteroatoms selected from N, O, and S wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$;

Z is 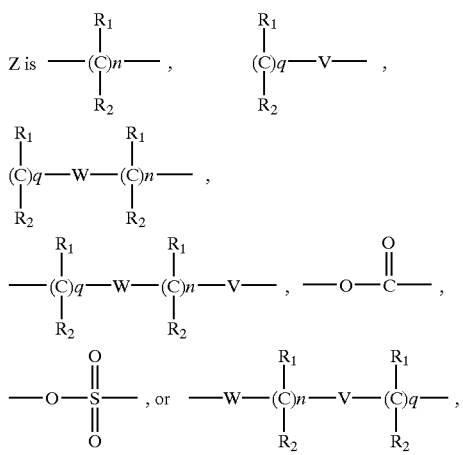

wherein V is —(CH$_2$)$_n$—,

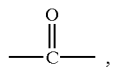,

—S(O)—, or —S(O)$_2$—,
W is —(CH$_2$)$_n$—,

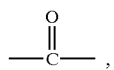,

—S(O)—, —S(O)$_2$—, —O—, —S—, —C≡C—, or entgegen or zusammen —CH(R$_1$)=CH(R$_2$)—,
d is an integer from 0 to 2;
n is an integer from 1 to 6;
q is an integer from 0 to 6;
R$_1$ and R$_2$ are independently selected from the group consisting of hydrogen, alkyl, OH, hydroxyalkyl, aminoalkyl, aralkyl, or N(R$_4$)(R$_5$) wherein R$_4$ and R$_5$ are independently selected from hydrogen, alkyl, aralkyl, heteroaryl, heteroaralkyl, aminoalkyl, hydroxyalkyl, and thioalkyl;
R is hydrogen, alkyl, C(O)R$_6$, C(O)OR$_6$, C(O)NHR$_6$, -alkyl-C(O)NH$_2$, aralkyl, (C$_3$–C$_7$ cycloalkyl)-alkyl, hydroxyalkyl, aminoalkyl, amino(hydroxy)alkyl, carboxyalkyl, heteroaralkyl, alkenylalkyl, or OH wherein R$_6$ is alkyl or aralkyl;
X is independently selected from hydrogen or an electron withdrawing group; and
E—Y— is
 —CH=CH—N(H)—,
 —(CH$_2$)$_2$—N(H)—,
 —CH=N—N(H)—,
 —C(O)—CH$_2$—N(H)—,
 —CH$_2$—C(O)—N(H)—,
 —CH$_2$—S(O)—N(H)—,
 —CH$_2$—S(O)$_2$—N(H)—,
 —CH=CH—CH(OH)—,
 —(CH$_2$)$_2$—CH(OH)—,
 —C(O)—CH$_2$—C(O)—,
 —C(O)—NH—C(O)—,
 —N=CH—N(H)—,
 —N(H)—C(O)—N(H)—,
 —O—C(O)—NH—,
 —S—C(O)—NH—,
 —O—N=CH(OH)—,
 —S—N=CH(OH)—,
 —N=N—N(H)—,
 —CH=CH—CH=C(OH)—,
 —(CH$_2$)$_3$—CH(OH)—,
 —(CH$_2$)$_2$—S(O)—N(H)—,
 —(CH$_2$)$_2$—S(O)$_2$—N(H)—,
 —CH=CH—C(O)—N(H)—,
 —C(O)—NH—N=C(OH)—,
 —CH=N—NH—C(O),
 —CH=N(O)—N=C(OH)—,
 —N(H)—C(O)—N(H)—C(O)—,
 —N=CH—C(O)—NH—,
 —O—CH$_2$—C(O)—NH—,
 —S—CH$_2$—C(O)—NH—, or
 —N(H)—C(O)—C(O)—N(H)—;
- - - denotes a single or double bond; and
* denotes cis or trans or a mixture thereof.

The invention also relates to compounds of Formula II

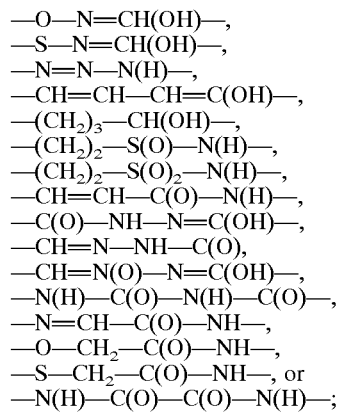

or a pharmaceutically acceptable salt thereof wherein:
Ar, R, X, d, and —E—Y— are as defined above;

T is 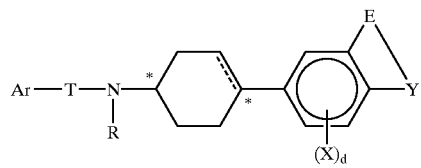 or

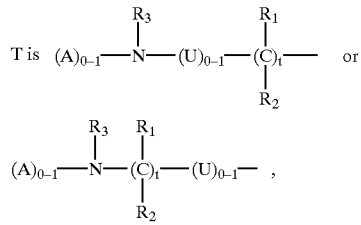, wherein U is —CH$_2$—,

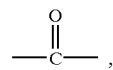,

—S(O)—, or —S(O)$_2$—,
A is —CH$_2$,

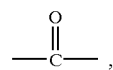,

—S(O)—, or —S(O)$_2$—,
t is an integer from 1 to 3,
R$_1$ and R$_2$ are independently selected from hydrogen, alkyl, OH, hydroxyalkyl, aminoalkyl, thioalkyl, aryl, aralkyl, heteroaryl, heteroaralkyl, guanidinyl, (aminocarbonyl)alkyl-, carboxyalkyl-, (methylthio)-alkyl-, or N(R$_4$)(R$_5$), wherein R$_4$ and R$_5$ are independently selected from hydrogen, alkyl, aralkyl, heteroaryl, heteroaralkyl, ureidoalkyl, aminoalkyl, hydroxyalkyl, or thioalkyl;
R$_3$ is hydrogen, alkyl, OH, or aralkyl;
R is hydrogen, alkyl, C(O)R$_6$, C(O)OR$_6$, C(O)NHR$_6$, alkyl —CO$_2$NH$_2$, aralkyl, hydroxyalkyl, (C$_3$–C$_7$ cycloalkyl) alkyl, aminoalkyl, amino(hydroxy)alkyl, carboxyalkyl, heteroaralkyl, alkenyl-alkyl, or OH wherein $R_6$ is alkyl or aralkyl;

X is independently selected from hydrogen or an electron withdrawing group; and

* denotes cis or trans or a mixture thereof

The invention also relates to compounds of Formula III:

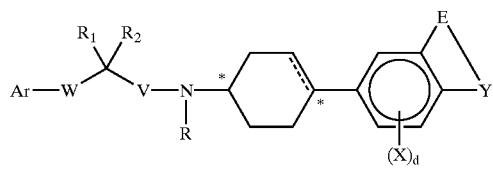

wherein the substituents are defined above.

The invention is also concerned with a pharmaceutical composition useful for treating disorders responsive to the selective blockade of N-methyl-D-aspartate receptor subtypes utilizing the compounds of Formula I or Formula II or Formula III and the pharmaceutically acceptable salts thereof, optionally disorders as stroke, cerebral ischemia, trauma, hypoglycemia, neurodegenerative disorders, anxiety, depression, migraine headache, convulsions, aminoglycoside antibiotics-induced hearing loss, psychosis, glaucoma, CMV retinitis, opioid tolerance or withdrawal, chronic pain, or urinary incontinence.

The invention is also concerned with a method of treating disorders responsive to the selective blockade of the N-methyl-D-aspartate receptor subtypes in a mammal suffering thereof which comprises administering in unit dosage form, at least one compound represented by Formula I or Formula II or Formula III above or its pharmaceutically acceptable salts thereof.

DETAILED DESCRIPTION OF THE INVENTION

The invention is concerned with bicycle-substituted cyclohexylamines of Formula I and their pharmaceutically acceptable salts thereof:

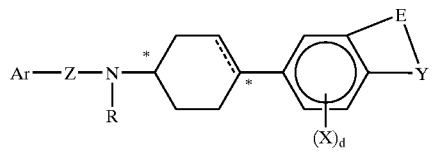

wherein:

Ar is substituted 1 to 3 times or unsubstituted aryl or substituted 1 to 3 times or unsubstituted heteroaryl, which heteroaryl is from 5 to 14 atoms having from 1 to 2 heteroatoms selected from N, O, and S wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$;

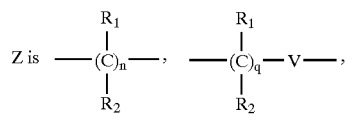

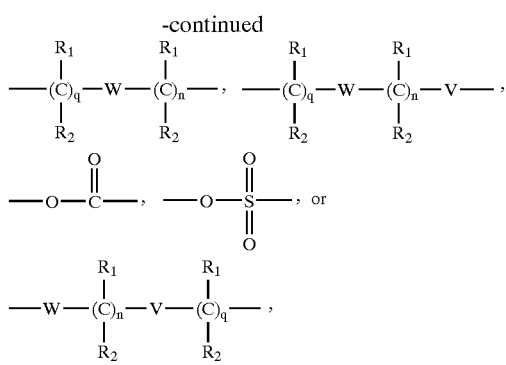

wherein V is —$(CH_2)_n$—,

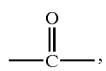

—S(O)—, or —S(O)$_2$—,

W is —$(CH_2)_n$—,

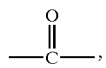

—S(O)—, —S(O)$_2$—, —O—, —S—, —C≡C—, or entgegen or zusammen —CH($R_1$)=CH($R_2$)—, d is an integer from 0 to 2;
n is an integer from 1 to 6;
q is an integer from 0 to 6;
$R_1$ and $R_2$ are independently selected from the group consisting of hydrogen, alkyl, OH, hydroxyalkyl, aminoalkyl, aralkyl, or N($R_4$)($R_5$) wherein $R_4$ and $R_5$ are independently selected from hydrogen, alkyl, aralkyl, heteroaryl, heteroaralkyl, aminoalkyl, hydroxyalkyl, and thioalkyl;
R is hydrogen, alkyl, C(O)$R_6$, C(O)O$R_6$, C(O)NH$_6$, -alkyl-C(O)NH$_2$, aralkyl, ($C_3$–$C_7$ cycloalkyl)-alkyl, hydroxyalkyl, aminoalkyl, amino(hydroxy)alkyl, carboxyalkyl, heteroaralkyl, alkenylalkyl, or OH wherein $R_6$ is alkyl or aralkyl;
X is independently selected from hydrogen or an electron withdrawing group; and
—E—Y— is
—CH=CH—N(H)—,
—(CH$_2$)$_2$—N(H)—,
—CH=N—N(H)—,
—C(O)—CH$_2$—N(H)—,
—CH$_2$—C(O)—N(H)—,
—CH$_2$—S(O)—N(H)—,
—CH$_2$—S(O)$_2$—N(H)—,
—CH=CH—CH(OH)—,
—(CH$_2$)$_2$—CH(OH)—,
—C(O)—CH$_2$—C(O)—,
—C(O)—NH—C(O)—,
—N=CH—N(H)—,
—N(H)—C(O)—N(H)—,
—O—C(O)—NH—,
—S—C(O)—NH—,
—O—N=CH(OH)—,
—S—N=CH(OH)—,
—N=N—N(H)—,
—CH=CH—CH=C(OH)—, —(CH₂)₃—CH(OH)—,
—(CH₂)₂—S(O)—N(H)—,
—(CH₂)₂—S(O)₂—N(H)—,
—CH=CH—C(O)—N(H)—,
—C(O)—NH—N=C(OH)—,
—CH=N—NH—C(O),
—CH=N(O)—N=C(OH)—,
—N(H)—C(O)—N(H)—C(O)—,
—N=CH—C(O)—NH—,
—O—CH₂—C(O)—NH—,
—S—CH₂—C(O)—NH—, or
—N(H)—C(O)—C(O)—N(H)—; and

* denotes cis or trans or a mixture thereof.

In the compounds of the present invention preferred are compounds of Formula I or pharmaceutically acceptable salts thereof wherein:

X is independently selected from hydrogen or an electron withdrawing group selected from the group consisting of halogen, nitro, cyano, aminoalkyl, CF₃, C(O)CH₃, and haloalkyl.

More preferred are compounds of Formula I or pharmaceutically acceptable salts thereof wherein:

Ar is unsubstituted or substituted phenyl;

X is independently selected from hydrogen or an electron withdrawing group selected from the group consisting of halogen, nitro, cyano, aminoalkyl, CF₃, C(O)CH₃, and haloalkyl; and —E—Y— is selected from

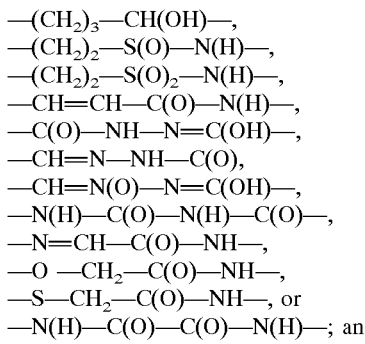

—CH=CH—NH—, —N=CH—NH—;

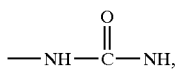

—N=N—NH—, and

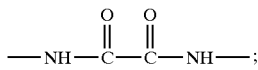

* denotes trans.

Still more preferred are compounds of Formula I or pharmaceutically acceptable salts thereof wherein:

Ar is unsubstituted or substituted phenyl;

R is hydrogen, methyl, heteroaralkyl, (C₃–C₇ cycloalkyl) alkyl, alkenylalkyl, H₂NC(O)alkyl, or C(O)CH₃;

Z is —CH₂—(CH₂)ₘ—,

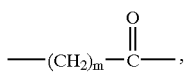

—O—(CH₂)ₘ—,

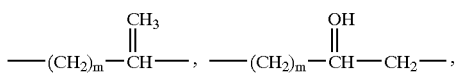

—S—(CH₂)ₘ—, —C≡C—CH₂, or —C≡C—(CH₂)₂—
wherein m is an integer 2 or 3;

—E—Y— is selected from

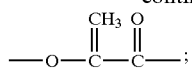

—CH=CH—NH—, —N=CH—NH—;

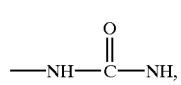

—N=N—NH—, and

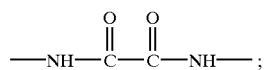

X is hydrogen; and

* denotes trans.

Most preferred are compounds of Formula I selected from those listed below:

6-[trans-4-(3-Phenylpropylamino)cyclohexyl]-3H-benzoxazol-2-one;

6-{trans-4-[2-(4-Fluorophenoxy)ethylamino]cyclohexyl}-3H-benzoxazol-2-one;

6-[trans-4-(2-Phenoxyethylamino)cyclohexyl]-3H-benzoxazol-2-one;

6-{trans-4-[3-(4-Fluorophenyl)propylamino]cyclohexyl}-3H-benzoxazol-2-one;

6-{cis-4-[3-(4-Fluorophenyl)propylamino]cyclohexyl}-3H-benzoxazol-2-one;

6-[trans-4-(2-Phenylsulfanylethylamino)cyclohexyl]-3H-benzoxazol-2-one;

6-[cis-4-(2-Phenylsulfanylethylamino)cyclohexyl]-3H-benzoxazol-2-one;

6-[4-(3-Phenylpropylamino)cyclohexyl-1-enyl]-3H-benzoxazol-2-one;

6-{trans-4-[2-(4-Fluorophenylsulfanyl)ethylamino]cyclohexyl}-3H-benzoxazol-2-one;

6-{trans-4-[(R)-1-Methyl-3-phenylpropylamino]cyclohexyl}-3H-benzoxazol-2-one;

6-{trans-4-[(S)-1-Methyl-3-phenylpropylamino]cyclohexyl}-3H-benzoxazol-2-one;

6-{trans-4-[(1S,2S)-2-Hydroxy-2-(4-methoxyphenyl)-1-methylethylamino]cyclohexyl}-3H-benzoxazol-2-one;

6-{cis-4-[(1S,2S)-2-Hydroxy-2-(4-methoxyphenyl)-1-methylethylamino]-cyclohexyl}-3H-benzoxazol-2-one;

6-{trans-4-[(1S,2R)-2-Hydroxy-1-methyl-2-phenylethylamino]-cyclohexyl}-3H-benzoxazol-2-one;

6-[cis-4-(3-p-Tolylpropylamino)cyclohexyl]-3H-benzoxazol-2-one;

6-[trans-4-(3-p-Tolylpropylamino)cyclohexyl]-3H-benzoxazol-2-one;

6-[trans-4-(2-Benzenesulfinylethylamino)cyclohexyl]-3H-benzoxazol-2-one;
6-[trans-4-(2-Benzenesulfonylethylamino)cyclohexyl]-3H-benzoxazol-2-one;
6-{trans-4-[Methyl(3-phenylpropyl)amino]cyclohexyl}-3H-benzoxazol-2-one;
6-(trans-4-{[3-(4-Fluorophenyl)propyl]methylamino}cyclohexyl)-3H-benzoxazol-2-one;
6-(cis-4-{[3-(4-Fluorophenyl)propyl]methylamino}cyclohexyl)-3H-benzoxazol-2-one;
6-{trans-[4-(2-Methyl-3-phenylpropylamino)cyclohexyl]}-3H-benzoxazol-2-one
6-{trans-4-[Methyl(2-methyl-3-phenylpropyl)amino]cyclohexyl}-3H-benzoxazol-2-one;
6-{trans-[4-(3-Phenyl-prop-2-ylamino]cyclohexyl]}-3H-benzoxazol-2-one;
6-{trans-4-[Methyl(3-phenyl-prop-2-enyl)amino)cyclohexyl}-3H-benzoxazol-2-one;
6-{trans-4-[2-(4-Fluorophenylsulfanylethyl)methylamino]cyclohexyl}-3H-benzoxazol-2-one;
6-{trans-4-[3-(4-Trifluoromethylphenyl)propylamino]cyclohexyl}-3H-benzoxazol-2-one;
6-{trans-4-[Methyl-3-(p-tolylpropyl)amino]cyclohexyl}-3H-benzoxazol-2-one;
6-{trans-4-[Methyl(2-phenoxyethyl)amino]cyclohexyl}-3H-benzoxazol-2-one;
6-{trans-4-[Methyl-3-(4-trifluoromethylphenyl)propylamino]cyclohexyl}-3H-benzoxazol-2-one;
6-{trans-4-[3-(2,4-Difluorophenyl)propylamino]cyclohexyl}-3H-benzoxazol-2-one;
6-(trans-4-{[3-(2,4-Difluorophenyl)propyl]methylamino}cyclohexyl)-3H-benzoxazol-2-one;
6-(trans-4-{[3-(4-Isopropylphenyl)propyl]methylamino}cyclohexyl)-3H-benzoxazol-2-one;
6-(trans-4-{[3-(4-Isobutylphenyl)propyl]methylamino}cyclohexyl)-3H-benzoxazol-2-one;
6-(trans-4-{[Ethyl-[3-(4-fluorophenyl)propyl]amino}cyclohexyl)-3H-benzoxazol-2-one;
6-(trans-4-{Ethyl-[3-(4-trifluoromethylphenyl)propyl]amino}cyclohexyl)-3H-benzoxazol-2-one;
6-(trans-4-{Ethyl-[(R)-1-methyl-3-phenylpropyl]amino}cyclohexyl)-3H-benzoxazol-2-one;
6-(trans-4-{Ethyl-[(S)-1-methyl-3-phenylpropyl]amino}cyclohexyl)-3H-benzoxazol-2-one;
6-{trans-4-[[3-(4-Fluorophenyl)propyl]-(2-hydroxyethyl)amino]-cyclohexyl}-3H-benzoxazol-2-one;
6-(trans-4-{Cyclopropylmethyl-[3-(4-fluorophenyl)propyl]-amino}cyclohexyl)-3H-benzoxazol-2-one;
6-(trans-4-{[3-(4-Fluorophenyl)propyl]furan-3-ylmethylamino}-cyclohexyl)-3H-benzoxazol-2-one;
6-(trans-4-{Allyl-[3-(4-Fluorophenyl)propyl]amino}cyclohexyl)-3H-benzoxazol-2-one;
6-(trans-4-{[3-(4-Fluorophenyl)propyl]isobutylamino}cyclohexyl)-3H-benzoxazol-2-one;
6-(trans-4-{(2-Aminoethyl)-[3-(4-fluorophenyl)propyl]amino}-cyclohexyl)-3H-benzoxazol-2-one;
2-{[3-(4-Fluorophenyl)propyl]-[4-(2-oxo-2,3-dihydrobenzoxazol-6-yl)-cyclohexyl]amino}acetamide;
(S)-6-{trans-4-[1-(4-Fluorophenylsulfanyl)pentan-2-ylamino]cyclohexyl}-3H-benzoxazol-2-one;
(S)-6-{trans-4-[Ethyl(1-(4-fluorophenylsulfanyl)pentan-2-yl)amino]cyclohexyl}-3H-benzoxazol-2-one;

6-[trans-4-(3-Phenylbutylamino)cyclohexyl]-3H-benzoxazol-2-one;
6-[trans-4-(Methyl-3-phenylbutylamino)cyclohexyl]-3H-benzoxazol-2-one;
6-{trans-4-[3-(4-Chlorophenyl)propylamino]cyclohexyl}-3H-benzoxazol-2-one;
6-(trans-4-{[3-(4-Chlorophenyl)propyl]methylamino}cyclohexyl)-3H-benzoxazol-2-one;
6-(trans-4-{[3-(2,4-Dichlorophenyl)propyl]methylamino}cyclohexyl)-3H-benzoxazol-2-one;
6-(trans-4-[3-(3,5-Difluorophenyl)propylamino]cyclohexyl}-3H-benzoxazol-2-one;
6-(trans-4-{[3-(3,5-Difluorophenyl)propyl]methylamino}cyclohexyl)-3H-benzoxazol-2-one;
6-(trans-4-[3-(3,4-Difluorophenyl)propylamino]cyclohexyl}-3H-benzoxazol-2-one;
6-(trans-4-{[3-(3,4-Difluorophenyl)propyl]methylamino}cyclohexyl)-3H-benzoxazol-2-one;
6-(trans-4-{[3-(2,3,4-Trifluorophenyl)propyl]methylamino}cyclohexyl)-3H-benzoxazol-2-one;
6-(4-{[3-(trans-4-Dimethylaminophenyl)propyl]methylamino}-cyclohexyl)-3H-benzoxazol-2-one;
6-(trans-4-{[3-(2,4,6-Trifluorophenyl)propyl]methylamino}cyclohexyl)-3H-benzoxazol-2-one;
6-(trans-4-[3-(2,4-Dimethylphenyl)propylamino]cyclohexyl}-3H-benzoxazol-2-one;
6-(trans-{4-[Methyl(2,4-dimethylphenylpropyl)amino]cyclohexyl})-3H-benzoxazol-2-one;
6-{trans-4-[3-(2-Chloro-4-fluorophenyl)propylamino]cyclohexyl}-3H-benzoxazol-2-one;
6-(trans-4-{[3-(2-Chloro-4-fluorophenyl)propyl]methylamino}-cyclohexyl)-3H-benzoxazol-2-one;
6-{trans-4-[3-(4-Chloro-2-fluorophenyl)propylamino]cyclohexyl}-3H-benzoxazol-2-one;
6-(trans-4-{[3-(4-Chloro-2-fluorophenyl)propyl]methylamino}-cyclohexyl)-3H-benzoxazol-2-one;
6-(trans-4-[3-(4-Fluoro-2-methylphenyl)propylamino]cyclohexyl}-3H-benzoxazol-2-one;
6-(trans-{4-[Methyl(4-fluoro-2-methylphenylpropyl)amino]cyclohexyl})-3H-benzoxazol-2-one;
6-{trans-4-[3-(3-Fluoro-2-methylphenyl)propylamino]cyclohexyl}-3H-benzoxazol-2-one;
6-(trans-4-{[3-(3-Fluoro-2-methylphenyl)propyl]methylamino}-cyclohexyl)-3H-benzoxazol-2-one;
6-{trans-4-[3-(2-Fluorophenyl)propylamino]cyclohexyl}-3H-benzoxazol-2-one;
6-(trans-4-{[3-(2-Fluorophenyl)propyl]methylamino}cyclohexyl)-3H-benzoxazol-2-one;
6-{trans-4-[3-(3-Fluorophenyl)propylamino]cyclohexyl}-3H-benzoxazol-2-one;
6-(trans-4-{[3-(3-Fluorophenyl)propyl]methylamino}cyclohexyl)-3H-benzoxazol-2-one;
6-{trans-4-[(3-Cyclohexylpropyl)amino]cyclohexyl}-3H-benzoxazol-2-one;
6-{trans-4-[(3-Cyclohexylpropyl)methylamino]cyclohexyl}-3H-benzoxazol-2-one;
6-{trans-4-[4-(3-Thiophen-3-yl)propylamino]cyclohexyl}-3H-benzoxazol-2-one;
6-[trans-4-{[3-(3-Thiophen-3-yl)propyl]methylamino}cyclohexyl)-3H-benzoxazol-2-one;
6-{trans-4-[Methyl(3-thiazol-2-ylpropyl)amino]cyclohexyl}-3H-benzoxazol-2-one;

6-(trans-4-{Methyl-[2-(methylphenylamino)ethyl]amino}cyclohexyl)-3H-benzoxazol-2-one;

N-(2-{Methyl-[4-(2-oxo-2,3-dihydrobenzoxazol-6-yl)cyclohexyl]amino}-ethyl)benzamide;

N-{2-[4-(2-Oxo-2,3-dihydrobenzoxazol-6-yl)cyclohexylamino]-ethyl}benzamide;

6-{trans-4-[3-(4-Fluorophenyl)propylamino]cyclohexyl}-3H-benzoxazol-2-one;

3-(4-Fluorophenyl)-N-methyl-N-[trans-4-(2-oxo-2,3-dihydrobenzoxazol-6-yl)cyclohexyl]propionamide;

6-(trans-4-{[3-(4-Fluorophenyl)propyl]methylamino}cyclohexyl)-3H-benzoxazol-2-one;

5-{trans-4-[3-(4-Fluorophenyl)propylamino]cyclohexyl}-1,3-dihydrobenzoimidazol-2-one;

5-(trans-4-{[3-(4-Fluorophenyl)propyl]methylamino}cyclohexyl)-1,3-dihydrobenzoimidazol-2-one;

6-(4-{[3-(4-Fluorophenyl)propyl]methylamino}cyclohexyl)-5-methyl-3H-benzoxazol-2-one; and 6-(trans-4-{[3-(4-Fluorophenyl)propyl]methylamino}cyclohexyl)-5-methoxy-3H-benzoxazol-2-one.

Preferred are compounds of Formula II or pharmaceutically acceptable salts thereof wherein:

X is independently selected from hydrogen or an electron withdrawing group selected from the group consisting of halogen, nitro, cyano, aminoalkyl, $CF_3$, $C(O)CH_3$, and haloalkyl.

More preferred are compounds of Formula II or pharmaceutically acceptable salts thereof wherein:

Ar is unsubstituted or substituted phenyl;

X is independently selected from hydrogen or an electron withdrawing group selected from the group consisting of halogen, nitro, cyano, aminoalkyl, $CF_3$, $C(O)CH_3$, and haloalkyl; and —E—Y— is selected from

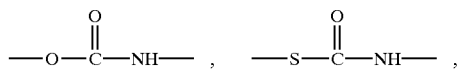

—CH=CH—NH—, —N=CH—NH—;

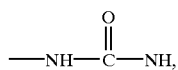

—N=N—NH—, and

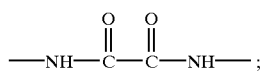

and

* denotes trans.

Still more preferred are compounds of Formula II or pharmaceutically acceptable salts thereof wherein:

Ar is unsubstituted or substituted phenyl;

Ar and the nitrogen atom bearing R are separated by 3 or 4 atoms;

X is independently selected from hydrogen or an electron withdrawing group selected from the group consisting of halogen, nitro, cyano, $CF_3$, $C(O)CH_3$, and haloalkyl;

—E—Y— is selected from

—CH=CH—NH—, —N=CH—NH—;

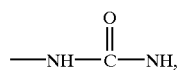

—N=N—NH—, and

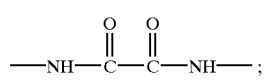

and

* denotes trans.

Still more preferred are compounds of Formula II or pharmaceutically acceptable salts thereof wherein:

Ar is unsubstituted or substituted phenyl;

T is

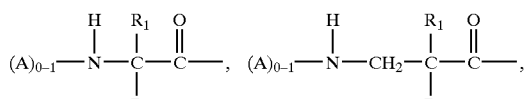

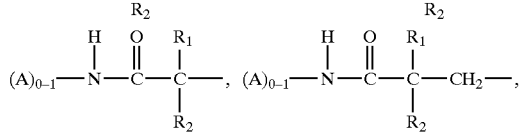

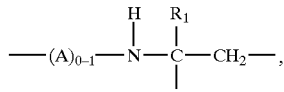

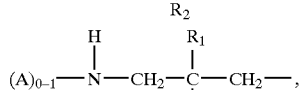

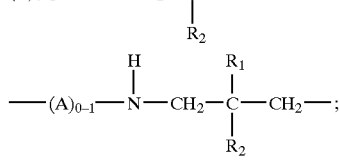

R is hydrogen or methyl or heteroaralkyl or ($C_3$–$C_7$ cycloalkyl)alkyl; $H_2NC(O)$alkyl, alkenylalkyl, or $C(O)CH_3$;

X is hydrogen; and

—E—Y— is selected from

—CH=CH—NH—, —N=CH—NH—;

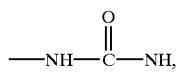

—N=N—NH—, and

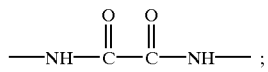

and
* denotes trans.
Preferred compounds of Formula II are:
6-[trans-4-(2-Phenylaminoethylamino)cyclohexyl]-3H-benzoxazol-2-one; and
N-(2-{Methyl[4-(2-oxo-2,3-dihydrobenzoxazol-6-yl)cyclohexyl]amino}-ethyl)benzamide.
Another preferred compound is that of Formula III

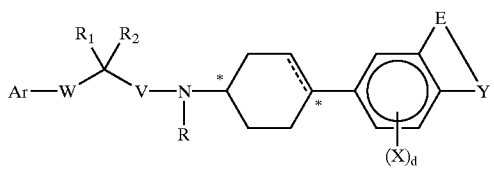

with the substituents as described above for Formula I.
Other preferred compounds of Formula III are:
Ar is unsubstituted or substituted phenyl;
X is independently selected from hydrogen or an electron withdrawing group selected from the group consisting of halogen, nitro, cyano, aminoalkyl, $CF_3$, $C(O)CH_3$, and haloalkyl; and
—E—Y— is selected from

—CH=CH—NH—, —N=CH—NH—;

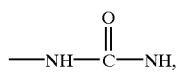

—N=N—NH—, and

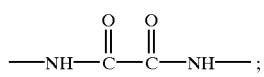

and
* denotes cis or trans.
Other preferred compounds are compounds of Formula I, Formula II, or Formula III wherein:

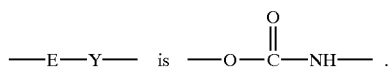

Other preferred compounds are compounds of Formula I, Formula II, or Formula III wherein:

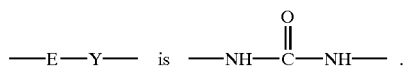

Other preferred compounds are compounds of Formula I, Formula II, or Formula III wherein:

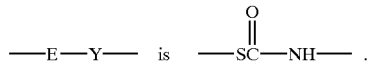

Preferably the pharmaceutical compositions are useful for the treatment of the neurodegenerative disorder Parkinson's disease.

Preferably, the pharmaceutical compositions are useful as a dopamine against or precursor thereof in amount effective to treat Parkinson's disease.

Other preferred compounds are those where * denotes cis.

The diradical group E—Y must contain a hydrogen bond donor functionality.

The term "alkyl" means a straight or branched hydrocarbon radical having from 1 to 12 carbon atoms unless otherwise specified, also known as a $C_1$–$C_{12}$ alkyl, and includes, for example, methyl, ethyl, 1-propyl, and 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-Nonyl, 2-Nonyl, 1-decyl, 2-decyl, 1-undecyl, 2-undecyl, 1-dodecyl, and 5-dodecyl. Alkyl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

Alkyl groups having two or more carbons may optionally contain 1 or 2 sites of unsaturation, the groups being known as alkenyl groups or radicals. Illustrative examples of an alkenyl group or radical having from 2 to 12 carbon atoms, also known as a $C_2$–$C_{12}$ alkenyl, include ethenyl, 1-propenyl, 2-propenyl, 1-buten-1-yl, 2-buten-1-yl, 1-penten-1-yl, 2-penten-1-yl, 1-penten-3-yl, 1-penten-5-yl, 1-hexen-1-yl, 1-hexen-4-yl, 2-hexen-1-yl, 3-hexen-1-yl, 2-octen-3-yl, 5-nonen-2-yl, 4-undecen-4-yl, and 5-dodecen-2-yl.

The term "aryl" means an aromatic carbocyclic ring having from 6 to 10 carbon atoms. Illustrative examples of an aryl group or radical include phenyl, 1-naphthyl, and 2-naphthyl. Aryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

The term "aralkyl" means an aryl-alkyl- group or radical wherein aryl and alkyl have the meanings as defined above. Illustrative examples of an arylalkyl group or radical include benzyl, 4-fluorophenylmethyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl.

The term "($C_3$–$C_7$ cycloalkyl)-alkyl" means an "alkyl" group (as described above) substituted thereon by a cycloalkyl group of from 3 to 7 carbon atoms such as cyclopentyl, cyclopropyl, cyclohexyl, or cycloheptyl.

The term "heteroatom" means nitrogen, oxygen, or sulfur.

The term "heteroaryl" means an unsaturated monocyclic group or radical of 5 or 6 atoms, an unsaturated fused bicyclic group or radical of from 8 to 10 atoms, or an unsaturated fused tricyclic group or radical of from 11 to 14 atoms, the cyclic groups having 1 or 2 heteroatoms independently selected from O, N, or S. Heteroaryl does not contain a hydrogen bond donor diradical group E—Y. Illustrative examples of monocyclic heteroaryl include 2- or 3-thienyl, 2- or 3-furanyl, 1-pyrrolyl, 1-imidazolyl, 1-pyrazolyl, 2-, 4-, or 5-oxazolyl, 2-, 4-, or 5-thiazolyl, 3-, 4-, or 5-isoxazolyl, 3-, 4-, or 5-isothiazolyl, 2-, 3-, or 4-pyridinyl, 3- or 4-pyridazinyl, 2- or 3-pyrazinyl, and 2-, 4- or 5-pyrimidinyl. Illustrative examples of bicyclic heteroaryl include 2-, 3-, 4-, 5-, 6-, 7-, or 8-quinolinyl, 1-, 3-, 4-, 5-, 6-, 7-, or 8-isoquinolinyl, 1-indolyl, 2-, 3-, 4-, 5-, 6-, or 7-benzo[b]thienyl, 2-, 4-, 5-, 6-, or 7-benzofuran, 2-, 4-, 5-, 6-, or 7-benzoxazolyl, 2-, 4-, 5-, 6-, or 7-benzothiazolyl, and 1-benzimidazolyl. Illustrative examples of tricyclic heteroaryl include 1-, 2-, 3-, or 4-dibenzofuranyl, 1-, 2-, 3-, or 4-dibenzothienyl and 1-, 2-, 3-, 4-, 5-, 6-, 7-, 8-, or 9-(1,2,3,4-tetrahydroacridinyl). All with the proviso that when Z in Formula I is attached via a heteroatom, Z is attached to a carbon atom of the heteroaryl group or radical. Heteroaryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

As used above, a fused bicyclic group or radical is a group wherein 2 ring systems share two and only 2 atoms.

As used above, a fused tricyclic group or radical is a group wherein 3 ring systems share four and only 4 atoms. "—" denotes a single or double bond.

The term "heteroaralkyl" means a heteroaryl-alkyl-group or radical wherein heteroaryl and alkyl have the meanings as defined above. Illustrative examples of an heteroaralkyl group or radical include 4-pyridyl-methyl, (4-fluoroquinolin-2-yl)methyl, 2-(isoxazol-3-yl)ethyl, and 12-(5-chlorothiophen-2-yl)-dodec-3-yl.

The term "halogen" means bromine, chlorine, fluorine, or iodine. The term "aminoalkyl" means an $H_2N$-alkyl-group or radical wherein alkyl has the meaning as defined above, which is a substituted alkyl group or radical containing from 1 to 3 substituents wherein at least one substituent is —$NH_2$.

The term "hydroxyalkyl" means an HO-alkyl-group or radical wherein alkyl has the meaning as defined above, which is a substituted alkyl group or radical containing from 1 to 3 substituents wherein at least 1 substituent is —OH.

The term "amino(hydroxy)alkyl" means an $H_2N(HO)$-alkyl-group or radical wherein alkyl has the meaning as defined above, which is a substituted alkyl group or radical containing from 2 or 3 substituents wherein at least 1 substituent is OH and 1 substituent is —$NH_2$.

The term "(aminocarbonyl)alkyl" means an $H_2NC(O)$-alkyl-group or radical wherein alkyl has the meaning as defined above, which is a substituted alkyl group or radical containing from 1 to 3 substituents wherein at least 1 substituent is —(O)C—$NH_2$.

The term "thioalkyl" means an HS-alkyl-group or radical wherein alkyl has the meaning as defined above, which is a substituted alkyl group or radical containing from 1 to 3 substituents wherein at least 1 substituent is —SH.

The term "alkenylalkyl" means a ($C_2$–$C_{12}$ alkenyl)-($C_1$–$C_{12}$ alkyl) group or radical wherein $C_2$–$C_{12}$ alkenyl and $C_1$–$C_{12}$ alkyl are as defined above.

The term "(methylthio)-alkyl-" means an $CH_3S$-alkyl-group or radical wherein alkyl has the meaning as defined above, which is a substituted alkyl group or radical containing from 1 to 3 substituents wherein at least 1 substituent is —$SCH_3$.

The term "carboxyalkyl" means an $HO_2C$-alkyl-group or radical wherein alkyl has the meaning as defined above, which is a substituted alkyl group or radical containing from 1 to 3 substituents wherein at least one substituent is —$CO_2H$.

The term "haloalkyl" means a halogen-alkyl-group or radical wherein halogen and alkyl have the meanings as defined above, which is a substituted alkyl group or radical containing from 1 to 3 substituents wherein at least 1 substituent is selected from F, Cl, Br, or I.

The term "ureidoalkyl" means an $H_2N$—(C=O)—NH-alkyl-group or radical wherein alkyl has the meanings as defined above, which is a substituted alkyl group or radical containing from 1 to 3 substituents wherein at least 1 substituent is $H_2N$—(C=O)—NH—.

The term "electron withdrawing group" means a group or radical selected from halogen, nitro, cyano, alkyl, $CF_3$, $C(O)CH_3$, $P(O)(O—R_9)_2$, $SO_2$—$R_9$, $SO_2NHR_9$, $C(O)NR_9R_9$, wherein $R_9$ is independently selected from $C_1$–$C_6$ alkyl or unsubstituted or substituted phenyl, —(C=NH)—$NH_2$, —(C=NH)—O-alkyl, methoxymethyl, or haloalkyl, wherein the substituents may be F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

The phrase "heterocycle, which heterocycle is a carboxylic acid or an amide isostere" means a 5- or 6-membered monocyclic ring containing from 1 to 4 heteroatoms selected from N, O, and S and providing a hydrogen bond donor moiety selected from NH, OH, and SH. Illustrative examples include the following structures:

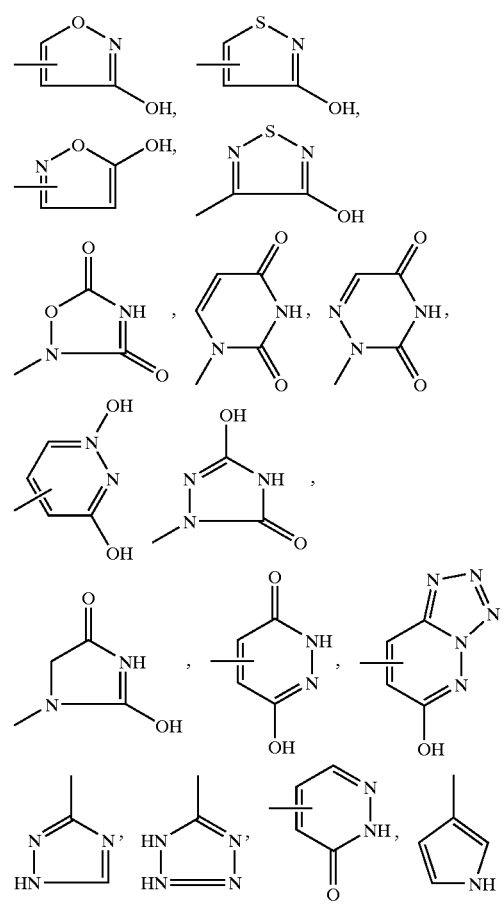

See also Greenwood J. R., Vaccarella G., Cooper H. R., Allan R. D., Johnston G. A. R, *Internet Journal of*

Chemistry, 1998;1(38)(Chart 4). Additional examples are well-known to the skilled artisan. (See, for example, (i) Lipinski C. A., Annual Reports in Medicinal Chemistry, 1986;21:Chaps 21, 27; (ii) Thornber C. W., Chem. Soc. Rev., 1979;8:563; (iii) Burger A., Progress in Drug Research, 1991;37:288–371.

The term "entgegen" means the stereoisomerism about a carbon-carbon double bond wherein the highest ranking substituent on each carbon are on opposite sides, which substituent ranking is based on the sequence rules of the Cahn-Ingold-Prelog system (March J., Advanced Organic Chemistry, 4$^{th}$ ed., New York: John Wiley & Sons 1992:109, 127 and references cited therein).

The term "zusammen" means the stereoisomerism about a carbon-carbon double bond wherein the highest ranking substituent on each carbon are on the same side, which substituent ranking is based on the sequence rules of the Cahn-Ingold-Prelog system (March J., supra., 1992).

The term "cis" means the stereoisomerism about a carbon-carbon double bond, a monocyclic ring, a fused bicyclic ring, or a bridged bicyclic ring wherein the highest ranking substituent on each of the two carbons of relevance are on the same side, which substituent ranking is based on the sequence rules of the Cahn-Ingold-Prelog system (March J., supra., 1992).

The term "trans" means the stereoisomerism about a carbon-carbon double bond, a monocyclic ring, a fused bicyclic ring, or a bridged bicyclic ring wherein the highest ranking substituent on each of the two carbons of relevance are on opposite sides, which substituent ranking is based on the sequence rules of the Cahn-Ingold-Prelog system (March J., supra., 1992).

The terms "cis" or "trans" refers to the relative stereochemistry of the groups attached to the cyclohexyl rings of Formulas I or II at the carbon atoms denoted by "*".

The term "$(X)_d$" means the group X is present 1 or 2 times on the phenylene to which it is attached, which group is independently selected from hydrogen or an electron withdrawing group wherein the electron withdrawing group is as defined above unless otherwise stated. The groups X can be the same or different.

The terms

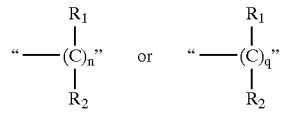

wherein n is an integer of from 1 to 6 and q is an integer of from 0 to 6 mean a chain of from 1 to 6 carbons or from 0 to 6 carbons, respectively, wherein each carbon is independently substituted, which substituents are the groups $R_1$ and $R_2$, wherein $R_1$ and $R_2$ are independently $R_1$ and $R_2$ in each occurrence can be the same or different) selected from the groups consisting of hydrogen, alkyl, OH, hydroxyalkyl, aminolkyl, aralkyl, or $N(R_4)(R_5)$ wherein $R_4$ and $R_5$ are independently selected from hydrogen, alkyl, aralkyl, heteroaryl, heteroaralkyl, aminoalkyl, hydroxyalkyl and thioalkyl, unless otherwise stated. The groups $R_1$ can be the same or different and the groups $R_2$ can be the same or different.

The group —E—Y—, together with the phenyl to which it is attached, is a bicycle that contains a hydrogen bond donor functionality.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see, for example, Green T., Wuts P. G., Protective Groups in Organic Synthesis, 2nd ed., New York: John Wiley & Sons, 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zInc Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

Some of the compounds of Formula I-III are capable of further forming pharmaceutically acceptable acid-addition and/or base salts. All of these forms are within the scope of the present invention.

Pharmaceutically acceptable acid addition salts of the compounds of Formula I-III include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., Journal of Pharmaceutical Science, 1977;66:1–19.

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I-III or a corresponding pharmaceutically acceptable salt of a compound of Formula I-III.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 to 100 mg preferably 0.5 to 100 mg according to the particular application and the potency of the active component. The composition can, if desired, also contain other compatible therapeutic agents.

In therapeutic use as antagonists or as agents for the treatment of diseases, the compounds utilized in the pharmaceutical method of this invention are administered at the initial dosage of about 0.01 to about 100 mg/kg daily. A daily dose range of about 0.01 to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

| Tablet Formulation | |
| --- | --- |
| Ingredient | Amount (mg) |
| Example 1 | 25 |
| Lactose | 50 |
| Cornstarch (for mix) | 10 |
| Cornstarch (for paste) | 10 |
| Magnesium stearate (1%) | 5 |
| Total | 100 |

Example 1, lactose and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of disease caused by over excitation of NMDA receptor channel complexes.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" (Green T., supra., 1991). A number of general reactions such as oxidations and reductions are not shown in detail but can be done by methods understood by one skilled in the art. General transformations are well-reviewed in "Comprehensive Organic Transformation" by Richard Larock, and the series "Compendium of Organic Synthetic Methods" published by Wiley-Interscience, 1989. In general, the starting materials were obtained from commercial sources unless otherwise indicated.

PREPARATION OF COMPOUNDS

Benzoxazolines

In general, these compounds can be prepared by a reductive amination reaction between an amine and 6-(4-Cyclohexanonyl)benzoxazolin-2-one 5 (Scheme 1). A synthetic procedure for the synthesis of 5 is shown in Scheme 2.

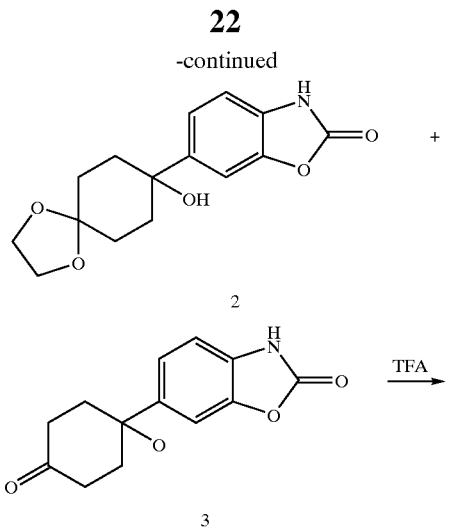

Scheme 1

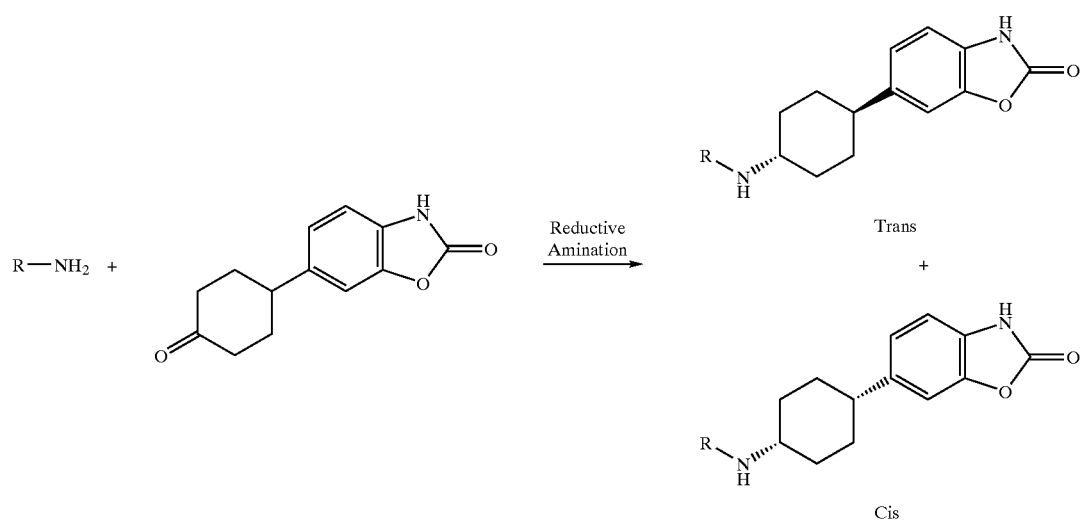

Scheme 2
Preparation of 6-(4-Cyclohexanonyl)benzoxazolin-2-one 5

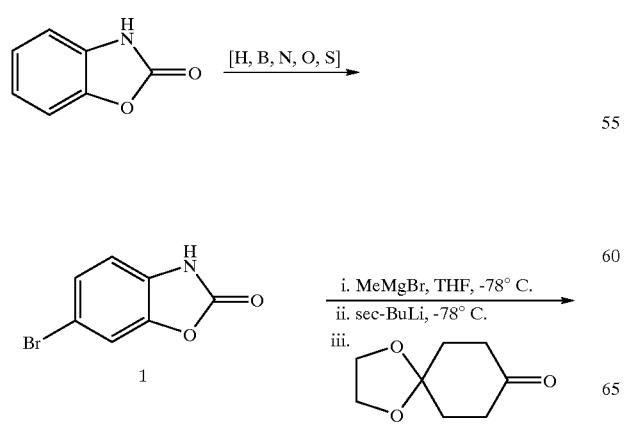

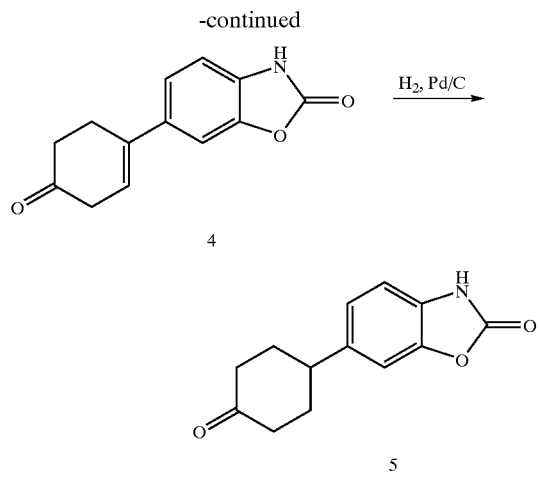

Step 1: N-Bromosuccinimide (26.6 g, 0.15 mol) was added to a stirred solution of 2-benzoxazolinone (20.0 g, 0.15 mol) in glacial acetic acid (220 mL), and the mixture was stirred at room temperature for 3 days. The reaction mixture was poured into H$_2$O (1.2 L), and the white solid that formed was collected. Recrystallization from hot EtOH (300 mL) gave bromide 1 (22.1 g, 70%) as an off-white solid: mp 190–195° C.; IR (KBr): 3278, 1779, 1736, 1623 cm$^{-1}$; $^1$H NMR (300 MHz, CD$_3$OD): δ 7.41 (d, J=2 Hz, 1H), 7.32 (dd, J=5, 2 Hz, 1H), 6.99 (d, J=5 Hz, 1H); CI MS (methane) (m/z): 215 [M+H]$^+$.

Step 2: Bromide 1 (12.8 g, 59.6 mmol) was dissolved in anhydrous THF (220 mL), and the solution was cooled to –78° C. Solutions of MeMgBr (21.9 mL of a 3.0 M solution in Et$_2$O, 65.6 mmol), sec-BuLi (50.4 mL of a 1.3 M solution in cyclohexane, 65.6 mmol), and 1,4-Cyclohexanedione mono-ethylene ketal (11.2 g, 71.5 mmol) in anhydrous THF (10 mL) were added sequentially at 30-minute intervals. After the final addition, the reaction mixture was allowed to warm to room temperature. The reaction was quenched by the addition of 1N HCl (25 mL). The reaction mixture was diluted with EtOAc (500 mL), washed with saturated NaCl (250 mL), dried (Na$_2$SO$_4$), filtered, and concentrated under reduced pressure to provide a mixture of 2 and 3, as a brown oil.

Step 3: The crude product from Step 2 was stirred in TFA (20 mL) at room temperature for 20 minutes. The red solution was poured into CHCl$_3$ (500 mL) and the organic layer was washed with H$_2$O (2×100 mL), saturated NaHCO$_3$, and saturated NaCl, dried (Na$_2$SO$_4$), filtered, and concentrated under reduced pressure. Purification by filtration through silica gel (eluent 9:1 CHCl$_3$/MeOH) gave a yellow oil. Crystallization from hexanes:EtOAc (3:1) gave 4 (8.1 g, 59%): $^1$H NMR (300 MHz, DMSO-d$_6$): δ 7.40 (d, J=1 Hz, 1H), 7.30 (dd, J=8, 1 Hz, 1H), 7.06 (d, J=8 Hz, 1H), 6.11 (t, J=4 Hz, 1H), 3.01 (d, J=2 Hz, 2H), 2.83 (t, J=7 Hz, 2H), 2.53 (m, 2H); CI MS (methane) (m/z): 230 [M+H]$^+$.

Step 4: A mixture of 4 (3.5 g, 15.3 mmol) in a 3:2 mixture of EtOAc/EtOH (100 mL) and 10% Pd/C (0.5 g) was shaken under a H$_2$ atmosphere at 50 psi for 4 hours. The solution was filtered through Celite and concentrated under reduced pressure. Crystallization from hexanes:EtOAc (3:1) gave 6-(4-cyclohexanonyl)benzoxazolin-2-one 5 (3.45 g, 98%) as a white solid: mp 202–211° C.; IR(KBr):3339, 1777, 1713, 1618 cm$^{-1}$; $^1$H NMR (300 MHz, DMSO-d$_6$): δ 7.26 (s, 1H), 7.08 (d, J=8 Hz, 1H), 7.01 (d, J=8 Hz, 1H), 3.08 (tt, J=14, 4 Hz, 1H), 2.63–2.51 (m, 2H), 2.24 (br d, J=14 Hz, 2H), 2.07–2.02 (m, 2H), 1.95–1.85 (dddd, J=14, 14, 14, 4 Hz, 2H).

Scheme 3
Preparation of α-(1-Aminoethyl)-4-methoxybenzyl alcohol hydrochloride 8

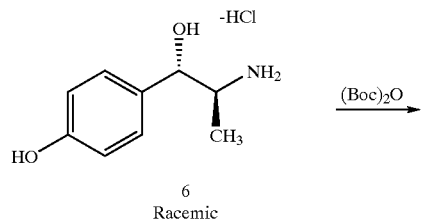

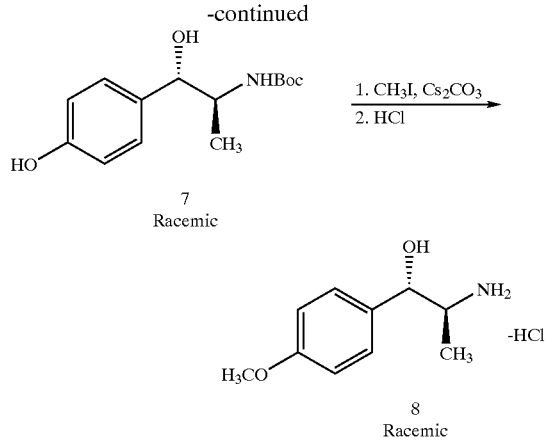

Step 1: To a stirred suspension of α-(1-aminoethyl)4-hydroxybenzyl alcohol hydrochloride 6 (5.0 g, 25 mmol), at 0° C., in CH$_2$Cl$_2$ (100 mL) was added Et$_3$N (10.6 mL, 76 mmol) followed by (Boc)$_2$O (5.9 g, 27 mmol). The reaction mixture was warmed to room temperature and stirred for 2 hours. The reaction mixture was washed with 2N HCl (2×50 mL). The organic layer was separated, and the aqueous layer was extracted with CH$_2$Cl$_2$. The combined organic solutions were washed with saturated NaCl, dried (Na$_2$SO$_4$), and filtered. Concentration under reduced pressure gave 7 (7.01 g, 93%) which was used without further purification.

Step 2: To a solution of 7 (7.0 g, 23 mmol) in acetone (120 mL) was added K$_2$CO$_3$ (10.2 g, 73 mmol) followed by MeI (3.3 mL, 52 mmol). The reaction mixture was heated under reflux, under a N$_2$ atmosphere for 15 hours. After cooling to room temperature, the reaction mixture was filtered off, and the filtrate was concentrated under reduced pressure. Purification by flash chromatography (silica, 95:5 CH$_2$Cl$_2$:MeOH) and (silica, 1:4 EtOAc:hexanes) afforded 3.0 g (41%) of desired material, which was used without further purification: $^1$H NMR (500 MHz, CDCl$_3$): δ 7.25 (d, J=7 Hz, 2H), 6.88 (d, J=7 Hz, 2H), 4.80–4.75 (m, 1H), 4.60–4.54 (br s, 1H), 4.00–3.93 (br s, 1H), 3.80 (s, 3H), 3.12–3.04 (br s, 1H), 1.46 (s, 9H), 0.99 (d, J=7 Hz, 3H).

Step 3: The carbamate 7 (3.0 g, 9.4 mmol) was stirred in HCl (25 mL of a 4 M solution in dioxane, 100 mmol) for 3 hours. The reaction mixture was then diluted with Et$_2$O, which resulted in a white precipitate that was collected by filtration and dried to yield the desired amine 8 as the HCl salt (1.3 g, 54%): $^1$H NMR (500 MHz, CD$_3$OD): δ 7.32 (d, J=9 Hz, 2H), 6.94 (d, J=9 Hz, 2H), 4.85 (s, 1H), 3.79 (s, 3H), 3.49–3.45 (m, 1H), 1.25 (d, J=7 Hz, 3H).

Reductive Amination

General Methods

HCl salts were prepared by treatment of a MeOH solution of the amine with excess HCl in Et$_2$O (1.0 M). The salts were isolated either by filtration, if they precipitated directly from the etherial solution, or by first removal of the solvent under reduced pressure, and then crystallization (Et$_2$O/MeOH).

Purity was determined by reversed phase HPLC by the following methods:

Method A: column: YMC J'Sphere C18, ODS-M80, 150×4.6 mm, 4μ; solvent A: 0.1% $H_3PO_4$ in $H_2O$; solvent B: 0.1% $H_3PO_4$ in $CH_3CN$; gradient: 10% to 100% B over 15 minutes; flow: 1 mL min$^{-1}$; detection: 210 nm.

Method B: column: YMC J'Sphere C18, ODS-M80, 150×4.6 mm, 4μ; solvent A: 0.1% $H_3PO_4$ in $H_2O$; solvent B: 0.1% $H_3PO_4$ in MeOH; gradient: 10% to 100% B over 15 minutes; flow: 1 mL min$^{-1}$; detection: 210 nm.

Method C: column: Dynamax 300 Å C18, 250×4.6 mm+guard, 5μ; solvent A: 0.1% $H_3PO_4$ in $H_2O$; solvent B: 0.1% $H_3PO_4$ in $CH_3CN$; gradient: 10% to 100% B over 25 minutes; flow: 1 mL min$^{-1}$; detection: 215 nm.

Method D: column: Dynamax 300 Å C18, 250×4.6 mm+guard, 5μ; solvent A: 0.1% $H_3PO_4$ in $H_2O$; solvent B: 0.1% $H_3PO_4$ in MeOH; gradient: 10% to 100% B over 30 minutes; flow: 1 mL min$^{-1}$; detection: 215 nm.

Method E: column: YMC J'Sphere C18, ODS-M80, 150×4.6 mm, 4μ; solvent A: 0.1% formic acid in $H_2O$; solvent B: 0.1% formic acid in MeOH; gradient: 10% to 100% B over 20 minutes; flow: 1 mL min$^{-1}$; detection: 225 nm.

Existing Literature:

2-(4-Fluorophenoxy)ethylamine: Beilstein Registry Number: 1941572; CAS #: 6096-89-5; Shtacher G., Taub W., *J. Med. Chem.*, 1966;9:197–203.

3-(4-Fluorophenyl)propylamine: Beilstein Registry Number: 7757402; Fujimura K., Matsumoto J., Niwa M., Kobayshi T., Kawashima Y., et al., *Bioorg. Med. Chem.*, 1997;5:1675–1684.

3-Phenylsulfanylpropylamine: Beilstein Registry Number: 3695289; CAS #: 34946-13-9; References to use of: Uher M., Jendrichovsky J., *Collect. Czech Chem. Commun.*, 1973;38:620–624. Tucker H., Coope J. F., *J. Med. Chem.*, 1978;21:769–773.

3-p-Tolylpropylamine: Beilstein Reference Number: 3235743; CAS #: 54930-39-1; v.Braun, Wirz, *Chem. Ber.*, 1927;60:107.

2-Methyl-3-phenylpropylamine: Beilstein Reference Number: 3237614; CAS #: 77916-78-0; Belletire J. L., Fry D. F., *Synth. Commun*, 1988;18:29–36.

3-Phenyl-prop-2-ynylamine: Beilstein Reference Number: 2802264; CAS #: 78168-74-8; Tomassy B., Zwierzak A., *Synth. Commun.*, 1988;28:1201–1214.

3-(4-Fluorophenyl)-propionic acid 2,5-dioxo-pyrrolidin-1-yl ester: Beilstein Reference Number: 6657466; Shiosaki K., Lin C. W., Kopeka H. K., Craig R. A., Bruce, et al., *J. Med. Chem.*, 1992;35:2007–2014.

6-Bromo-5-methyl-3H-benzoxazol-2-one: Kalcheva V. B., Deligeorgiev T. G., Zaneva D. A., *Dyes and Pigments*, 1991;15:275–278.

(4-Iodophenyl)dimethylamine: CAS #: 698-70-4; Yang S. G., Kim Y. H., *Tetrahedron Lett.*, 1999;40:6051–6054.

EXAMPLE 1

6-[trans-4-(3-Phenylpropylamino)cyclohexyl]-3H-benzoxazol-2-one

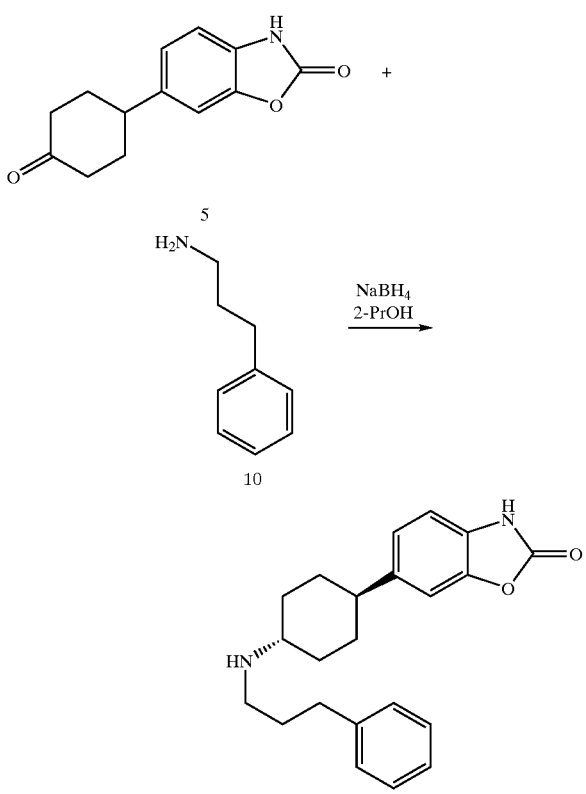

To a solution of ketone 5 (0.50 g, 2.0 mmol) in 2-propanol (30 mL) was added 3 Å molecular sieves and 3-phenyl-1-propylamine 10 (0.39 g, 2.0 mmol). The reaction mixture was stirred for 4 hours. Sodium borohydride (0.11 g, 2.83 mmol) was added, and the reaction mixture was stirred overnight, quenched with MeOH, and concentrated under reduced pressure. Purification by flash chromatography (silica, 9.5:5:1 $CH_2Cl_2$:MeOH:$NH_4OH$) gave 6-[trans-4-(3-phenylpropylamino)-cyclohexyl]-3H-benzoxazol-2-one (0.30 g, 42%): mp 166–170° C.; IR (KBr): 2933, 1761, 1653, 1582 cm$^{-1}$; $^1$H NMR (500 MHz, DMSO-d$_6$): δ 9.09 (s, 1H), 7.30–7.19 (m, 6H), 7.03 (d, J=9 Hz, 1H), 6.68 (d, J=9 Hz, 1H), 2.66 (m, 1H), 2.55 (t, J=8 Hz, 2H), 2.37 (tt, J=10, 2 Hz, 1H), 1.98 (d, J=10 Hz, 1H), 1.96 (d, J=10 Hz, 1H), 1.76 (d, J=3 Hz, 1H), 1.56 (m, 1H), 1.45 (m, 1H), 1.39 (m, 1H), 1.18–1.05 (m, 6H); CI-MS (methane) (m/z): 351 [M+H]$^+$; HRMS-API (m/z): [M+H]$^+$ calcd for $C_{22}H_{26}N_2O_2$, 351.2072; found, 351.2178; HPLC: method A, 7.66 minutes (96.9%); method B, 14.14 minutes (97.7%); Anal. Calcd for $C_{22}H_{26}N_2O_2 \cdot H_2O$: C, 71.71; H, 7.66; N, 7.60. Found: C, 71.70; H, 7.62; N, 7.20.

The following compounds were prepared from the appropriate amines following the standard conditions. In some cases THF was used as a co-solvent to increase the solubility of the starting materials. The trans-isomer was usually formed as the major product. The cis-isomer was characterized when sufficient material was isolated.

EXAMPLE 2

6-{trans-4-[2-(4-Fluorophenoxy)ethylamino]cyclohexyl}-3H-benzoxazol-2-one

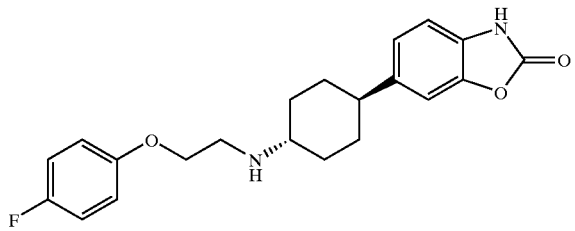

Coupling of ketone 5 and 2-(4-fluorophenoxy)ethylamine gave 6-{trans-4-[2-(4-fluorophenoxy)ethylamino]cyclohexyl}-3H-benzoxazol-2-one (0.14 g, 20%): mp 172–176° C.; IR (KBr): 2931, 1759, 1654 cm$^{-1}$; $^1$H NMR (500 MHz, CD$_3$OD): δ 7.10–6.90 (m, 7H), 4.08 (t, J=5 Hz, 2H), 3.04 (t, J=5 Hz, 2H), 2.62 (tt, J=14, 2 Hz, 1H), 2.56 (tt, J=14, 2 Hz, 1H), 2.11 (br d, J=12 Hz, 2H), 1.92 (br d, J=12 Hz, 2H), 1.57 (dddd, J=12, 12, 12, 2 Hz, 2H), 1.33 (dddd, J=12, 12, 12, 2 Hz, 2H); FAB-MS (m/z): 371 [M+H]$^+$; HRMS-API (m/z): [M+H]$^+$ calcd for C$_{21}$H$_{23}$FN$_2$O$_3$, 371.1771; found, 371.1784; HPLC: method A, 7.51 minutes (96.4%); method B, 13.82 minutes (96.0%); Anal. Calcd for C$_{21}$H$_{23}$FN$_2$O$_3$.0.25H$_2$O: C, 67.27; H, 6.32; N, 7.47. Found: C, 67.09; H, 6.40; N, 7.33.

EXAMPLE 3

6-[trans-4-(2-Phenoxyethylamino)cyclohexyl]-3H-benzoxazol-2-one

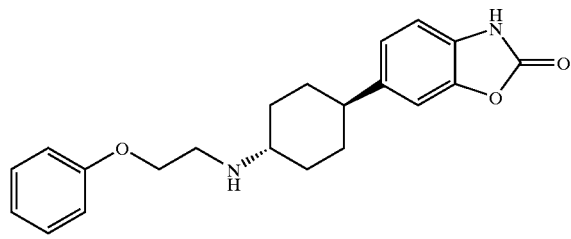

Coupling of ketone 5 and 2-phenoxyethylamine gave 6-[trans-4-(2-phenoxyethylamine)cyclohexyl]-3H-benzoxazol-2-one (0.18 g, 24%): mp 159–162° C.; IR (KBr): 3262, 2926, 1759, 1654, 1600 cm$^{-1}$; $^1$H NMR (500 MHz, DMSO-d$_6$): δ 7.34 (t, J=2 Hz, 2H), 7.21 (s, 1H), 7.05–6.96 (m, 5H), 4.06 (t, J=5 Hz, 2H), 2.98 (t, J=5 Hz, 2H), 2.51 (tt, J=11, 2 Hz, 1H), 2.49 (tt, J=11, 2 Hz, 1H), 2.04 (br d, J=11 Hz, 2H), 1.83 (br d, J=11 Hz, 2H), 1.52 (dddd, J=11, 11, 11, 2 Hz, 2H), 1.19 (dddd, J=11, 11, 11, 2 Hz, 2H); API-MS (m/z): 353 [M+H]$^+$; HRMS-API (m/z): [M+H]$^+$ calcd for C$_{21}$H$_{24}$N$_2$O$_3$, 353.1865; found, 353.1868; HPLC: method A, 7.39 minutes (99.5%); method B, 13.49 minutes (100%); Anal. Calcd for C$_{21}$H$_{24}$N$_2$O$_3$.0.25H$_2$O: C, 70.67; H, 6.92; N, 7.85. Found: C, 70.43; H, 6.89; N, 7.49.

EXAMPLE 4

(a) 6-{trans-4-[3-(4-Fluorophenyl)propylamino]cyclohexyl}-3H-benzoxazol-2-one
(b) 6-{cis-4-[3-(4-Fluorophenyl)propylamino]cyclohexyl}-3H-benzoxazol-2-one

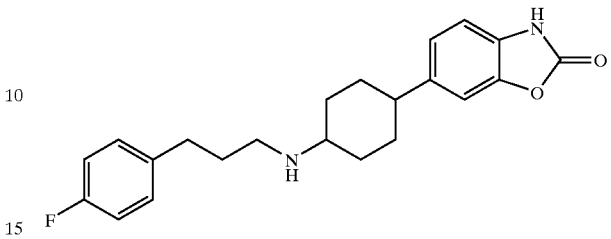

Coupling of ketone 5 and 3-(4-fluorophenyl)-1-propylamine gave (a) the trans isomer 6-{trans-4-[3-(4-fluorophenyl)propylamino]cyclohexyl}-3H-benzoxazol-2-one (HCl salt) (0.15 g, 21%): mp 293–307° C.; IR (KBr): 2941, 1759 cm$^{-1}$; $^1$H NMR (500 MHz, DMSO-d$_6$): δ 8.83 (broad s, 1H), 7.28 (t, J=6, 3 Hz, 1H), 7.26 (s, 1H), 7.15 (t, J=6, 3 Hz, 2H), 7.00 (m, 4H), 3.07 (m, 1H), 2.91 (m, 2H), 2.66 (t, J=2 Hz, 2H), 2.50 (m, 1H), 2.13 (m, 2H), 1.92 (m, 2H), 1.85 (m, 3H), 1.49 (m, 4H); API-MS (m/z): 369 [M+H]$^+$; HRMS-API (m/z): [M+H]$^+$ calcd for C$_{22}$H$_{25}$FN$_2$O$_2$, 369.1978; found, 369.1980; HPLC: method A, 7.78 minutes (99.8%); method B, 14.29 minutes (100%); Anal. Calcd for C$_{22}$H$_{25}$FN$_2$O$_2$.HCl.0.5H$_2$O: C, 63.84; H, 6.57; N, 6.77. Found: C, 63.64; H, 6.50; N, 6.57 and (b) the cis isomer 6-{cis-4-[3-(4-fluorophenyl)propylamino]-cyclohexyl}-3H-benzoxazol-2-one (750 mg, 35%): $^1$H NMR (500 MHz, CD$_3$OD): δ 7.27–7.22 (m, 3H), 7.13 (d, J=8 Hz, 1H), 7.05–7.10 (m, 3H), 3.43–3.39 (m, 1H), 3.08–3.04 (m, 2H), 2.85–2.80 (m, 1H), 2.76–2.72 (m, 2H), 2.08–1.81 (m, 10H).

EXAMPLE 5

(a) 6-[trans-4-(2-Phenylsulfanylethylamino)cyclohexyl]-3H-benzoxazol-2-one
(b) 6-[cis-4-(2-Phenylsulfanylethylamino)cyclohexyl]-3H-benzoxazol-2-one

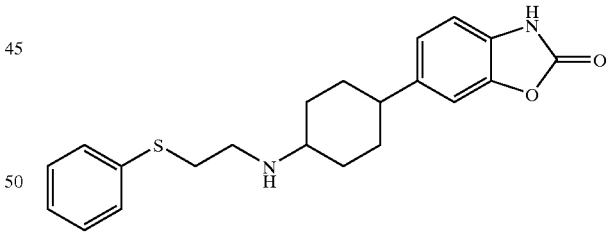

Coupling of ketone 5 and 2-phenylsulfanylethylamine gave (a) the trans isomer 6-[trans-4-(2-phenylsulfanylethylamino)cyclohexyl]-3H-benzoxazol-2-one isolated as the HCl salt (0.13 g, 14%): mp 241–243° C.; IR (KBr): 2940, 2858,1762 cm$^{-1}$; $^1$H NMR (500 MHz, CD$_3$OD): δ 7.50–7.30 (m, 5H), 7.11 (s, 1H), 7.03–6.98 (m, 2H) 3.30 (s, 4H), 3.24 (tt, J=14, 2 Hz, 1H), 2.60 (tt, J=14, 2 Hz, 1H), 2.18 (br d, J=12 Hz, 2H), 1.99 (br d, J=12 Hz, 2H), 1.57 (dddd, J=12, 12, 12, 2 Hz, 4H); API-MS (m/z): 369 [M+H]$^+$ HRMS-API (m/z): [M+H]$^+$ calcd for C$_{21}$H$_{24}$N$_2$O$_2$S, 369.1636; found, 369.1638; HPLC: method A, 7.86 minutes (98.0%); method B, 14.46 minutes (99.1%); Anal. Calcd for C$_{21}$H$_{24}$N$_2$O$_2$S.HCl.0.25H$_2$O: C, 61.60; H, 6.28; N, 6.84. Found: C, 61.60; H, 6.16; N, 6.68; and (b) The cis-isomer 6-[cis-4-(2-phenylsulfanyl-ethylamino)-cyclohexyl]-3H-benzoxazol-2-one was isolated as the HCl salt (0.14 g, 9%): mp 182–190° C.; IR (KBr): 2939, 1762 cm⁻¹; ¹H NMR (500 MHz, DMSO-d₆): δ 8.80 (br s, 2H), 7.44–6.98 (m, 8H), 3.37–3.28 (m, 4H), 3.15–3.13 (m, 1H), 2.80–2.75 (m, 1H), 195–1.63 (m, 8H); API-MS (m/z): 369 [M+H]⁺; HPLC: method A, 7.92 minutes (98.4%); method B, 14.47 minutes (98.2%); Anal. Calcd for C₂₁H₂₄N₂O₂S.HCl.0.5OH₂O: C, 60.93; H, 6.33; N, 6.77. Found: C, 60.91; H, 6.37; N, 6.69.

EXAMPLE 6
6-[4-(3-Phenylpropylamino)cyclohex-1-enyl]-3H-benzoxazol-2-one

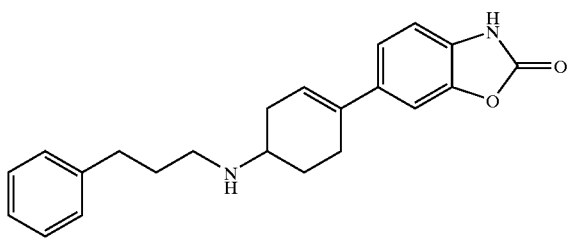

To a solution of ketone 3 (0.50 g, 2.0 mmol) in 2-propanol (30 mL) was added 3 Å molecular sieves and 3-phenyl-1-propylamine (10) (0.39 g, 2.0 mmol). The reaction mixture was stirred for 4 hours. Sodium borohydride (0.11 g, 2.83 mmol) was added, and the reaction mixture was stirred overnight, quenched with MeOH, and concentrated under reduced pressure. Purification by flash chromatography (silica, 9.5:5:1 CH₂Cl₂:MeOH:NH₄OH) gave 6-[4-(3-phenylpropylamino)cyclohex-1-enyl]-3H-benzoxazol-2-one (0.12 g, 21%): mp 293–295° C.; IR (KBr): 2950, 1779, 1496 cm⁻¹; ¹H NMR (500 MHz, DMSO-d₆): δ 7.32 (s, 1H), 7.30–7.17 (m, 6H), 7.00 (d, J=1 Hz, 1H), 6.03 (m, 1H), 2.79 (m, 1H), 2.65 (m, 4H), 2.50 (m, 4H), 1.94 (m, 2H), 1.75 (m, 2H), 1.47 (m, 2H); API-MS (m/z): 349 [M+H]⁺; HRMS-API (m/z): [M+H]⁺ calcd for C₂₂H₂₄N₂O₂, 349.1916; found, 349.1917; HPLC: method A, 7.67 minutes (97.9%); method B, 14.06 minutes (99.8%); Anal. Calcd for C₂₂H₂₄N₂O₂.0.8H₂O: C, 72.82; H, 7.11; N, 7.72. Found: C, 72.55; H, 7.13; N, 7.34.

EXAMPLE 7
6-[trans-4-(2-Phenylaminoethylamino)cyclohexyl]-3H-benzoxazol-2-one

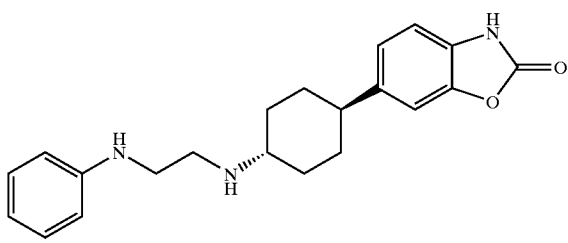

Coupling of ketone 5 and 2-(4-aminophenyl)ethylamine gave 6-[trans-4-(2-phenylaminoethylamino)cyclohexyl]-3H-benzoxazol-2-one (0.18 g, 26%): mp 293–295° C.; IR (KBr): 2950, 1779, 1496 cm⁻¹; ¹H NMR (500 MHz, DMSO-d₆): δ 7.16 (s, 1H), 7.09 (t, J=6 Hz, 2H), 7.01 (dd, J=6, 1 Hz, 2H), 6.98–6.53 (m, 3H), 5.51 (br s, 1H), 3.18 (m, 2H), 2.86 (m, 2H), 2.64 (m, 1H), 2.49 (m, 1H), 2.01 (br d, J=9 Hz, 2H), 1.81 (br d, J=9 Hz, 2H), 1.47 (dddd, J=9, 9, 9, 1 Hz, 2H), 1.24 (dddd, J=9, 9, 9, 1 Hz, 2H); API-MS (m/z): 352 [M+H]⁺; HPLC: method A, 7.36 minutes (98.2%); method B, 13.46 minutes (98.5%); Anal. Calcd for C₂₁H₂₅N₃O₂: C, 71.77; H, 7.17; N, 11.96. Found: C, 65.64; H, 7.09; N, 10.08.

EXAMPLE 8
6-{trans-4-[2-(4-Fluorophenylsulfanyl)ethylamino]cyclohexyl}-3H-benzoxazol-2-one

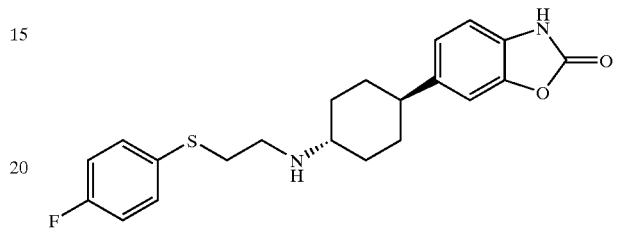

Coupling of ketone 5 and 2-(4-fluorophenylsulfanyl)ethylamine gave 6-{trans-4-[2-(4-fluorophenylsulfanyl)ethylamino]cyclohexyl}-3H-benzoxazol-2-one isolated as the HCl salt (0.10 g, 5%): mp 254–256° C.; IR (KBr): 2933, 2809, 1775 cm⁻¹; ¹H NMR (500 MHz, DMSO-d₆): δ 8.91 (br s, 2H), 7.53–7.50 (m, 2H), 7.25–7.20 (m, 3H), 7.18–7.14 (m, 2H) 3.30–3.23 (m, 2H), 3.10–3.07 (m, 3H), 2.52–2.50 (m, 1H), 2.11–2.05 (m, 2H), 1.85–1.84 (m, 2H), 1.51–1.42 (m, 4H); API-MS (m/z): 387 [M+H]⁺; HPLC: method A, 14.65 minutes (>99%); Anal. Calcd for C₂₁H₂₃FN₂O₂S.HCl: C, 59.64; H, 5.72; N, 6.62. Found: C, 59.49; H, 5.73; N, 6.47.

EXAMPLE 9
6-{trans-4-[(R)-1-Methyl-3-phenylpropylamino]cyclohexyl}-3H-benzoxazol-2-one

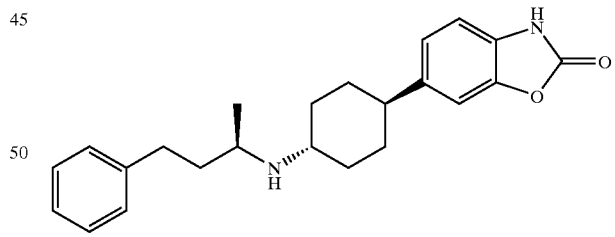

Coupling of ketone 5 and (R)4-phenyl-2-butylamine gave 6-{trans-4-[(R)-1-methyl-3-phenylpropylamino]cyclohexyl}-3H-benzoxazol-2-one isolated as an HCl salt (0.12 g, 21%): mp 291–304° C.; IR (KBr): 2945, 1752, 1623 cm⁻¹; ¹H NMR (300 MHz, DMSO-d₆): δ 8.67 (s, 1H), 7.35–7.30 (m, 5H), 7.22 (s, 1H), 6.98 (m, 2H), 3.26 (m, 4H), 2.74–2.61 (m, 2H), 2.14 (m, 2H), 1.93–1.74 (m, 3H), 1.53 (m, 4H), 1.33 (d, J=6 Hz, 3H); API-MS (m/z): 365 [M+H]⁺; HPLC: method A, 8.11 minutes (97.7%); method B, 14.96 minutes (99.7%); [α]²⁵_D+17.5° (c 0.08, MeOH); Anal. Calcd for C₂₃H₂₈N₂O₂.HCl.0.5H₂O: C, 67.39; H, 7.38; N, 6.83. Found: C, 67.38; H, 7.17; N, 6.71.

EXAMPLE 10
6-{trans-4-[(S)-1-Methyl-3-phenylpropylamino]cyclohexyl}-3H-benzoxazol-2-one

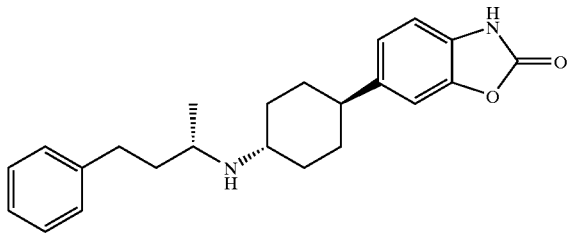

Coupling of ketone 5 and and (S)-4-phenyl-2-butylamine gave 6-{trans-4-[(S)-1-methyl-3-phenylpropylamino]cyclohexyl}-3H-benzoxazol-2-one (0.12 g, 21%): mp 174–176° C.; IR (KBr): 2925, 1761, 1654, 1583 cm$^{-1}$; $^1$H NMR (500 MHz, DMSO-d$_6$): δ 7.23–7.12 (m, 5H), 7.11 (s, 1H), 7.09 (m, 2H), 2.71 (tt, J=10, 2 Hz, 1H), 2.56 (t, J=5 Hz, 2H), 2.48 (tt, J=10, 2 Hz, 1H), 1.87–1.70 (m, 2H), 1.63 (d, J=7 Hz, 2H), 1.58 (m, 1H), 1.57–1.36 (m, 4H), 1.11–1.04 (m, 4H), 1.01 (d, J=9 Hz, 3H); API-MS (m/z): 365 [M+H]$^+$; HPLC: method B, 14.91 minutes (98.6%); [α]$^{25}$D –8.0° (c 0.125, MeOH); Anal. Calcd for C$_{23}$H$_{28}$N$_2$O$_2$: C, 75.79; H, 7.74; N 7.69. Found: C, 75.48; H, 8.02; N, 7.30.

EXAMPLE 11
(a) 6-{trans-4-[(1S,2S)-2-Hydroxy-2-(4-methoxyphenyl)-1-methylethylamino]-cyclohexyl}-3H-benzoxazol-2-one
(b) 6-{cis-4-[(1S,2S)-2-Hydroxy-2-(4-methoxyphenyl)-1-methylethylamino]-cyclohexyl}-3H-benzoxazol-2-one

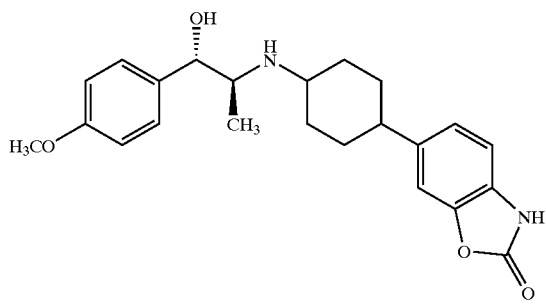

Coupling of ketone 5 and and α-(1-aminoethyl)-4-methoxybenzyl alcohol hydrochloride 8 gave (a) the trans-isomer 6-{trans-4-[(1S,2S)-2-hydroxy-2-(4-methoxyphenyl)-1-methylethylamino]cyclohexyl}-3H-benzoxazol-2-one isolated the HCl salt (0.18 g, 12%): mp 241–249° C.; IR (KBr): 3300, 2943, 1758 cm$^{-1}$; $^1$H NMR (500 MHz, DMSO-d$_6$): δ 8.52 (br s, 2H), 7.33 (d, J=9 Hz, 2H), 7.19 (s, 1H), 7.14–7.00 (m, 2H), 6.95 (d, J=9 Hz, 2H), 6.05 (br s, 1H), 5.09 (br s, 1H), 3.76 (s, 3H), 3.47 (br s, 1H), 3.23–3.20 (m, 1H), 2.60–2.46 (m, 1H), 2.31–2.08 (m, 2H), 1.91–1.87 (m, 2H), 1.65–1.50 (m, 4H), 0.97 (d, J=7 Hz, 3H); CI-MS (methane) (m/z): 397 [M+H]$^+$; HRMS-API (m/z): [M+H]$^+$ calcd for C$_{23}$H$_{28}$N$_2$O$_4$, 397.2127; found, 397.2126; HPLC: method A, 6.69 minutes (97.8%); method B, 11.90 minutes (99.3%); Anal. Calcd for C$_{23}$H$_{28}$N$_2$O$_4$.HCl.0.50H$_2$O: C, 62.51; H, 6.84; N, 6.34. Found: C, 62.63; H, 6.78; N, 6.25; and
(b) the cis-isomer 6-{cis-4-[(1S,2S)-2-hydroxy-2-(4-methoxyphenyl)-1-methylethylamino]cyclohexyl}-3H-benzoxazol-2-one was isolated as the HCl salt (0.068 g, 4%): mp 195–197C; IR (KBr): 2940, 1758 cm$^{-1}$; $^1$H NMR (500 MHz, DMSO-d$_6$): δ 8.40–8.25 (m, 2H), 7.37–7.32 (m, 3H), 7.13 (br d, J=8 Hz, 1H), 7.03 (d, J=8 Hz, 1H), 6.94 (d, J=9 Hz, 2H), 6.05–6.03 (m, 1H), 5.16–5.15 (m, 1H), 3.75 (s, 3H), 3.56–3.41 (m, 2H), 2.73–2.79 (m, 1H), 2.12–1.78 (m, 6H), 1.73–1.65 (m, 2H), 0.99 (d, J=7 Hz, 3H); CI-MS (methane) (m/z): 397 [M+H]$^+$; HRMS-API (m/z): [M+H]$^+$ calcd for C$_{23}$H$_{28}$N$_2$O$_4$, 397.2127; found, 397.2125; HPLC: method A, 7.04 minutes (96.4%); method B; 12.44 minutes (96.8%); Anal. Calcd for C$_{23}$H$_{28}$N$_2$O$_4$.HCl. 0.25H$_2$O: C, 63.15; H, 6.80; N, 6.40. Found: C, 63.02; H, 6.69; N, 6.29.

EXAMPLE 12
6-{trans-4-[(1S,2R)-2-Hydroxy-1-methyl-2-phenylethylamino]cyclohexyl}-3H-benzoxazol-2-one

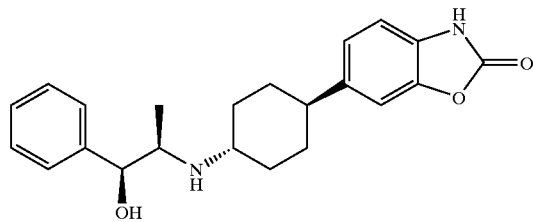

Coupling of ketone 5 and (1S,2R)-(+)-Norephedrine hydrochloride gave the trans-isomer 6-{trans-4-[(1S,2R)-2-hydroxy-1-methyl-2-phenylethylamino]-cyclohexyl}-3H-benzoxazol-2-one isolated as the HCl salt (0.12 g, 21%): mp 251–256° C.; IR (KBr): 2942, 1754, 1624 cm$^{-1}$; $^1$HNMR (300 MHz, DMSO-d$_6$): δ 8.59 (s, 2H), 7.44–7.30 (m, 5H), 7.20 (s, 1H), 7.02–6.98 (m, 2H), 6.17 (d, J=4 Hz, 1H), 5.15 (m, 1H), 3.52 (m, 1H), 2.58 (m, 1H), 2.47 (m, 1H), 2.37 (m, 1H), 1.88 (m, 2H), 1.62 (m, 4H), 0.97 (d, J=6 Hz, 3H); API-MS (m/z): 367 [M+H]$^+$; HPLC: method A, 7.59 minutes (97.9%); method B, 14.18 minutes (98.5%); Anal. Calcd for C$_{22}$H$_{26}$N$_2$O$_3$HCl: C, 62.77; H, 6.94; N, 6.66. Found: C, 62.59; H, 6.64; N, 6.39.

EXAMPLE 13
(a) 6-[cis-4-(3-p-Tolylpropylamino)cyclohexyl]-3H-benzoxazol-2-one
(b) 6-[trans-4-(3-p-Tolylpropylamino)cyclohexyl]-3H-benzoxazol-2-one

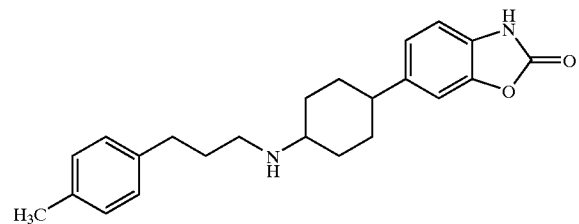

Coupling of ketone 5 and and 3-p-tolylpropylamine gave (a) the cis-isomer 6-[cis-4-(3-p-tolylpropylamino)cyclohexyl]-3H-benzoxazol-2-one isolated as the HCl salt (0.12 g, 7%): mp 263–265° C.; IR (KBr): 2941, 1765 cm$^{-1}$; $^1$H NMR (500 MHz, DMSO-d$_6$): δ 8.64 (br s, 2H), 7.36–7.35 (m, 1H), 7.12–6.99 (m, 6H), 3.33–3.29 (m, 1H), 2.90–2.96 (m, 2H), 2.66–2.60 (m, 3H), 2.27 (s, 3H), 2.01–1.89 (m, 6H), 1.77–1.69 (m, 2H), 1.65–1.59 (m, 2H); CI MS (methane) (m/z): 365 [M+H]$^+$; HRMS-API (m/z): [M+H]$^+$ calcd for C$_{23}$H$_{28}$N$_2$O$_2$, 365.2229; found, 365.2228; HPLC: method A, 7.14 minutes (95.2%); method B, 13.08 minutes (96.6%); Anal. Calcd for C$_{23}$H$_{28}$N$_2$O$_2$HCl.0.50H$_2$O: C, 68.13; H, 7.33; N, 6.91. Found: C, 68.33; H, 7.27; N, 6.92; and (b) the trans-isomer 6-[trans-4-(3-p-tolylpropylamino) cyclohexyl]-3H-benzoxazol-2-one was isolated as the HCl salt (0.27 g, 16%): mp 295–301° C.; IR (KBr): 2942, 1763 cm$^{-1}$; $^1$HNMR (500 MHz, DMSO-d$_6$): δ 8.79 (m, 2H), 7.17 (br s, 1H), 7.13–7.11 (m, 4H), 7.02–6.97 (m, 2H) 3.05 (br s, 1H), 2.92–2.89 (m, 2H), 2.63 (t, J=8 Hz, 2H), 2.53–2.50 (m, 1H), 2.27 (s, 3H), 2.16–2.10 (m, 2H), 1.95–1.85 (m, 4H), 1.55–1.46 (m, 4H); CI-MS (methane) (m/z): 365 [M+H]$^+$; HPLC: method A, 7.02 minutes (96.5%); method B, 13.11 minutes (98.8%); Anal. Calcd for C$_{23}$H$_{28}$N$_2$O$_2$.HCl: C, 68.90; H, 7.29; N, 6.99. Found: C, 68.78; H, 7.21; N 6.87.

EXAMPLE 14

6-{trans-4-[3-(4-Trifluoromethylphenyl)propylamino] cyclohexyl}-3H-benzoxazol-2-one

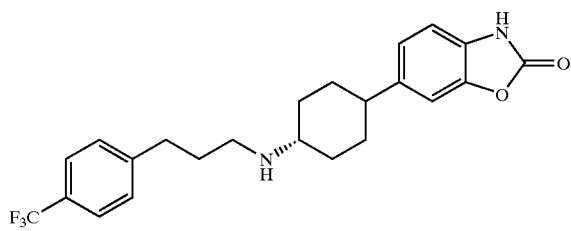

Coupling of ketone 5 and 3-(4-trifluoromethylphenyl)-1-propylamine gave 6-{trans-4-[3-(4-trifluoromethylphenyl) propylamino]cyclohexyl}-3H-benzoxazol-2-one isolated as an HCl salt (0.78 g, 33%): mp 285–295° C.; IR (KBr): 2945, 1766 cm$^{-1}$; $^1$H NMR (500 MHz, DMSO-d$_6$): δ 11.47 (s, 1H), 8.81 (s, 2H), 7.68 (d, J=8 Hz, 2H), 7.49 (d, J=8 Hz, 2H), 7.17 (s, 1H), 7.20–6.97 (m, 2H), 3.10–3.02 (m, 1H), 2.98–2.91 (m, 2H), 2.80 (t, J=8 Hz, 2H), 2.57–2.50 (m, 1H), 2.18–2.11 (m, 2H), 2.01–1.95 (m, 2H), 1.90–1.84 (m, 2H), 1.51 (m, 4H); CI-MS (m/z): 419 [M+H]$^+$; HPLC: method A, 6.87 minutes (97.7%); Anal. Calcd for C$_{23}$H$_{25}$F$_3$N$_2$O$_2$.HCl: C, 60.73; H, 5.76; N, 6.16. Found: C, 60.63; H, 5.97; N, 6.04.

EXAMPLE 15

6-[trans-4-(2-Benzenesulfinylethylamino)cyclohexyl]-3H-benzoxazol-2-one

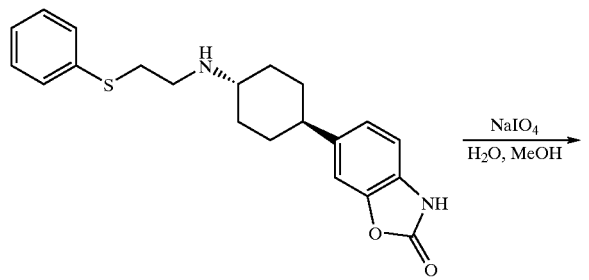

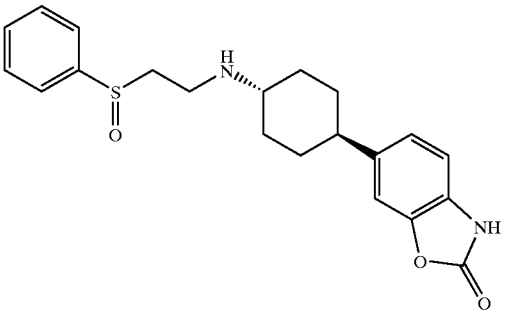

To a stirred, ice—Cold, suspension of NaIO$_4$ (0.13 g, 0.62 mmol) in H$_2$O (1.2 mL) was added 6-[trans-4-(2-phenylsulfanylethylamino)cyclohexyl]-3H-benzoxazol-2-one (0.25 g, 0.62 mmol). The viscous reaction mixture was diluted with H$_2$O (1.5 mL), warmed to room temperature, and then further diluted with MeOH (15 mL). After 21 hours, the reaction mixture was concentrated under reduced pressure. Purification by flash chromatography (silica, 89:10:1 CH$_2$Cl$_2$:MeOH:NH$_4$OH) gave the free base of 6-[trans-4-(2-benzenesulfinylethylamino)cyclohexyl]-3H-benzoxazol-2-one, which was converted to the HCl salt (0.13 g, 49%): mp 107–110° C.; IR (KBr): 2936, 2783, 1768, cm$^{-1}$; $^1$H NMR (500 MHz, DMSO-d$_6$): δ 9.03 (br s, 2H), 7.74–7.60 (m, 5H), 7.16 (s, 1H), 6.99–6.97 (m, 2H), 3.48–3.43 (m, 1H), 3.33–3.29 (m, 1H), 3.18–3.04 (m, 4H), 2.54–2.52 (m, 2H), 1.86–1.84 (m, 2H), 1.51–1.44 (m, 4H); API-MS (m/z): 385 [M+H]$^+$; HPLC: method A, 7.01 minutes (98.1%); method B, 12.83 minutes (99.2%); Anal. Calcd for C$_{21}$H$_{24}$N$_2$O$_3$S.HCl.1.25H$_2$O: C, 56.88; H, 6.25; N, 6.32. Found: C, 56.86; H, 6.18; N, 6.22.

EXAMPLE 16

6-[trans-4-(2-Benzenesulfonylethylamino)cyclohexyl]-3H-benzoxazol-2-one

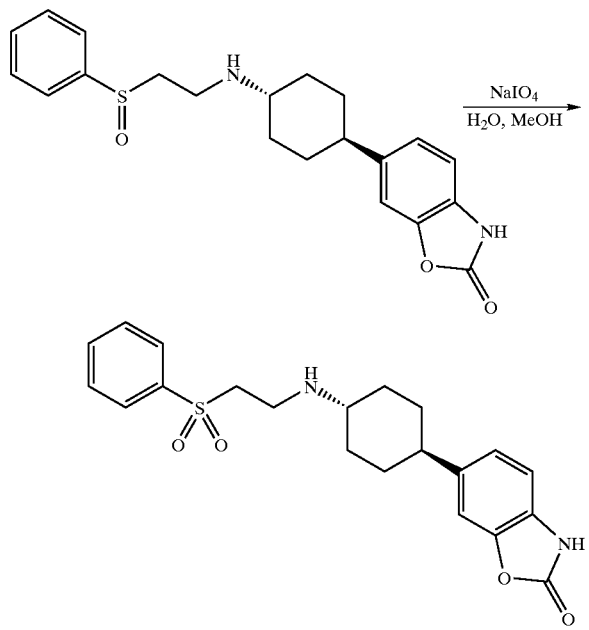

To a stirred suspension of NaIO$_4$ (0.30 g, 1.4 mmol) in a mixture of H$_2$O (5 mL) and MeOH (5 mL) was added 6-[trans-4-(2-phenylsulfanylethylamino)-cyclohexyl]-3H- benzoxazol-2-one (0.19 g, 0.47 mmol). After 48 hours, a second portion of NaIO₄ (0.20 g, 0.93 mmol) was added, and stirring was continued overnight. The reaction mixture was heated at 60° C. for 6 hours, then cooled to room temperature and concentrated under reduced pressure. The solids were suspended in a 2:1 mixture of MeOH and CH₂Cl₂ and the solution filtered. The filtrate was concentrated under reduced pressure. Purification by flash chromatography (silica, 50:49:1 acetone:CH₂Cl₂:MeOH) gave the free base 6-[trans-4-(2-benzenesulfonylethylamino)cyclohexyl]-3H-benzoxazol-2-one, which was converted to the HCl salt (0.050 g, 24%): mp 202–208° C.; IR (KBr): 3448, 2939, 1763 cm⁻¹; ¹H NMR (500 MHz, DMSO-d₆): δ 8.97 (br s, 2H), 7.98–7.71 (m, 5H), 7.16 (s, 1H), 6.99–6.98 (m, 2H), 3.77–3.74 (m, 1H), 3.25–3.23 (m, 1H), 3.21–3.20 (m, 4H), 2.09–2.04 (m, 2H), 1.90–1.40 (m, 2H), 1.52–1.40 (m, 4H); CI-MS (methane) (m/z): 401 [M+H]⁺; HRMS-API (m/z): [M+H]⁺ calcd for C₂₁H₂₄N₂O₄S, 401.1535; found, 401.1535; HPLC: method A, 6.34 minutes (97.3%); method B, 11.06 minutes (99.1%); Anal. Calcd for C₂₁H₂₄N₂O₄S.HCl.0.50H₂O: C, 56.56; H, 5.88; N, 6.28. Found: C, 56.29; H, 5.65; N, 6.13.

EXAMPLE 17

6-{trans-4-[Methyl(3-phenylpropyl)amino]cyclohexyl}-3H-benzoxazol-2-one

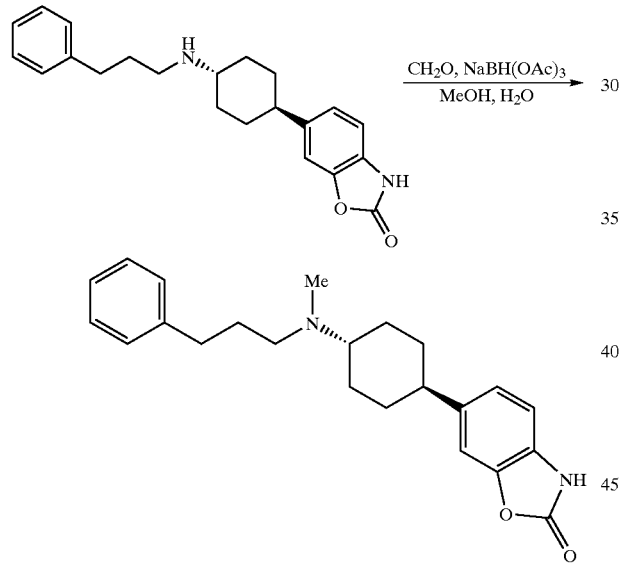

To a stirred solution of 6-[trans-4-(3-phenylpropylamino)cyclohexyl]-3H-benzoxazol-2-one (263 mg, 0.750 mmol) in MeOH (10 mL) was added H₂O (0.5 mL) and p-formaldehyde (113 mg, 3.75 mmol). After stirring the reaction mixture for 3 hours, NaBH(OAc)₃ was added, and stirring was continued for 12 hours. Solid NaOH was added to give a clear solution, which was then concentrated under reduced pressure. Purification by flash chromatography (silica, 95:4:1 CH₂Cl₂:MeOH:NH₄OH) gave 6-{trans-4-[methyl(3-phenylpropyl)-amino]cyclohexyl}-3H-benzoxazol-2-one (160 mg, 59%), as a white solid: mp 58–62° C.; IR (KBr): 2929, 1774 cm⁻¹; ¹H NMR (500 MHz, DMSO-d₆): δ 8.97 (br s, 1H), 7.26–7.12 (m, 6H), 6.99–6.98 (m, 2H), 2.63 (m, 2H), 2.57 (t, J=7 Hz, 2H), 2.56 (m, 1H), 2.38 (m, 2H), 2.18 (s, 3H), 1.78 (m, 2H), 1.68 (m, 2H), 1.37 (m, 2H), 1.27 (m, 2H); CI-MS (methane) (m/z): 365 [M+H]⁺; HRMS-API (m/z): [M+H]⁺ calcd for C₂₃H₂₈N₂O₂, 365.2229; found, 365.2231; HPLC: method A, 5.95 minutes (95.3%); method B, 10.12 minutes (97.6%); Anal. Calcd for C₂₃H₂₈N₂O₂.0.25H₂O: C, 74.87; H, 7.79; N, 7.59. Found: C, 74.77; H, 7.71; N, 7.81.

EXAMPLE 18

6-(trans-4-{[3-(4-Fluorophenyl)propyl]methylaamino}cyclohexyl)-3H-benzoxazol-2-one

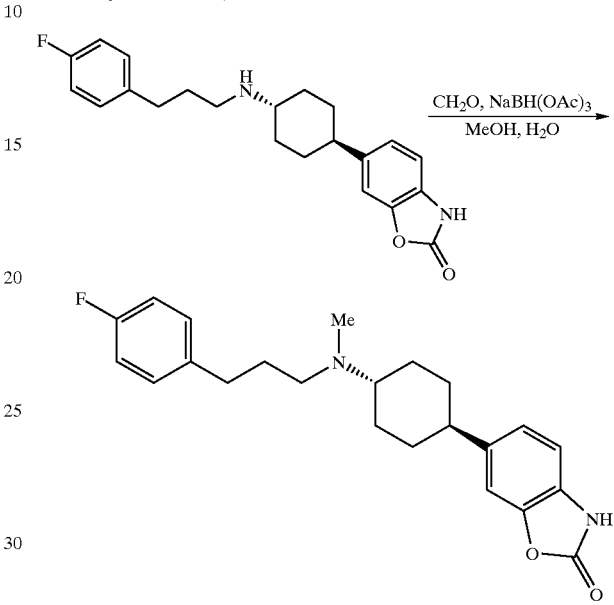

Coupling of 6-{trans-4-[3-(4-fluorophenyl)propylamino]cyclohexyl}-3H-benzoxazol-2-one (519 mg, 1.40 mmol) and p-formaldehyde (210 mg, 1.00 mmol), following the procedure described in Example 17, gave 6-(trans-4-{[3-(4-fluorophenyl)propyl]methylamino}cyclohexyl)-3H-benzoxazol-2-one (135 mg, 26%), as a white solid: mp 62–65° C.; IR (KBr): 2930, 1774, 1654, 1509 cm⁻¹; ¹H NMR (500 MHz, DMSO-d₆): δ 7.24–6.94 (m, 8H), 2.57 (m, 3H), 2.39 (m, 1H), 2.36 (m, 4H), 2.18 (s, 3H), 1.82 (m, 2H), 1.77 (m, 2H), 1.44 (m, 2H), 1.35 (m, 2H); CI-MS (methane) (m/z): 383 [M+H]⁺ HRMS-API (m/z): [M+H]⁺; calcd for C₂₃H₂₇FN₂O₂, 383.2135; found, 383.2133; HPLC: method A, 6.04 minutes (95.7%); method B, 10.73 minutes (96.8%); Anal. Calcd for C₂₃H₂₇FN₂O₂.0.75H₂O: C, 69.76; H, 7.25; N, 7.07. Found: C, 69.53; H, 6.97; N, 7.23.

EXAMPLE 19

6-(cis-4-{[3-(4-Fluorophenyl)propyl]methylamino}cyclohexyl)-3H-benzoxazol-2-one

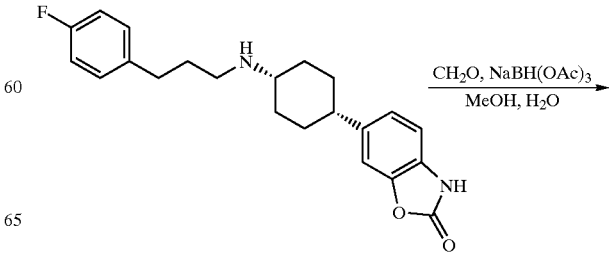

-continued

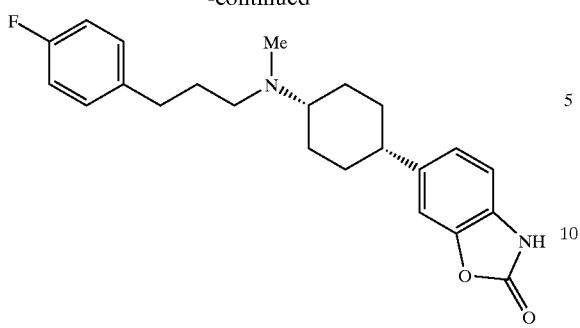

Coupling of 6-{cis-4-[3-(4-fluorophenyl)propylamino]-cyclohexyl}-3H-benzoxazol-2-one (519 mg, 1.40 mmol) and p-formaldehyde (210 mg, 1.00 mmol), following the procedure described in Example 17, gave 6-(cis-4-{[3-(4-fluorophenyl)propyl]methylamino}cyclohexyl)-3H-benzoxazol-2-one (600 mg, 78%), as an off-white glass: IR (KBr): 2944, 1770 cm$^{-1}$; $^1$H NMR (500 MHz, DMSO-d$_6$): δ 11.50 (s, 1H), 10.05 (s, 1H), 7.41 (s, 1H), 7.31–7.26 (m, 2H), 7.16–7.09 (m, 3H), 6.99 (d, J=8 Hz, 1H), 3.38–3.30 (m, 1H), 3.15–3.07 (m, 1H), 3.07–2.98 (m, 1H), 2.81–2.77 (m, 1H), 2.70 (d, J=5 Hz, 3H), 2.65–2.49 (m, 2H), 2.13–1.66 (m, 10H); ESI-MS (m/z): 383 [M+H]$^+$; HRMS-API (m/z): [M+H]$^+$ calcd for $C_{23}H_{27}FN_2O_2$, 383.2135; found, 383.2132; HPLC: method A, 5.88 minutes (98.7%); method B, 10.97 minutes (98.6%); Anal. Calcd for $C_{23}H_{27}FN_2O_2HCl.0.25H_2O$: C, 65.24; H, 6.78; N, 6.62. Found: C, 65.41; H, 6.97; N, 6.72.

EXAMPLE 20
6-{trans-4-[2-(4-Fluorophenylsulfanylethyl)methylamino]cyclohexyl}-3H-benzoxazol-2-one

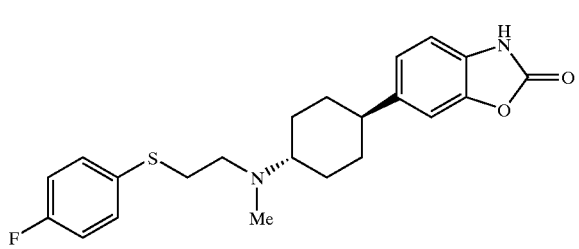

6-{trans-4-[2-(4-Fluorophenylsulfanyl)ethylamino]cyclohexyl}-3H-benzoxazol-2-one (197 mg, 0.51 mmol) was coupled with p-formaldehyde (76 mg, 2.5 mmol), following the procedure described in Example 17, except CH$_2$Cl$_2$ (5 mL) was added. Formation of the HCl salt gave 6-{trans-4-[2-(4-fluorophenylsulfanylethyl)methylamino]cyclohexyl}-3H-benzoxazol-2-one (154 mg, 69%), as a white solid: mp 213–217° C.; IR (KBr): 2942, 1770, 1492 cm$^{-1}$; $^1$H NMR (500 MHz, DMSO-d$_6$): δ 11.49 (s, 1H), 10.64 (br s, 1H), 7.56–7.51 (m, 2H), 7.25–7.21 (m, 2H), 7.14 (s, 1H), 7.00 (br s, 2H), 3.50–3.31 (m, 3H), 3.31–3.15 (m, 2H), 2.72 (d, J=5 Hz, 3H), 2.54–2.50 (m, 1H), 2.14–2.02 (m, 2H), 1.90–1.85 (m, 2H), 1.68–1.49 (m, 4H); CI-MS (methane) (m/z): 401 [M+H]$^+$; HPLC: method A, 5.95 minutes (98.1%); Anal. Calcd for $C_{22}H_{25}FN_2O_2S.HCl$ : C, 60.47; H, 6.00; N, 6.41. Found: C, 60.17; H, 6.00; N, 7.34.

EXAMPLE 21
6-{trans-4-[Methyl-3-(p-Tolylpropyl)amino]cyclohexyl}-3H-benzoxazol-2-one

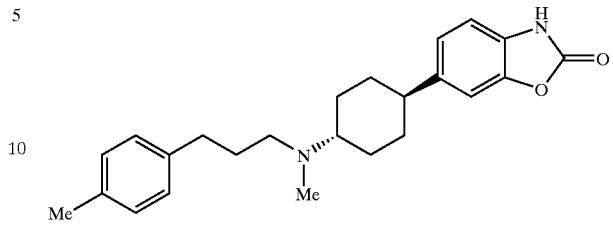

6-[trans-4-(3-p-Tolylpropylamino)cyclohexyl]-3H-benzoxazol-2-one (300 mg, 0.82 mmol) was coupled with p-formaldehyde (120 mg, 4.1 mmol) following the procedure described in Example 17 except CH$_2$Cl$_2$ (8 mL) was added. Also, additional NaBH(OAc)$_3$ and p-formaldehyde were added at intervals to drive the reaction to completion. Formation of the HCl salt gave 6-{trans4-[methyl-3-p-tolylpropyl)amino]cyclohexyl}-3H-benzoxazol-2-one (224 mg, 66%), as a white solid: mp 213–225° C.; IR (KBr): 2944, 1771, 1498, 1451 cm$^{-1}$; $^1$H NMR (500 MHz, DMSO-d$_6$): δ 11.48 (s, 1H), 9.85 (br s, 1H), 7.16–7.10 (m, 5H), 7.00 (br s, 2H), 3.32–3.26 (m, 1H), 3.19–3.11 (m, 1H), 3.04–2.97 (m, 1H), 2.70 (d, J=4 Hz, 3H), 2.65–2.50 (m, 3H), 2.28 (s, 3H), 2.12–2.02 (m, 2H), 2.02–1.94 (m, 2H), 1.94–1.88 (m, 2H), 1.68–1.50 (m, 4H); CI-MS (methane) (m/z): 379 [M+H]$^+$; calcd for $C_{24}H_{30}N_2O_2$, 379.2385; found, 379.2397; HPLC: method A, 6.45 minutes (99.4%); method B, 15.17 minutes (>99%); Anal. Calcd for $C_{24}H_{30}N_2O_2HCl.0.5H_2O$: C, 67.99; H, 7.61; N, 6.61. Found: C, 67.96; H, 7.57; N, 6.84.

EXAMPLE 22
6-{trans-4-[Methyl(2-phenoxyethyl)amino]cyclohexyl}-3H-benzoxazol-2-one

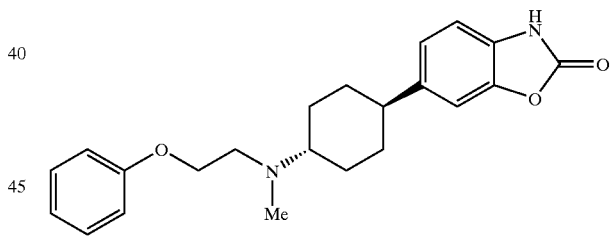

6-trans-[4-(2-Phenoxyethylamino)cyclohexyl]-3H-benzoxazol-2-one (250 mg, 0.71 mmol) was coupled with p-formaldehyde (100 mg, 3.5 mmol) following the procedure described in Example 17, except CH$_2$Cl$_2$ (10 mL) was added. Also, additional NaBH(OAc)$_3$ and NaBH$_4$ were added at intervals to drive the reaction to completion. Formation of the HCl salt gave 6-{trans-4-[methyl(2-phenoxyethyl)amino]cyclohexyl}-3H-benzoxazol-2-one (219 mg, 77%), as a white solid: mp 277–285° C.; IR (KBr): 2939, 1769, 1496 cm$^{-1}$; $^1$H NMR (500 MHz, DMSO-d$_6$): δ 11.48 (s, 1H), 10.00 (br s, 1H), 7.37–7.32 (m, 2H), 7.17 (s, 1H), 7.03–6.99 (m, 5H), 4.43–4.38 (m, 2H), 3.69–3.61 (m, 1H), 3.50–3.37 (m, 2H), 2.84 (d, J=4 Hz, 3H), 2.61–2.52 (m, 1H), 2.22–2.12 (m, 2H), 1.99–1.91 (m, 2H), 1.72–1.50 (m, 4H); CI-MS (methane) (m/z): 367 [M+H]$^+$; calcd for $C_{22}H_{26}N_2O_3$, 367.2021; found, 367.2018; HPLC: method A, 5.48 minutes (97.2%); method B, 12.81 minutes (98.0%); Anal. Calcd for $C_{22}H_{26}N_2O_3.HCl.0.1NH_4Cl$: C, 64.72; H, 6.76; N, 7.20. Found: C, 64.52; H, 6.86; N, 7.34.

EXAMPLE 23
6-{trans-4-[Methyl-3-(4-Trifluoromethylphenyl) propylamino]cyclohexyl}-3H-benzoxazol-2-one

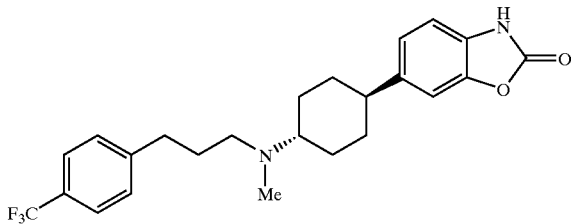

6-{trans-4-[3-(4-Trifluoromethylphenyl)propylamino] cyclohexyl}-3H-benzoxazol-2-one (200 mg, 0.48 mmol) was coupled with p-formaldehyde (72 mg, 2.4 mmol) following the procedure described in Example 17, except $CH_2Cl_2$ (5 mL) was added. Also, additional $NaBH(OAc)_3$ was added at intervals to drive the reaction to completion. Formation of the HCl salt gave 6-{trans-4-[methyl-3-(4-trifluoromethylphenyl)propylamino]cyclohexyl}-3H-benzoxazol-2-one (175 mg, 77%), as a white solid: mp 227–234° C.; IR (KBr): 2945, 1771, 1497 cm$^{-1}$; $^1$H NMR (500 MHz, DMSO-d$_6$): δ 11.48 (s, 1H), 10.00 (br s, 1H), 7.68 (d, J=8 Hz, 2H), 7.50 (d, J=8 Hz, 2H), 7.16 (s, 1H), 6.99 (s, 2H), 3.33–3.29 (m, 1H), 3.22–3.14 (m, 1H), 3.08–3.00 (m, 1H), 2.81–2.72 (m, 2H), 2.71 (d, J=5 Hz, 3H), 2.59–2.51 (m, 1H), 2.15–2.05 (m, 4H), 1.94–1.88 (m, 2H), 1.68–1.51 (m, 4H); CI-MS (methane) (m/z): 433 [M+H]$^+$; calcd for $C_{24}H_{27}F_3N_2O_2$, 433.2103; found, 433.2105; HPLC: method C, 14.09 minutes (95.8%); method D, 15.99 minutes (97.3%); Anal. Calcd for $C_{24}H_{27}F_3N_2O_2 \cdot HCl \cdot H_2O$: C, 59.20; H, 6.21; N, 5.75. Found: C, 59.22; H, 6.22; N, 5.55.

EXAMPLE 24
(a) 6-{trans-4-[3-(2,4-Difluorophenyl)propylamino] cyclohexyl}-3H-benzoxazol-2-one
(b) 6-(trans-4-{[3-(2,4-Difluorophenyl)propyl] methylamino}cyclohexyl)-3H-benzoxazol-2-one

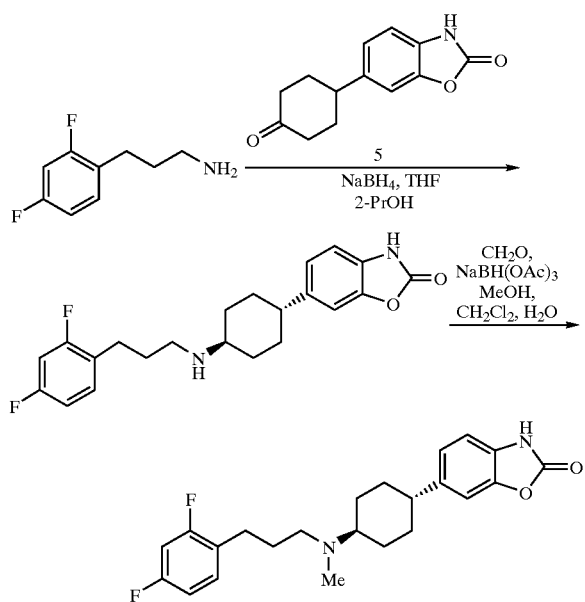

Coupling of ketone 5 and 3-(2,4-difluorophenyl)-1-propylamine, using the method given in Example 1, gave (a) 6-{trans-4-[3-(2,4-difluorophenyl)-propylamino]-cyclohexyl}-3H-benzoxazol-2-one and (0.75 g, 37%), isolated as the HCl salt: $^1$H NMR (500 MHz, DMSO-d$_6$): δ 11.49 (s, 1H), 8.84 (br s, 2H), 7.40 (ddd, J=9, 9, 7 Hz, 1H), 7.22–7.18 (m, 2H), 7.05 (ddd, J=8, 8, 2 Hz, 1H), 7.01 (dd, J=8, 1 Hz, 1H), 6.99 (d, J=8 Hz, 1H), 3.11–3.02 (m, 1H), 2.98–2.92 (m, 2H), 2.70 (t, J=8 Hz, 2H), 2.56–2.49 (m, 1H), 2.18–2.11 (m, 2H), 1.96–1.86 (m, 4H), 1.51 (m, 4H), and (b) 6-{trans-4-[3-(2,4-Difluorophenyl)propylamino] cyclohexyl}-3H-benzoxazol-2-one and (435 mg, 1.0 mmol) was coupled with p-formaldehyde (150 mg, 5.1 mmol) following the procedure described in Example 17, except $CH_2Cl_2$ (15 mL) was added. Also, additional $NaBH(OAc)_3$ was added at intervals to drive the reaction to completion. Formation of the HCl salt gave (b) 6-(trans-4-{[3-(2,4-difluorophenyl)propyl] methylamino}cyclohexyl)-3H-benzoxazol-2-one (314 mg, 72%), as a white solid: mp 269–272° C.; IR (KBr): 2947, 1768 cm$^{-1}$; $^1$H NMR (500 MHz, DMSO-d$_6$): δ 11.50 (s, 1H), 10.37 (br s, 1H), 7.41 (ddd, J=8, 8, 7 Hz, 1H), 7.22–7.16 (m, 2H), 7.07–7.04 (m, 1H), 7.00 (s, 2H), 3.32–3.28 (m, 1H), 3.20–3.12 (m, 1H), 3.08–2.99 (m, 1H), 2.72–2.61 (m, 5H), 2.59–2.50 (m, 1H), 2.15–2.07 (m, 2H), 2.04–1.96 (m, 2H), 1.90–1.89 (m, 2H), 167–1.51 (m, 4H); ESI-MS (m/z): 401 [M+H]$^+$; HPLC: method A, 5.96 minutes (>99%); Anal. Calcd for $C_{23}H_{26}F_2N_2O_2 \cdot HCl$: C, 63.23; H, 6.23; N, 6.41. Found: C, 63.03; H, 6.16; N, 6.25.

EXAMPLE 25
6-(trans-4-{Ethyl-[3-(4-fluorophenyl)propyl] amino}cyclohexyl)-3H-benzoxazol-2-one

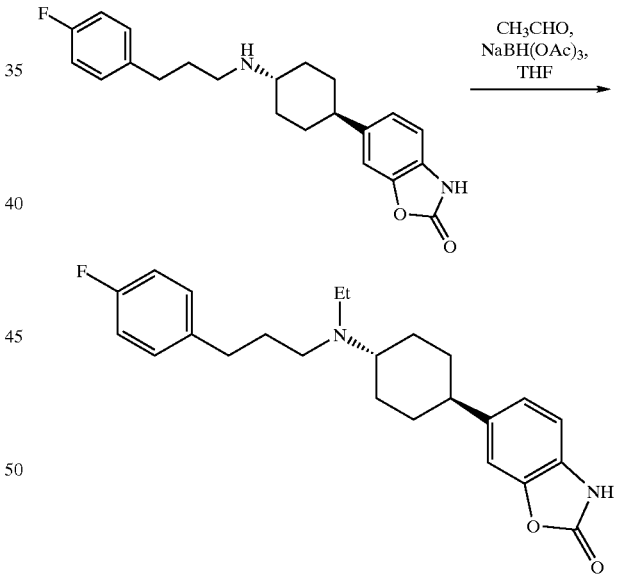

To a stirred solution of 6-{trans-4-[3-(4-fluorophenyl)-propylamino]-cyclohexyl}-3H-benzoxazol-2-one (1.0 g, 2.7 mmol) in THF (60 mL) was added acetaldehyde (240 mg, 5.4 mmol) and 3 Å molecular sieves. After stirring the reaction mixture for 5 to 10 minutes, $NaBH(OAc)_3$ (0.81 mg, 3.8 mmol) was added, and stirring was continued for 0.5 hours. The reaction mixture was concentrated under reduced pressure, and the residue was dissolved in MeOH. The solution was brought to pH=10 with 2N NaOH, filtered through Celite, and concentrated under reduced pressure. Purification by flash chromatography (silica, 89:10:1 $CH_2Cl_2$:MeOH:NH$_4$OH), followed by formation of the HCl salt gave 6-(trans-4-{[ethyl-[3-(4-fluorophenyl)propyl]amino}-cyclohexyl)-3H-benzoxazol-2-one (395 mg, 33%), as a white solid: mp 228–231° C.; IR (KBr): 2946, 1769, 1509 cm$^{-1}$; $^1$H NMR (500 MHz, DMSO-d$_6$): δ 11.47 (s, 1H), 9.65 (br s, 1H), 7.33–7.29 (m, 2H), 7.17–7.12 (m, 3H), 7.00 (s, 2H), 3.39–3.32 (m, 1H), 3.24–3.08 (m, 3H), 3.05–2.98 (m, 1H), 2.68 (q, J=7, 3 Hz, 2H), 2.60–2.50 (m, 1H), 2.14–2.09 (m, 2H), 2.04–1.98 (m, 2H), 1.93–1.87 (m, 2H), 1.69–1.55 (m, 4H), 1.26 (t, J=7 Hz, 3H); CI-MS (methane) (m/z): 397 [M+H]$^+$; HPLC: method A, 6.37 minutes (97.7%); Anal. Calcd for C$_{24}$H$_{29}$FN$_2$O$_2$.HCl: C, 66.58; H, 6.98; N, 6.47. Found: C, 66.37; H, 7.08; N, 6.25.

EXAMPLE 26
6-(trans-4-{[Ethyl-[3-(4-fluorophenyl)propyl]amino}cyclohexyl)-3H-benzoxazol-2-one

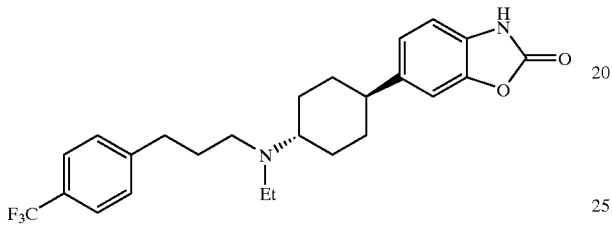

Coupling of 6-{trans-4-[3-(4-trifluoromethylphenyl)propylamino]-cyclohexyl}-3H-benzoxazol-2-one (200 mg, 0.48 mmol) and acetaldehyde (42 mg, 0.96 mmol) following the procedure described in Example 24, followed by formation of the HCl salt, gave 6-(trans-4-{[ethyl-[3-(4-fluorophenyl)-propyl]amino}cyclohexyl)-3H-benzoxazol-2-one (80 mg, 35%), as an off-white solid: mp 248–252° C.; IR (KBr): 2946, 1771, 1497, 1451 cm$^{-1}$; $^1$H NMR (500 MHz, DMSO-d$_6$): δ 11.49 (s, 1H), 9.81 (br s, 1H), 7.68 (d, J=8 Hz, 2H), 7.51 (d, J=8 Hz, 2H), 7.16 (s, 1H), 7.00 (s, 1H), 3.40–3.31 (m, 1H), 3.27–3.09 (m, 3H), 3.09–2.99 (m, 1H), 2.77 (q, J=7,3 Hz, 2H), 2.59–2.50 (m, 1H), 2.15–2.00 (m, 4H), 1.92–1.88 (m, 2H), 1.69–1.54 (m, 4H), 1.27 (t, J=7 Hz, 3H); CI-MS (methane) (m/z): 447 [M+H]$^+$; calcd for C$_{25}$H$_{29}$F$_3$N$_2$O$_2$, 447.2259; found, 447.2267; HPLC: method, C, 14.40 minutes (98.3%); method D, 16.11 minutes (98.5%); Anal. Calcd for C$_{25}$H$_{29}$F$_3$N$_2$O$_2$.HCl 0.25H$_2$O: C, 61.60; H. 6.31; N, 5.75. Found: C, 61.59; H, 6.22; N, 5.58.

EXAMPLE 27
6-(trans-4-{Ethyl-[(R)-1-methyl-3-phenylpropyl]amino}cyclohexyl)-3H-benzoxazol-2-one

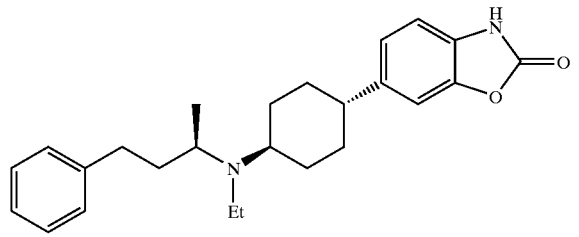

Coupling of 6-{trans-4-[(R)-1-methyl-3-phenylpropylamino]cyclohexyl}-3H-benzoxazol-2-one (370 mg, 1.01 mmol) and acetaldehyde (44 mg, 1.01 mmol) following the procedure described in Example 24, followed by formation of the HCl salt, gave 6-(trans-4-{ethyl-[(R)-1-methyl-3-phenylpropyl]amino}-cyclohexyl)-3H-benzoxazol-2-one (70 mg, 25%), as a pale yellow solid (a mixture of diastereomers): mp 139–158° C.; IR (KBr): 2941, 1772, 1497, 1451 cm$^{-1}$; $^1$H NMR (500 MHz, DMSO-d$_6$): δ 11.52 (s, 2H), 9.11 (s, 2H), 7.35–7.21 (m, 10H), 7.18 (m, 4H), 7.00 (s, 2H), 3.20 (m, 2H), 2.81 (m, 2H), 2.54 (m, 2H), 2.20–1.51 (m, 28H), 1.44 (d, J=7 Hz, 3H), 1.32 (d, J=7 Hz, 3H), 1.26 (m, 6H); API-MS (methane) (m/z): 393 [M+H]$^+$; calcd for C$_{25}$H$_{32}$N$_2$O$_2$, 393.2542; found, 393.2540; HPLC: method C, 5.77 minutes (97.4%), method D, 11.47 minutes and 11.57 minutes (98.1%); Anal. Calcd for C$_{25}$H$_{32}$N$_2$O$_2$HCl.0.5H$_2$O: C, 68.55; H, 7.82; N, 6.40. Found: C, 68.67; H, 8.03; N, 6.27.

EXAMPLE 28
6-(trans-4-{Ethyl-[(S)-1-methyl-3-phenylpropyl]amino}cyclohexyl)-3H-benzoxazol-2-one

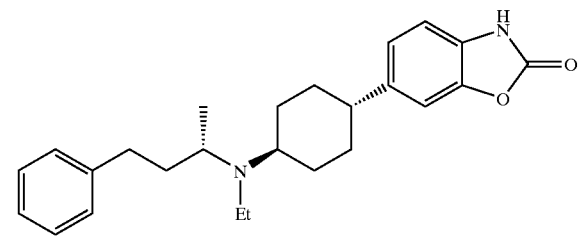

Coupling of 6-{trans-4-[(S)-1-methyl-3-phenylpropylamino]cyclohexyl}-3H-benzoxazol-2-one (196 mg, 0.538 mmol) and acetaldehyde (24 mg, 0.538 mmol) following the procedure described in Example 24, followed by formation of the HCl salt, gave 6-(trans-4-{ethyl-[(S)-1-methyl-3-phenylpropyl]-amino}cyclohexyl)-3H-benzoxazol-2-one (110 mg, 50%), as a pale yellow solid (a mixture of diastereomers): mp 221–246° C.; IR (KBr): 3424, 2929, 1771, 1495 cm$^{-1}$; $^1$H NMR (500 MHz, DMSO-d$_6$): δ 11.52 (s, 2H), 9.11 (s, 2H), 7.35–7.21 (m, 10H), 7.18 (m, 4H), 7.00 (s, 2H), 3.20 (m, 2H), 2.81 (m, 2H), 2.54 (m, 2H), 2.20–1.51 (m, 28H), 1.44 (d, J=7 Hz, 3H), 1.32 (d, J=7 Hz, 3H), 126 (m, 6H); API-MS (methane) (m/z): 393 [M+H]$^+$; HPLC: method C, 5.88 minutes (97.4%), method D, 11.32 minutes (>99%); Anal. Calcd for C$_{25}$H$_{32}$N$_2$O$_2$.HCl.H$_2$O: C, 67.17; H, 7.89; N, 6.27. Found: C, 67.18; H, 7.69; N, 5.98.

EXAMPLE 29
6-{trans-4-[[3-(4-Fluorophenyl)propyl]-(2-hydroxyethyl)amino]cyclohexyl}-3H-benzoxazol-2-one

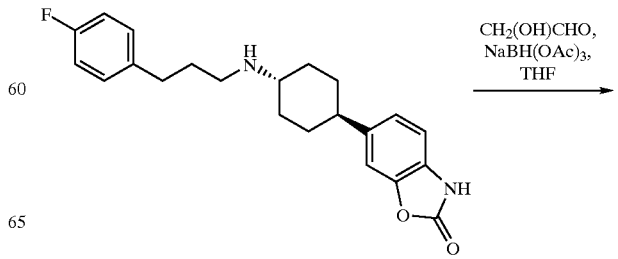

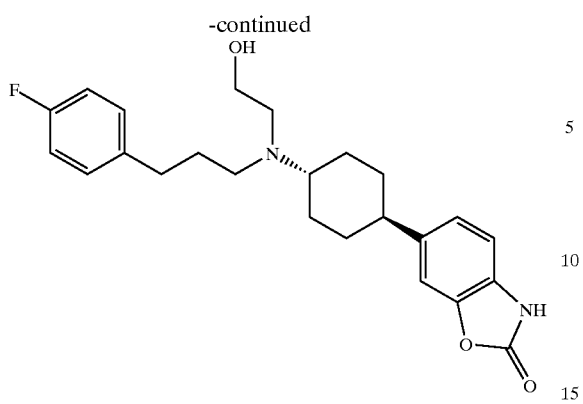

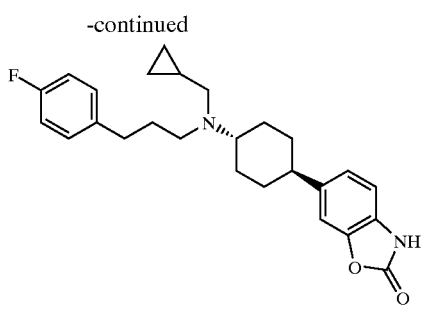

To a stirred solution of 6-{trans-4-[3-(4-fluorophenyl)propylamino]-cyclohexyl}-3H-benzoxazol-2-one (0.5 g, 1.2 mmol) in THF (25 mL) and CH$_2$Cl$_2$ (5 mL) was added Et$_3$N (0.17 mL, 1.2 mmol), glycoaldehyde (110 mg, 1.8 mmol), and 3 Å molecular sieves. After stirring the reaction mixture for 5 to 10 minutes, NaBH(OAc)$_3$ was added, and stirring was continued for 0.5 hours. The reaction mixture was concentrated under reduced pressure, and the residue was dissolved in MeOH. The solution was brought to pH=11 with 2N NaOH, filtered through Celite, and concentrated under reduced pressure. Purification by flash chromatography (silica, 90:9.5:0.5 CH$_2$Cl$_2$:MeOH:NH$_4$OH) and (silica, 90:10 CH$_2$Cl$_2$:MeOH) resulted in isolation of the free base (120 mg, 24%). Formation of the HCl salt gave compound 6-{trans-4-[[3-(4-fluorophenyl)-propyl]-(2-hydroxyethyl)amino]cyclohexyl}-3H-benzoxazol-2-one as a white solid: mp 259–262° C.; IR (KBr): 3314, 2949, 1765, 1509cm$^{-1}$; $^1$H NMR (500 MHz, DMSO-d$_6$): δ 11.50 (s, 1H), 9.40 (br s, 1H), 7.32–7.28 (m, 2H), 7.18–7.12 (m, 3H), 7.00 (s, 2H), 5.34–5.31 (m, 1H), 3.76–3.74 (m, 2H), 3.49–3.39 (m, 1H), 3.21–3.08 (m, 3H), 2.65 (t, J=8 Hz, 2H), 2.60–2.49 (m, 2H), 2.18–1.99 (m, 4H), 1.98–1.86 (m, 2H), 1.71–1.52 (m, 4H); API-MS (methane) (m/z): 413 [M+H]$^+$; calcd for C$_{24}$H$_{29}$FN$_2$O$_3$, 413.2240; found, 413.2239; HPLC: method A, 5.47 minutes (98.9%); method B, 11.11 minutes (98.5%); Anal. Calcd for C$_{24}$H$_{29}$FN$_2$O$_3$.HCl.0.5H$_2$O: C, 62.94; H, 6.82; N, 6.12. Found: C, 63.10; H, 6.67; N, 6.06.

EXAMPLE 30

6-(trans-4-{Cyclopropylmethyl-[3-(4-fluorophenyl)propyl]amino}cyclohexyl)-3H-benzoxazol-2-one The free base of 6-{trans-4-[3-(4-fluorophenyl)propylamino]cyclohexyl}-3H-benzoxazol-2-one (400 mg, 0.99 mmol) was made by the addition of 1N NaOH (0.99 mL, 0.99 mmol) to 6-{trans-4-[3-(4-fluorophenyl)propylamino]-cyclohexyl}-3H-benzoxazol-2-one hydrochloride in THF (25 mL) and MeOH (10 mL). Cyclopropanecarboxaldehyde (70 mg, 0.99 mmol) was added, followed by NaBH(OAc)$_3$ (300 mg, 1.4 mmol). Additional NaBH(OAc)$_3$ and cyclopropanecarboxaldehyde were added at intervals, over 28 hours, to drive the reaction to completion. The solution was brought to pH=11 with solid NaOH and then concentrated under reduced pressure. Purification by flash chromatography (silica, 90:9.5:0.5 CH$_2$Cl$_2$:MeOH:NH$_4$OH) followed by formation of the HCl salt gave 6-(trans-4-{cyclopropylmethyl-[3-(4-fluorophenyl)propyl]amino}-cyclohexyl)-3H-benzoxazol-2-one (347 mg, 76%), as a white solid: mp 221–225° C.; IR (KBr): 2937, 1764, 1510 cm$^{-1}$; $^1$H NMR (500 MHz, DMSO-d$_6$): δ 11.50 (s, 1H), 9.78 (br s, 1H), 7.33–7.29 (m, 2H), 7.18–7.12 (m, 3H), 7.02 (s, 2H), 3.50–3.42 (m, 1H), 3.24–2.97 (m, 4H), 2.72–2.61 (m, 2H), 2.59–2.55 (m, 1H), 2.18–2.01 (m, 4H), 1.94–1.88 (m, 2H), 1.69–1.53 (m, 4H), 1.18–1.09 (m, 1H), 0.68–0.59 (m, 2H), 0.46–0.36 (m, 2H); ESI-MS (m/z): 423 [M+H]$^+$; HPLC: method A, 6.22 minutes (98.5%); Anal. Calcd for C$_{26}$H$_{31}$FN$_2$O$_2$.HCl: C, 68.04; H, 7.03; N, 6.10. Found: C, 67.65; H, 7.07; N, 5.95.

EXAMPLE 31

6-(trans-4-{[3-(4-Fluorophenyl)propyl]furan-3-ylmethylamino}cyclohexyl)-3H-benzoxazol-2-one

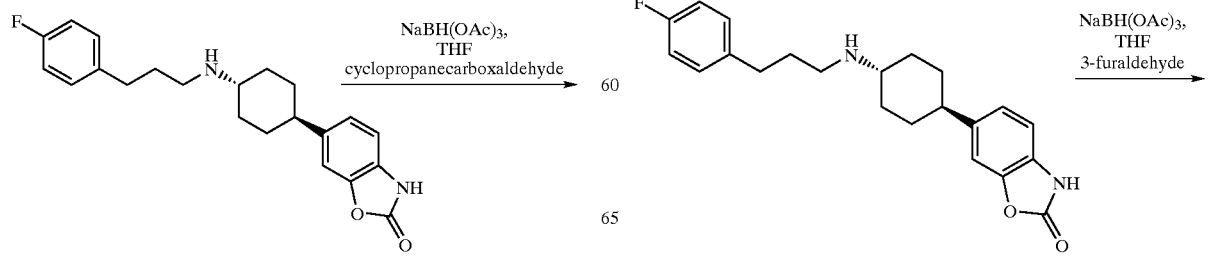

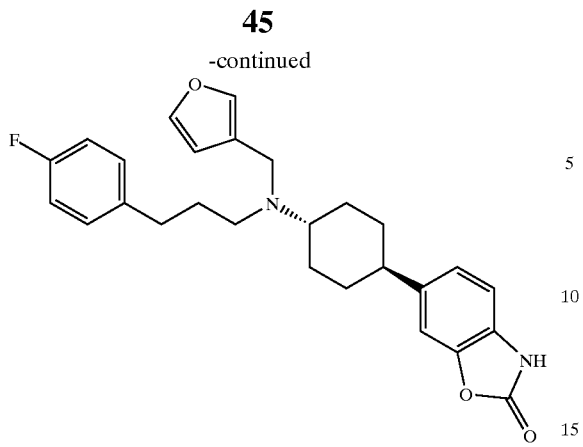

The free base of 6-{trans-4-[3-(4-fluorophenyl) propylamino]cyclohexyl}-3H-benzoxazol-2-one was made by the addition of $K_2CO_3$ (170 mg, 1.2 mmol) to 6-{trans-4-[3-(4-fluorophenyl)propylamino]cyclohexyl}-3H-benzoxazol-2-one hydrochloride (500 mg, 1.2 mmol) in THF (50 mL). To this suspension was added 3-furaldehyde (470 mg, 4.9 mmol) and, after 10 minutes, $NaBH(OAc)_3$ (520 mg, 2.4 mmol) was added. After stirring the reaction mixture 3 hours, additional $NaBH(OAc)_3$ (520 mg, 2.4 mmol) was added, and stirring continued for 14.5 hours. The solution was diluted with MeOH and brought to pH=13 with solid NaOH. The solution was then concentrated under reduced pressure. Purification by flash chromatography (silica, 90:9.5:0.5 $CH_2Cl_2$:MeOH:$NH_4OH$), followed by formation of the HCl salt, gave 6-(trans-4-{[3-(4-fluorophenyl)-propyl]furan-3-ylmethylamino}cyclohexyl)-3H-benzoxazol-2-one (272 mg, 46%) as an off-white solid: mp 225–227° C.; IR (KBr): 2929, 1773, 1510 $cm^{-1}$; $^1H$ NMR (500 MHz, DMSO-$d_6$): δ 11.49 (s, 1H), 9.99 (br s, 1H), 7.90 (s, 1H), 7.76 (s, 1H), 7.27–7.24 (m, 2H), 7.18 (s, 1H), 7.14–7.10 (m, 2H), 7.02–6.98 (m, 2H), 6.75 (s, 1H), 4.30–4.18 (m, 2H), 3.33–3.29 (m, 1H), 3.20–3.12 (m, 1H), 3.01–2.93 (m, 1H), 2.67–2.53 (m, 3H), 2.22–2.15 (m, 2H), 2.07–1.88 (m, 4H), 1.78–1.66 (m, 2H), 1.62–1.49 (m, 2H); ESI-MS (m/z): 449 [M+H]$^+$; HPLC: method A, 6.27 minutes (99.8%); Anal. Calcd for $C_{27}H_{29}FN_2O_3$·HCl: C, 66.87; H, 6.23; N, 5.78. Found: C, 66.54; H, 6.27; N, 5.48.

To a stirred suspension of 6-{trans-4-[3-(4-fluorophenyl)-propylamino]-cyclohexyl}-3H-benzoxazol-2-one (400 mg, 0.99 mmol) in THF (40 mL) and DMF (3 mL) was added $NaHCO_3$ (180 mg, 2.2 mmol) and allyl bromide (130 mg, 1.1 mmol). After refluxing overnight, additional DMF (1.5 mL), allyl bromide (30 mg, 29 mmoL), and $NaHCO_3$ (21 mg, 0.25 mmol) were added. The reaction mixture was refluxed for 12 hours and then cooled to room temperature. The material was diluted with water and extracted with EtOAc (3x). The combined organics were washed with water, saturated NaCl solution (3x), dried ($Na_2SO_4$), filtered, and concentrated under reduced pressure. Purification by flash chromatography (silica, 90:10 $CH_2Cl_2$:MeOH), followed by formation of the HCl salt, gave 6-(trans-4-{allyl-[3-(4-fluorophenyl)propyl]-amino}cyclohexyl)-3H-benzoxazol-2-one (138 mg, 31%), as a white solid: mp 224–230° C.; IR (KBr): 2943, 1770, 1510 $cm^{-1}$; $^1H$ NMR (500 MHz, DMSO-$d_6$): δ 11.51 (s, 1H), 10.38 (br s, 1H), 7.31–7.28 (m, 2H), 7.17–7.11 (m, 3H), 7.00 (s, 2H), 6.11–6.04 (m, 1H), 5.55 (d, J=17 Hz, 1H), 5.45 (d, J=10 Hz, 1H), 3.87–3.71 (m, 2H), 3.38–3.31 (m, 1H), 3.19–3.13 (m, 1H), 3.05–2.92 (m, 1H), 2.70–2.51 (m, 3H), 2.18–2.12 (m, 2H), 2.07–1.99 (m, 2H), 1.92–1.87 (m, 2H), 1.72–1.50 (m, 4H); (ESI-MS (m/z): 409 [M+H]$^+$; HPLC: method B, 11.34 minutes (98.1%); Anal. Calcd for $C_{25}H_{29}FN_2O_2$·HCl: C, 67.48; H, 6.80; N, 6.30. Found: C, 67.29; H, 6.93; N, 6.07.

EXAMPLE 32

6-(trans-4-{Allyl-[3-(4-fluorophenyl)propyl] amino}cyclohexyl)-3H-benzoxazol-2-one

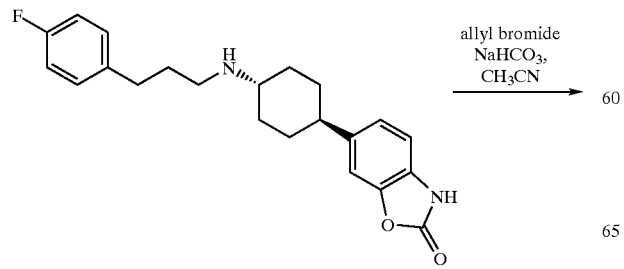

EXAMPLE 33

6-(trans-4-{[3-(4-Fluorophenyl)propyl] isobutylamino}cyclohexyl)-3H-benzoxazol-2-one

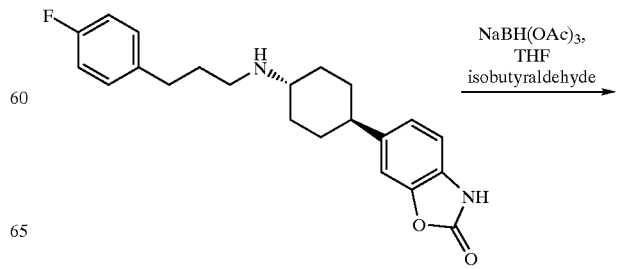

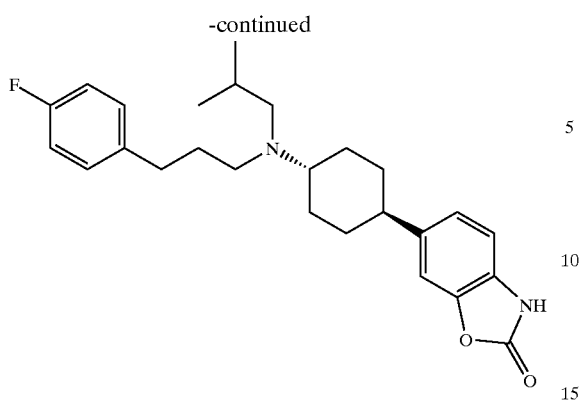
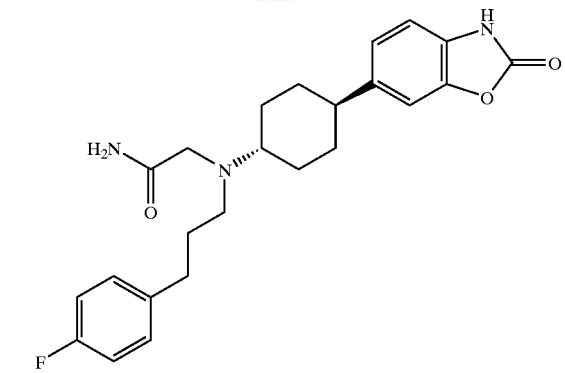

The free base of 6-{trans-4-[3-(4-fluorophenyl)-propylamino]cyclohexyl}-3H-benzoxazol-2-one was made by the addition of K$_2$CO$_3$ (140 mg, 1.0 mmol) to 6-{trans-4-[3-(4-fluorophenyl)propylamino]-cyclohexyl}-3H-benzoxazol-2-one hydrochloride (400 mg, 1.0 mmol) in THF (40 mL). The solution was warmed to dissolve the free base and then cooled to room temperature. Isobutyraldehyde (280 mg, 4.0 mmol) was added, followed by NaBH(OAc)$_3$ (420 mg, 2.0 mmol) after 10 minutes. The reaction mixture was stirred for 2.5 days and then concentrated under reduced pressure. The solution was diluted with MeOH and brought to pH=10 with solid NaOH. The solution was then concentrated under reduced pressure. Purification by flash chromatography (silica, 95:4.75:0.25 CH$_2$Cl$_2$:MeOH:NH$_4$OH), followed by formation of the HCl salt, gave 6-(trans-4-{[3-(4-fluorophenyl)propyl]-isobutylamino}cyclohexyl)-3H-benzoxazol-2-one (327 mg, 46%), as a white solid: mp 199–201° C.; IR (KBr): 2941, 1769, 1510 cm$^{-1}$; $^1$H NMR (500 MHz, DMSO-d$_6$): δ 11.51 (s, 1H), 9.16 (brs, 1H), 7.32–7.29 (m, 2H), 7.17–7.12 (m, 3H), 6.99 (s, 2H), 3.38–3.33 (m, 1H), 3.13–3.03 (m, 3H), 2.86–2.80 (m, 1H), 2.66–2.62 (m, 2H), 2.58–2.51 (m, 1H), 2.13–1.97 (m, 5H), 1.92–1.87 (m, 2H), 1.74–1.56 (m, 4H), 1.02–0.98 (m, 6H); ESI-MS (m/z): 425 [M+H]$^+$; HPLC: method A, 6.38 minutes (98.7%); Anal. Calcd for C$_{26}$H$_{33}$FN$_2$O$_2$.HCl: C, 67.74; H, 7.43; N, 6.08. Found: C, 67.65; H, 7.29; N, 5.93.

To a stirred suspension of 6-{trans-4-[3-(4-fluorophenyl)propylamino]-cyclohexyl}-3H-benzoxazol-2-one (110 mg, 0.81 mmol) in DMF (15 mL) was added NaHCO$_3$ (140 mg, 1.6 mmol) and bromoacetamide (300 mg, 0.74 mmol). After 16 hours the reaction mixture was warmed to 50° C. After 4 hours, additional bromide (150 mg, 0.37 mmol) and NaHCO$_3$ (31 mg, 0.37 mmol) were added, and the temperature increased to 75° C. After 4 hours, the reaction mixture was cooled to room temperature, diluted with water and extracted with EtOAc. The combined organics were washed with water, saturated NaCl, dried (Na$_2$SO$_4$), filtered, and concentrated under reduced pressure. Purification by flash chromatography (silica, 95:4.75:0.25 CH$_2$Cl$_2$:MeOH:NH$_4$OH) followed by conversion to the HCl salt gave compound 2-{[3-(4-fluorophenyl)propyl]-[4-(2-oxo-2,3-dihydro-benzoxazol-6-yl)-cyclohexyl]amino}acetamide (60 mg, 17%), as a white solid: mp 266–270° C.; IR (KBr): 3331, 3149, 2943, 1762, 1691 cm$^{-1}$; $^1$H NMR (500 MHz, DMSO-d$_6$): δ 11.47 (s, 1H), 9.08 (br s, 1H), 7.96 (br s, 1H), 7.73 (br s, 1H), 7.29–7.25 (m, 2H), 7.17–7.01 (m, 3H), 6.99 (s, 2H), 4.05–4.02 (m, 1H), 3.81–3.78 (m, 1H), 3.47–3.38 (m, 1H), 3.22–3.12 (m, 3H), 2.63 (t, J=8 Hz, 2H), 2.57–2.52 (m, 1H), 2.14–1.87 (m, 6H), 1.71–1.49 (m, 4H); ESI-MS (m/z): 426 [M+H]$^+$; HPLC: method A, 5.44 minutes (98.0%); HPLC: method E, 6.50 minutes (>99%); Anal. Calcd for C$_{24}$H$_{28}$FN$_3$O$_3$.HCl: C, 61.80; H, 6.37; N, 9.01. Found: C, 61.78; H, 6.27; N, 8.80.

EXAMPLE 35

6-(trans-4-{(2-Aminoethyl)-[3-(4-fluorophenyl)propyl]amino}cyclohexyl)-3H-benzoxazol-2-one

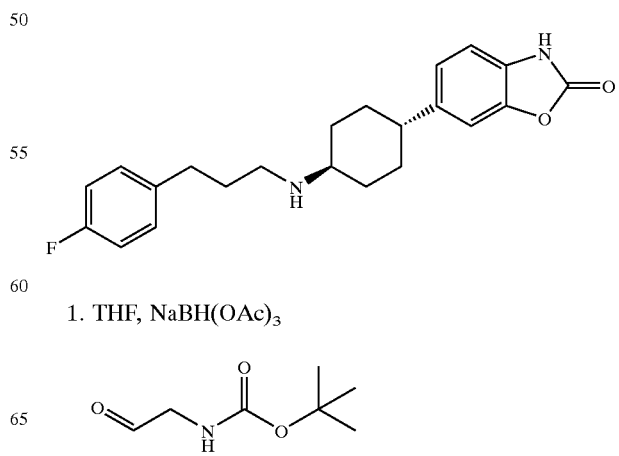

EXAMPLE 34

2-{[3-(4-Fluorophenyl)propyl]-[4-(2-oxo-2,3-dihydro-benzoxazol-6-yl)-cyclohexyl]amino}acetamide

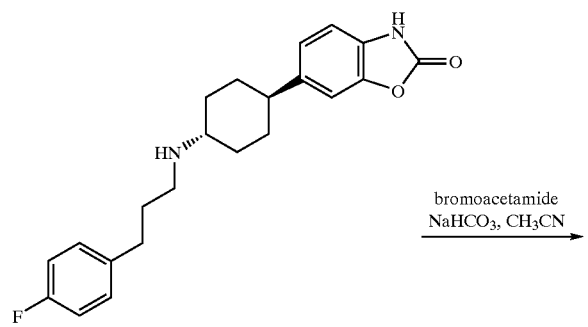

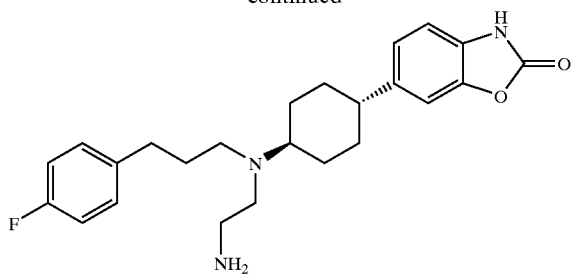

2. dioxane, HCl

To a stirred solution of 6-{trans-4-[3-(4-fluorophenyl)propylamino]-cyclohexyl}-3H-benzoxazol-2-one (HCl salt) (0.5 g, 1.2 mmol) in THF (25 mL) was added Et$_3$N (0.19 mL, 1.4 mmol), tert-butyl N-(2-oxoethyl)carbamate (220 mg, 1.9 mmol) and 3 Å molecular sieves. After stirring the reaction mixture for 10 minutes, NaBH(OAc)$_3$ (0.43 g, 0.39 mmol) was added, and stirring was continued for 5.75 hours. The reaction mixture was diluted with MeOH, brought to pH=8 with 1N NaOH, filtered, and concentrated under reduced pressure. Purification by flash chromatography (silica, 95:5 CH$_2$Cl$_2$:MeOH) gave 220 mg of Boc protected amine. The residue was dissolved in dioxane (12 mL), and 4 M HCl in dioxane (2 mL) was added. The mixture was stirred for 2 hours, concentrated under reduced pressure, and purified by flash chromatography (silica, 89:10:1 CH$_2$Cl$_2$:MeOH:NH$_4$OH). Formation of the HCl salt gave 6-(trans-4-{(2-aminoethyl)-[3-(4-fluorophenyl)propyl]amino}cyclohexyl)-3H-benzoxazol-2-one (133 mg, 27%), as a white solid: mp 161–169° C.; IR (KBr): 2929, 1764, 1656 cm$^{-1}$; $^1$H NMR (500 MHz, DMSO-d$_6$): δ 7.24–7.22 (m, 2H), 7.10–7.06 (m, 3H), 6.95–6.90 (m, 2H), 3.50–3.10 (br s, 3H), 2.60–2.41 (m, 10H), 1.83–1.76 (m, 4H), 1.79–1.63 (m, 2H), 1.49–1.31 (m, 4H); ESI-MS (m/z): 412 [M+H]$^+$; Anal. Calcd for C$_{24}$H$_{30}$FN$_3$O$_2$: C, 70.05; H, 7.35; N, 10.21. Found: C, 69.86; H, 7.45; N, 10.07.

EXAMPLE 36

(a) (S)-6-{trans-4-[1-(4-Fluorophenylsulfanyl)pentan-2-ylamino]cyclohexyl}-3H-benzoxazol-2-one (b) (S)-6-{trans-4-[Ethyl(1-(4-fluorophenylsulfanyl)pentan-2-yl)amino]-cyclohexyl}-3H-benzoxazol-2-one

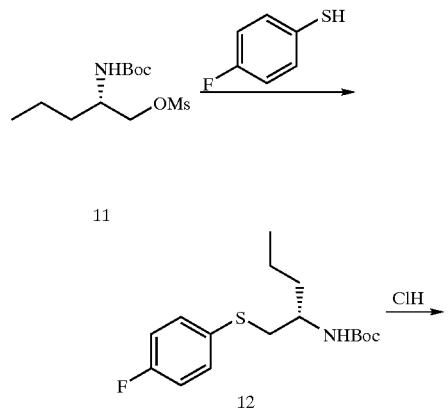

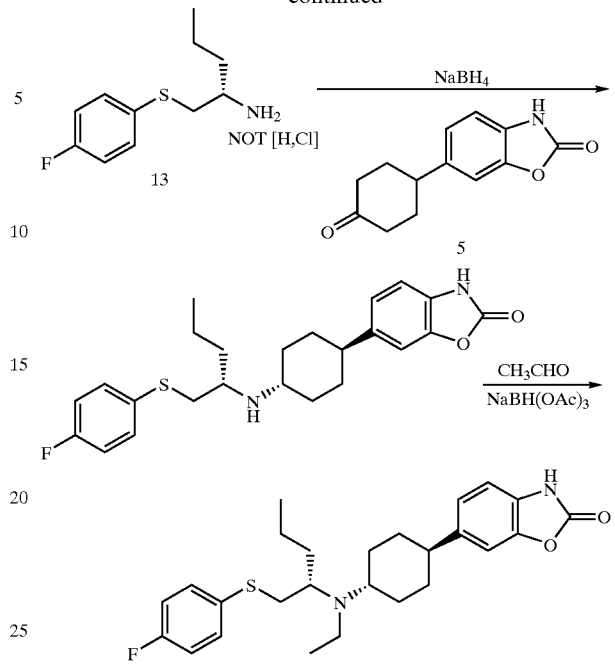

Step 1: To a stirred solution of mesylate 11 (2.23 g, 7.95 mmol) and 4--fluorobenzenethiol (1.02 g, 7.95 mmol) in THF/2-PrOH (30 mL, 1:1) was added sodium borohydride (0.39 g, 10.34 mmol). The reaction mixture was stirred overnight then diluted with EtOAc (100 mL) and washed successively with 20% KOH (3×30 mL), water (30 mL), and saturated NaCl (30 mL). The organic layer was dried (Na$_2$SO$_4$), filtered, and concentrated under reduced pressure. Purification by flash chromatography (silica, 7:1 Hexanes/EtOAc) gave Boc-protected amine 12 (1.24 g, 50%), as a white solid: $^1$H NMR (500 MHz, CDCl$_3$): δ 7.38 (dd, J=7, 4 Hz, 2H), 6.98 (t, J=4 Hz, 2H), 4.51 (br s, 1H), 3.84 (br s, 1H), 3.01 (m, 2H), 1.57 (m, 2H), 1.54 (s, 9H), 1.37 (m, 2H), 0.89 (t, J=4 Hz, 3H).

Step 2: To a stirred solution of Boc-amine 12 (1.24 g, 3.96 mmol) in dioxane (5 mL) was added HCl in dioxane (1.48 mL of a 4M solution, 5.92 mmol). The reaction mixture was concentrated under reduced pressure after 1 hour to give amine 13 (0.93 g, 94%), as a white solid: $^1$H NMR (500 MHz, CDCl$_3$): δ 8.65 (br s, 2H), 7.55 (dd, J=7, 4 Hz, 2H), 6.99 (t, J=4 Hz, 2H), 3.29–3.13 (m, 3H), 1.84 (m, 2H), 1.38 (m, 2H), 0.88 (t, J=4 Hz, 3H).

Step 3: To a stirred solution of amine 13 (0.93 g, 3.72 mmol) in 2-PrOH (30 mL) was added 4 Å molecular sieves and ketone 5 (0.88 g, 3.72 mmol). The reaction mixture was stirred for 3 hours. Sodium borohydride (0.19 g, 5.21 mmol) was added, and the mixture was stirred overnight. The reaction mixture was filtered and concentrated under reduced pressure. Purification by flash chromatography (silica, 1.5:1 Hexanes/EtOAc) gave (a) (S)-6-{trans-4-[1-(4-fluorophenylsulfanyl)pentan-2-ylamino]cyclohexyl}-3H-benzoxazol-2-one (282 mg, 17%), as a white solid: $^1$H NMR (300 MHz, CDCl$_3$): δ 7.40 (m, 2H), 7.01–6.93 (m, 5H), 3.07–2.81 (m, 3H), 2.47 (m, 2H), 1.93–1.71 (m, 4H), 1.57–1.14 (m, 8H), 0.87 (t, J=6 Hz, 3H).

Step 4: To (a) (S)-6-{trans-4-[1-(4-fluorophenylsulfanyl)pentan-2-ylamino]cyclohexyl}-3H-benzoxazol-2-one (292 mg, 0.687 mmol) in THF (10 mL) was added acetaldehyde (30 mg, 0.68 mmol) and 4 Å molecular sieves. After stirring for 0.25 hours, sodium triacetoxyborohydride (204 mg, 0.962 mmol) was added. The reaction mixture was stirred for 0.75 hours then concentrated under reduced pressure. The crude residue was taken up in methanol (10 mL), and solid NaOH was added until the pH was >8. The solution was concentrated under reduced pressure. Purification by flash chromatography (silica, 1:1 Hexanes:EtOAc) gave (b) (S)-6-{trans-4-[ethyl(1-(4-fluorophenylsulfanyl)-pentan-2-yl)amino]cyclohexyl}-3H-benzoxazol-2-one (210 mg, 67%), as a clear oil: IR (KBr): 3219, 2926, 1764, 1589 cm$^{-1}$; $^1$H NMR (500 MHz, CDCl$_3$): δ 7.34 (m, 2H), 7.05–6.92 (m, 5H), 3.02 (m, 3H), 2.79 (m, 1H), 2.64 (m, 6H), 2.38 (m, 1H), 1.93–1.78 (m, 4H), 1.47–1.29 (m, 4H), 0.93 (t, J=5 Hz, 3H), 0.89 (t, J=6 Hz, 3H); API-MS (m/z): 457 [M+H]$^+$; calcd for C$_{26}$H$_{33}$FN$_2$O$_2$S, 457.2325; found, 457.2324; HPLC: method C, 6.55 minutes (>99%), method D, 12.37 minutes (>99%).

EXAMPLE 37
(a) 6-[trans-4-(3-Phenylbutylamino)cyclohexyl]-3H-benzoxazol-2-one
(b) 6-[trans-4-(Methyl-3-phenylbutylamino)cyclohexyl]-3H-benzoxazol-2-one

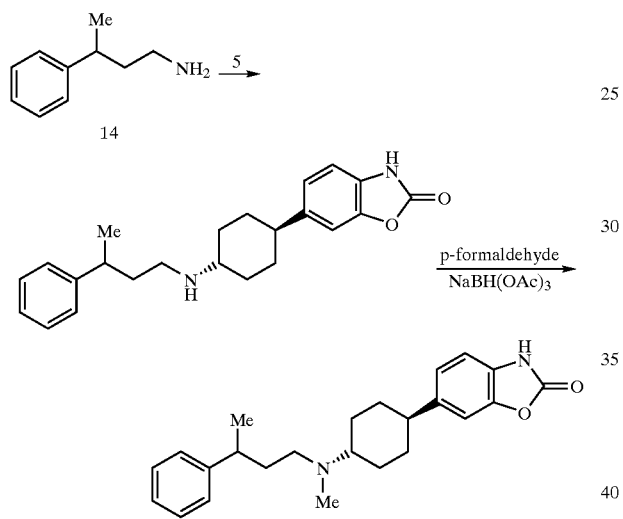

Step 1: To a stirred solution of amine 14 (1.3 g, 6.2 mmol) in THF (75 mL) was added 5 (1.44 g, 6.22 mmol). The reaction mixture was stirred for 1 hour, NaBH$_4$ (329 mg, 8.71 mmol) was added followed by water (30 mL). The reaction mixture was stirred for 45 minutes then diluted with EtOAc. The mixture was washed with 1N HCl and concentrated under reduced pressure. Purification by flash chromatography (silica, 95:5:1 CH$_2$Cl$_2$:MeOH:NH$_4$OH) gave 6-[trans-4-(3-phenylbutylamino)cyclohexyl]-3H-benzoxazol-2-one (640 mg, 28%), as a white solid: $^1$H NMR (300 MHz, DMSO-d$_6$): δ 7.31–7.11 (m, 7H), 6.94 (s, 1H), 2,78 (m, 1H), 2.45–2.35 (m, 5H), 1.87 (br d, J=10 Hz, 2H), 1.73 (br d, J=10 Hz, 2H), 1.68 (m, 2H), 1.44 (dddd, J=10, 10, 10, 2 Hz, 2H), 1.19 (d, J=4 Hz, 3H), 1.08 (dddd, J=10, 10, 10, 2 Hz, 2H).

Step 2: To a stirred solution of 6-{trans-4-[3-phenylbutylamino]-cyclohexyl}-3H-benzoxazol-2-one (638 mg, 1.75 mmol) in MeOH (10 mL) containing water (0.5 mL) was added p-formaldehyde (263 mg, 8.76 mmol). The reaction mixture was stirred for 2 hours, and NaBH$_4$ (519 mg, 2.45 mmol) was added. The reaction mixture was stirred for 3 hours. The reaction was treated with solid NaOH until a clear solution resulted and concentrated under reduced pressure. Purification by flash chromatography (95:5:1 CH$_2$Cl$_2$:MeOH:NH$_4$OH) gave 6-[trans-4-(methyl-3-phenylbutylamino)cyclohexyl]-3H-benzoxazol-2-one (231 mg, 35%), as a white solid: mp 61–70° C.; IR (KBr): 2928, 1774 cm$^{-1}$; $^1$H NMR (500 MHz, DMSO-d$_6$): δ 7.29–7.12 (m, 7H), 6.97 (s, 1H), 2.76 (m, 1H), 2.49–2.26 (m, 5H), 2.14 (s, 3H), 1.77 (m, 4H), 1.67 (m, 2H), 1.43 (m, 2H), 1.27 (m, 2H), 1.17 (d, J=4 Hz, 3H); API-MS (m/z): 379 [M+H]$^+$; HPLC: method A, 5.99 minutes (94.3%); HPLC: method B, 10.97 minutes (>99%); Anal. Calcd for C$_{24}$H$_{30}$N$_2$O$_2$·0.5H$_2$O: C, 74.39; H, 8.06; N, 7.23. Found: C, 74.41; H, 7.90; N, 7.31.

EXAMPLE 38
(a) 6-{trans-4-[3-(4-Chlorophenyl)propylamino]cyclohexyl}-3H-benzoxazol-2-one
(b) 6-(trans-4-{[3-(4-Chlorophenyl)propyl]methylamino}cyclohexyl)-3H-benzoxazol-2-one

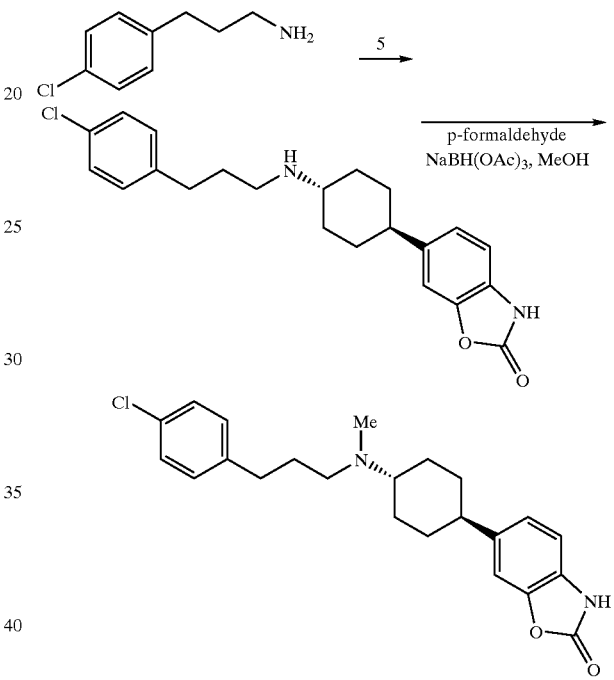

Step 1: To a solution of 3-(4-Chlorophenyl)-1-propylamine hydrochloride (1.5 g, 7.3 mmol) in 2-propanol (50 mL) was added Et$_3$N (1.1 mL, 8.0 mmol), ketone 5 (1.7 g, 7.3 mmol), THF (25 mL), and 3 Å molecular sieves. The reaction mixture was warmed to dissolve ketone 5 and then stirred at room temperature for 2.25 hours. Sodium borohydride (550 mg, 14.5 mmol) was added, and the reaction mixture was stirred for 12 hours. The reaction was quenched with MeOH, and the mixture was filtered through a pad of Celite and concentrated under reduced pressure. Purification by flash chromatography (silica, 90:10 CH$_2$Cl$_2$/MeOH) followed by trituration/recrystallization with MeOH gave 6-{trans-4-[3-(4-chlorophenyl)propylamino]cyclohexyl}-3H-benzoxazol-2-one (683 mg, 24%), as a white solid: $^1$H NMR (500 MHz, DMSO-d$_6$): δ 7.32 (d, J=8 Hz, 2H), 7.23 (d, J=8 Hz, 2H), 7.12 (s, 1H), 6.98–6.93 (m, 2H), 2.61 (t, J=7 Hz, 2H), 2.56 (t, J=7 Hz, 2H), 2.48–2.38 (m, 2H), 1.94 (br d, J=10 Hz, 2H), 1.77 (br d, J=10 Hz, 2H), 1.72–1.66 (m, 2H), 1.44 (dddd, J=12, 12, 12, 3 Hz, 2H), 1.12 (dddd, J=12, 12, 12, 3 Hz, 2H).

Step 2: To a stirred solution of 6-{trans-4-[3-(4-chlorophenyl)-propylamino]-cyclohexyl}-3H-benzoxazol-2-one (655 mg, 1.7 mmol) in MeOH (20 mL) and CH$_2$Cl$_2$ (25 mL) was added p-formaldehyde (0.70 mL of a 37 wt % solution in H₂O, 8.5 mmol). The reaction mixture was warmed to dissolve compound the amine, and then stirred at room temperature for 15 minutes. NaBH(OAc)₃ was added and stirring was continued for 12 hours. The reaction mixture was brought to pH 8 with solid NaOH, concentrated under reduced pressure, and purified by flash chromatography (silica, 95:4.5:0.5 CH₂Cl₂:MeOH:NH₄OH). Formation of the HCl salt, followed by recrystallization (MeOH:Et₂O) gave 6-(trans-4-{[3-(4-chlorophenyl)propyl]methylamino}-cyclohexyl)-3H-benzoxazol-2-one (461 mg, 66%), as a white solid: mp 267–271° C.; IR (KBr): 2949, 1769, 1494, 1452 cm⁻¹; ¹H NMR (500 MHz, DMSO-d₆): δ 11.50 (s, 1H), 10.39 (s, 1H), 7.37 (d, J=8 Hz, 2H), 7.30 (d, J=8 Hz, 2H), 7.16 (s, 1H), 7.00 (br s, 2H), 3.33–3.26 (m, 1H), 3.18–3.10 (m, 1H), 3.04–2.95 (m, 1H), 2.69 (d, J=5 Hz, 3H), 2.68–2.62 (m, 2H), 2.58–2.51 (m, 1H), 2.18–1.98 (m, 4H), 1.93–1.87 (m, 2H), 1.69–1.51 (m, 4H); HRMS-APCI (m/z): [M+H]⁺ calcd for C₂₃H₂₇ClN₂O₂, 399.1839; found, 399.1831; HPLC: method A, 6.35 minutes (98.6%); method B. 11.82 minutes (99.1%); Anal. Calcd for C₂₃H₂₇ClN₂O₂·HCl·0.25H₂O: C, 62.80; H, 6.53; N, 6.37. Found: C, 62.94; H, 6.57; N, 6.21.

EXAMPLE 39

(a) 6-(trans-4-[3-(3,5-Difluorophenyl)propylamino] cyclohexyl}-3H-benzoxazol-2-one (b) 6-(trans-{[3-(3,5-Difluorophenyl)propyl]methylamino}cyclohexyl)-3H-benzoxazol-2-one

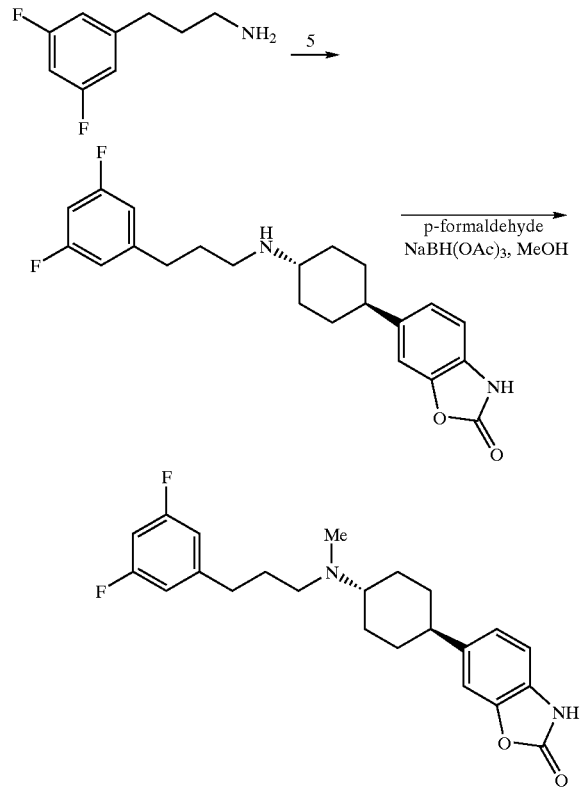

Step 1: Condensation of 3-(3,5-difluorophenyl)-1-propylamine (1.5 g, 6.5 mmol) and ketone 5 (1.5 g, 6.5 mmol), following the procedure described in Example 1, gave 6-(trans-4-[3-(3,5-difluorophenyl)propylamino] cyclohexyl}-3H-benzoxazol-2-one (640 mg, 26%), as a white solid: ¹H NMR (500 MHz, DMSO-d₆): δ 7.13 (s, 1H), 7.01–6.92 (m, 5H), 2.66 (t, J=8 Hz, 2H), 2.57 (t, J=8 Hz, 2H), 2.49–2.40 (m, 2H), 1.95 (br d, J=10 Hz, 2H), 1.78 (br d, J=10 Hz, 2H), 1.74–1.68 (m, 2H), 1.45 (dddd, J=13, 13, 13, 3 Hz, 2H), 1.14 (dddd, J=13, 13, 13, 3 Hz, 2H).

Step 2: Condensation of 6-(trans-4-[3-(3,5-difluorophenyl)propylamino]-cyclohexyl}-3H-benzoxazol-2-one (600 mg, 1.5 mmol) and p-formaldehyde (0.63 mL of a 37 wt % solution in H₂O, 7.8 mmol), following the procedure described in Example 17 followed by conversion to the HCl salt, gave 6-(trans-4-{[3-(3,5-difluorophenyl) propyl]methylamino}cyclohexyl)-3H-benzoxazol-2-one (465 mg, 71%), as a white solid: mp 270–275° C.; IR (KBr): 2950, 1762, 1626, 1596 cm⁻¹; ¹H NMR (500 MHz, DMSO-d₆): δ 11.49 (s, 1H), 10.15 (s, 1H), 7.17 (s, 1H), 7.09–7.01 (m, 4H), 7.00 (s, 1H), 3.36–3.29 (m, 1H), 3.19–3.10 (m, 1H), 3.05–2.97 (m, 1H), 2.79–2.68 (m, 5H), 2.60–2.53 (m, 1H), 2.18–2.00 (m, 4H), 1.91 (br d, J=11 Hz, 2H), 1.69–1.51 (m, 4H); ESI (m/z): 401 [M+H]⁺; HPLC: method A, 6.42 minutes (98.2%); Anal. Calcd for C₂₃H₂₆F₂N₂O₂·HCl: C, 63.23; H, 6.23; N, 6.41. Found: C, 63.04; H, 6.33; N, 6.54.

EXAMPLE 40

(a) 6-(trans-4-[3-(3,4-Difluorophenyl)propylamino] cyclohexyl}-3H-benzoxazol-2-one (b) 6-(trans-4-{[3-(3,4-Difluorophenyl)propyl]methylamino}cyclohexyl)-3H-benzoxazol-2-one

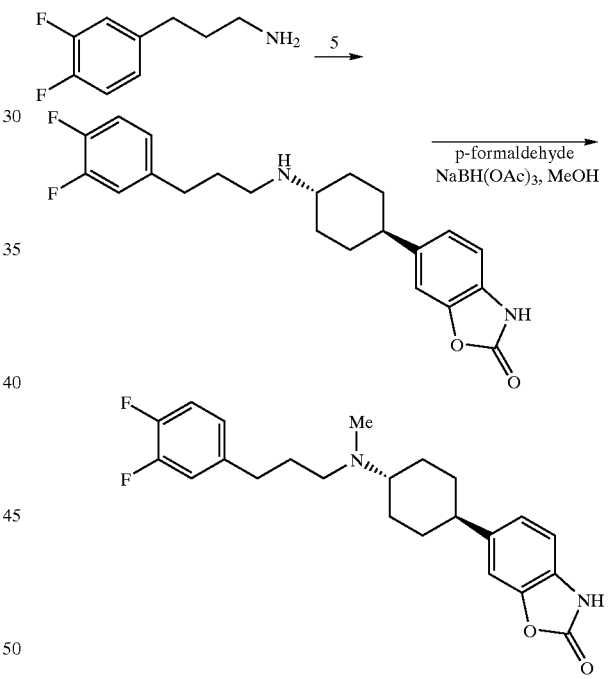

Step 1: Coupling of ketone 5 and 3-(3,4-difluorophenyl)-1-propylamine, using the method given in Example 1, gave 6-(trans-4-[3-(3,4-difluorophenyl)-propylamino] cyclohexyl}-3H-benzoxazol-2-one (690 mg, 37%): ¹H NMR (500 MHz, DMSO-d₆): δ 7.33–7.24 (m, 2H), 7.12 (d, J=1 Hz, 1H), 7.06–7.02 (m, 1H), 6.98–6.93 (m, 2H), 3.51–3.10 (br s, 2H), 2.62 (dd, J=8, 8 Hz, 2H), 2.55 (dd, J=7, 7 Hz, 2H), 2.48–2.38 (m, 2H), 1.98–1.91 (m, 2H), 1.80–1.73 (m, 2H), 1.71–1.65 (m, 2H), 1.44 (dddd, J=10, 10, 10, 3 Hz, 2H), 1.13 (dddd, J=10, 10, 10, 3 Hz, 2H).

Step 2: Condensation of 6-(trans-4-[3-(3,4-difluorophenyl)propylamino]-cyclohexyl}-3H-benzoxazol-2-one (400 mg, 1.0 mmol) with p-formaldehyde (740 mg, 24.7 mmol) following the procedure described in Example 17, except CH₂Cl₂ (15 mL) was also added, followed by formation of the HCl salt, gave 6-(trans-4-{[3-(3,4-difluorophenyl)propyl]methylamino}cyclohexyl)-3H-benzoxazol-2-one (226 mg, 52%), as a white solid: mp 224–227° C.; IR (KBr): 2945, 1764 cm$^{-1}$; $^1$H NMR (500 MHz, DMSO-d$_6$):, δ 11.50 (s, 1H), 9.94 (s, 1H), 7.40–7.34 (m, 2H), 7.16 (s, 1H), 7.12–7.09 (m, 1H), 7.00 (s, 2H), 3.33–3.29 (m, 1H), 3.18–3.11 (m, 1H), 3.03–2.97 (m, 1H), 2.71 (d, J=5 Hz, 3H), 2.68–2.63 (m, 2H), 2.59–2.50 (m, 1H), 2.14–1.98 (m, 4H), 1.94–1.88 (m, 2H), 1.66–1.51 (m, 4H); ESI-MS (m/z): 401 [M+H]$^+$; HPLC: method A, 5.97 minutes (97.1%); Anal. Calcd for $C_{23}H_{26}F_2N_2O_2$.HCl: C, 63.23; H, 6.23; N, 6.41. Found: C, 62.94; H, 6.56; N, 6.32.

EXAMPLE 41

(a) 6-(trans-4-[3-(2,4-Dimethylphenyl)propylamino]cyclohexyl}-3H-benzoxazol-2-one
(b) 6-(trans-{4-[Methyl(2,4-dimethylphenylpropyl)amino]cyclohexyl}-3H-benzoxazol-2-one

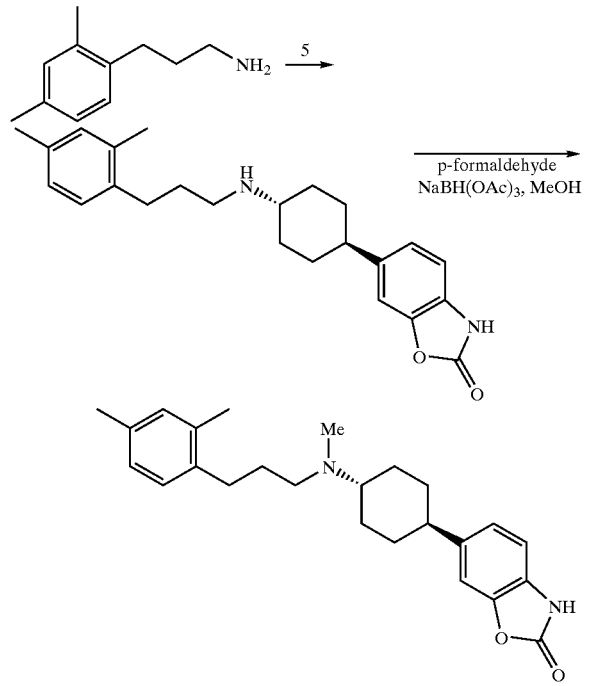

Step 1: Coupling of 5 and 3-(2,4-dimethylphenyl)-1-propylamine, using the method given in Example 1, gave 6-(trans-4-[3-(2,4-dimethylphenyl)-propylamino]cyclohexyl}-3H-benzoxazol-2-one (684 mg, 41%): $^1$H NMR (500 MHz, DMSO-d$_6$): δ 7.12 (d, J=1 Hz, 1H), 7.01–6.88 (m, 5H), 3.50–3.20 (br s, 2H), 2.59 (dd, J=7, 7 Hz, 2H), 2.55 (dd, J=7, 7 Hz, 2H), 2.49–2.39 (m, 2H), 2.22 (s, 3H), 2.21 (s, 3H), 1.98–1.92 (m, 2H), 1.81–1.75 (m, 2H), 1.65–1.59 (m, 2H), 1.44 (dddd, J=10, 10, 10, 3 Hz, 2H), 1.13 (dddd, J=10, 10, 10, 3 Hz, 2H).

Step 2: 6-(trans-4-[3-(2,4-Dimethylphenyl)propylamino]cyclohexyl}-3H-benzoxazol-2-one (400 mg, 1.0 mmol) was coupled with p-formaldehyde (740 mg, 24.7 mmol) following the procedure described in Example 17, except CH$_2$Cl$_2$ (15 mL) was also added. Formation of the HCl salt gave 6-(trans-{4-[methyl(2,4-dimethylphenylpropyl)amino]cyclohexyl})-3H-benzoxazol-2-one (247 mg, 51%), as a white solid: mp 219–223° C.; IR (KBr): 2944, 1770 cm$^{-1}$; $^1$H NMR (500 MHz, DMSO-d$_6$): δ 11.51 (s, 1H), 10.14 (s, 1H), 7.17 (s, 1H), 7.06 (d, J=8 Hz, 1H), 7.00 (s, 2H), 6.98 (s, 1H), 6.94 (d, J=8 Hz, 1H), 3.35–3.30 (m, 1H), 3.22–3.15 (m, 1H), 3.09–3.01 (m, 1H), 2.70 (d, J=5 Hz, 3H), 2.61–2.52 (m, 3H), 2.25 (s, 3H), 2.23 (s, 1H), 2.16–2.07 (m, 2H), 1.98–1.87 (m, 4H), 1.68–1.51 (m, 4H); ESI-MS (m/z): 393 [M+H]$^+$; HRMS-API (m/z): [M+H]$^+$ calcd for $C_{25}H_{32}N_2O_2$, 393.2542; found, 393.2546; HPLC: method A, 6.40 minutes (99.4%); method B, 12.03 minutes (>99%); Anal. Calcd for $C_{25}H_{32}N_2O_2$.HCl.0.5H$_2$O: C, 68.55; H, 7.82; N, 6.40. Found: C, 68.32; H, 8.03; N, 6.74.

EXAMPLE 42

(a) N-(2-{Methyl-[4-(2-oxo-2,3-dihydrobenzoxazol-6-yl)cyclohexyl]amino}-ethyl)benzamide
(b) N-{2-[4-(2-Oxo-2,3-dihydrobenzoxazol-6-yl)cyclohexylamino]ethyl}-benzamide

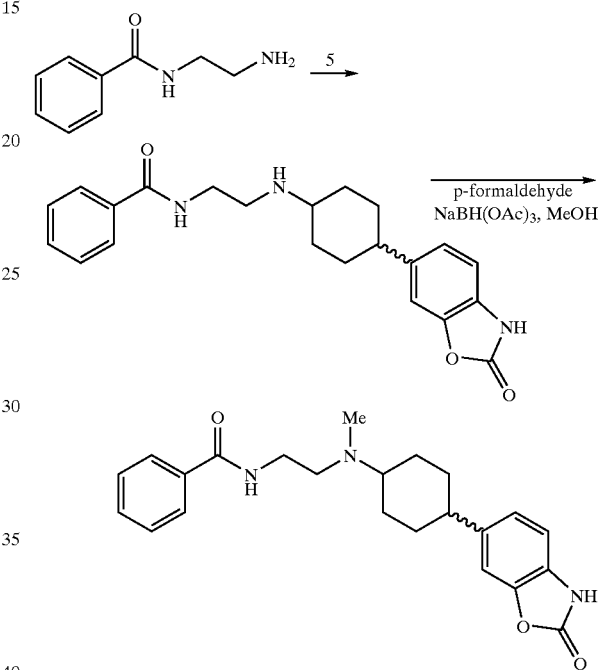

Step 1: Coupling of ketone 5 and N-(2-aminoethyl)benzamide, using the method given in Example 1, followed by conversion to the HCl salt gave N-(2-{methyl-[4-(2-oxo-2,3-dihydrobenzoxazol-6-yl)cyclohexyl]amino}ethyl)-benzamide (1.58 g, 58%) as a white solid (a mixture of cis/trans isomers): $^1$H NMR (500 MHz, DMSO-d$_6$): δ 8.84 (br s, 0.6H), 8.77 (br s, 1.4H), 7.92 (d, J=7 Hz, 2H), 7.56–7.48 (m, 3H), 7.34 (br s, 0.3H), 7.18 (s, 0.7H), 7.10 (d, J=8 Hz, 0.3H), 7.02–6.98 (m, 2.7H), 3.63–3.58 (m, 2H), 3.13–3.11 (m, 3H), 2.16 (m, 2H), 1.98–1.87 (m, 2H), 1.75–1.72 (m, 0.6H), 1.62–1.60 (m, 0.6H), 1.55–1.46 (m, 4.8H); ESI-MS (m/z): 380 [M+H]$^+$.

Step 2: Coupling of N-(2-{methyl-[4-(2-oxo-2,3-dihydrobenzoxazol-6-yl)cyclohexyl]amino}ethyl)benzamide (755 mg, 1.81 mmol) and p-formaldehyde (0.50 mL of a 37 wt % aqueous solution, 6.1 mmol), following the procedure described in Example 17 except NaOH (1.8 mL of a 1.0N aqueous solution, 1.8 mmol) and CH$_2$Cl$_2$ (5 mL) were added, gave N-{2-[4-(2-oxo-2,3-dihydrobenzoxazol-6-yl)cyclohexylamino]ethyl}benzamide (528 mg, 66%), as a white solid (a mixture of cis/trans isomers): mp 167–175° C.; IR (KBr): 2940, 1770, 1647 cm$^{-1}$; $^1$H NMR (500 MHz, DMSO-d$_6$): δ 11.51 (s, 1H), 10.41 (br s, 0.7H), 10.03 (br s, 0.3H) 8.96–8.94 (m, 1H), 8.00–7.92 (m, 2H), 7.60–7.40 (m, 3H), 7.15 (s, 1H), 7.00 (s, 1H), 3.79–3.65 (m, 2H), 3.45–3.19 (m, 2H), 2.82–2.79 (m, 4H), 2.58–2.50 (m, 1H), 2.20–2.10 (m, 2H), 1.92–1.81 (m, 3H), 1.70–1.51 (m, 4H); ESI-MS (m/z): 394 [M+H]+; HPLC: method A, 4.89 minutes (95.0%); method B, 10.0 minutes (>99%); Anal. Calcd for $C_{23}H_{27}FN_3O_3 \cdot HCl \cdot 0.75H_2O$: C, 62.30; H, 6.71; N, 9.48. Found: C, 62.43; H, 6.68; N, 9.62.

EXAMPLE 43

(a) 6-(trans-4-[3-(4-Fluoro-2-methylphenyl)propylamino]cyclohexyl}-3H-benzoxazol-2-one; and (b) 6-(trans-{4-[Methyl(4-fluoro-2-methylphenylpropyl)amino]cyclohexyl})-3H-benzoxazol-2-one

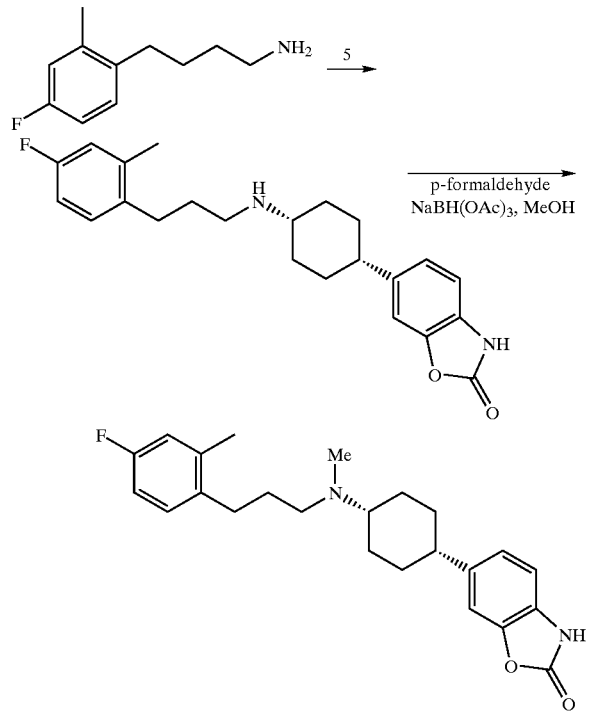

Step 1: Coupling of ketone 5 and 3-(4-fluoro-2-methylphenyl)-1-propylamine, using the method given in Example 1, gave 6-(trans-4-[3-(4-fluoro-2-methylphenyl)propylamino]cyclohexyl}-3H-benzoxazol-2-one (630 mg, 56%) as the HCl salt: $^1$H NMR (500 MHz, DMSO-d$_6$): δ 11.50 (s, 1H), 8.88 (s, 2H), 7.22–7.13 (m, 2H), 7.05–6.91 (m, 4H), 3.09–2.87 (m, 3H), 2.67–2.62 (m, 3H), 2.30 (s, 3H), 2.17–2.13 (m, 2H), 1.92–1.79 (m, 4H), 1.58–1.41 (m, 4H).

Step 2: 6-(trans-4-[3-(4-Fluoro-2-methylphenyl)propylamino]-cyclohexyl}-3H-benzoxazol-2-one (600 mg, 1.4 mmol) was coupled with p-formaldehyde (1.1 g, 37 mmol), following the procedure described in Example 17, gave 6-(trans-{4- [methyl(4-fluoro-2-methylphenylpropyl)amino]-cyclohexyl})-3H-benzoxazol-2-one (226 mg, 52%), as the HCl salt: mp 266–279° C.; IR (KBr): 2950, 1768 cm$^{-1}$; $^1$H NMR (500 MHz, DMSO-d$_6$): δ 11.50 (s, 1H), 10.20 (s, 1H), 7.24–7.20 (m, 1H), 7.17 (s, 1H), 7.04–6.94 (m, 4), 3.32–3.30 (m, 1H), 3.21–3.02 (m, 2H), 3.15–3.02 (m, 1H), 2.70 (br s, 3H), 2,63–2.52 (m, 2H), 2.30 (s, 3H), 2.18–2.07 (m, 2H), 1.99–1.88 (m, 4H), 1.69–1.51 (m, 4); ESI-MS (m/z): 397 [M+H]+; HRMS-API (m/z): [M+H]+ calcd for $C_{24}H_{29}FN_2O_2$, 397.2291; found, 397.2296; HPLC: method A, 5.99 minutes (99.0%); method B, 11.81 minutes (>99%); Anal. Calcd for $C_{24}H_{29}FN_2O_2 \cdot HCl \cdot 0.25H_2O$: C, 65.89; H, 7.03; N, 6.40. Found: C, 65.93; H, 7.10; N, 6.37.

EXAMPLE 44

(a) 6-{trans-4-[3-(2-Chloro-4-fluorophenyl)propylamino]cyclohexyl}-3H-benzoxazol-2-one; and (b) 6-(trans-4-{[3-(2-Chloro-4-fluorophenyl)propyl]methylamino}cyclohexyl)-3H-benzoxazol-2-one

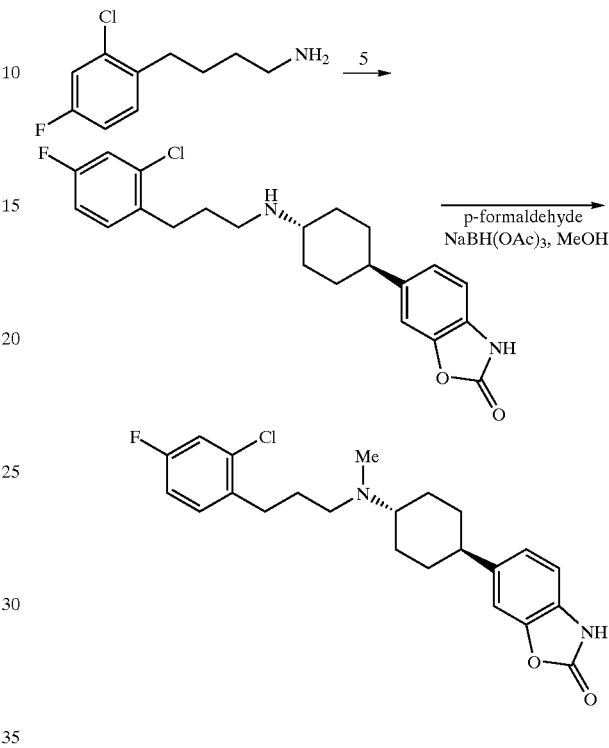

Step 1: Condensation of 3-(2-Chloro-4-fluorophenyl)-1-propylamine (1.5 g, 6.5 mmol) and ketone 5 (1.5 g, 6.5 mmol), following the procedure described in Example 1, gave 6-{trans-4-[3-(2-chloro-4-fluorophenyl)-propylamino]cyclohexyl}-3H-benzoxazol-2-one (535 mg, 21%), as a white solid: $^1$H NMR (500 MHz, DMSO-d$_6$): δ 7.41–7.35 (m, 2H), 7.17–7.13 (m, 2H), 6.99–6.94 (m, 2H), 3.60–2.90 (br s, 2H), 2.72 (t, J=8 Hz, 2H), 2.59 (t, J=8 Hz, 2H), 2.49–2.40 (m, 2H), 1.95 (br d, J=12 Hz, 2H), 1.77 (br d, J=12 Hz, 2H), 1.69–1.66 (m, 2H), 1.44 (dddd, J=13, 13, 13, 3 Hz, 2H), 1.13 (dddd, J=13, 13, 13, 3 Hz, 2H).

Step 2: Condensation of 6-{trans-4-[3-(2-chloro-4-fluorophenyl)-propylamino]cyclohexyl}-3H-benzoxazol-2-one (530 mg, 1.3 mmol) and p-formaldehyde (0.43 mL of a 37 wt % solution in H$_2$O, 5.3 mmol), following the procedure described Example 17, followed by conversion to the HCl salt, gave 6-(trans-4-{[3-(2-chloro-4-fluorophenyl)propyl]methylamino}-cyclohexyl)-3H-benzoxazol-2-one (226 mg, 38%), as a white solid: mp 256–262° C.; IR (KBr): 2948, 1770, 1492, 1451 cm$^{-1}$; $^1$H NMR (500 MHz, DMSO-d$_6$): δ 11.49 (s, 1H), 10.05 (s, 1H), 7.49–7.42 (m, 2H), 7.24–7.19 (m, 1H), 7.17 (br s, 1H), 7.00 (d, J=1 Hz, 2H), 3.35–3.29 (m, 1H), 3.24–3.18 (m, 1H), 3.11–3.03 (m, 1H), 2.84–2.70 (m, 5H), 2.59–2.51 (m, 1H), 2.18–1.88 (m, 6H), 1.69–1.51 (m, 4H); ESI (m/z): 417 [M+H]+; HRMS-API (m/z): [M+H]+ calcd for $C_{23}H_{26}ClFN_2O_2$, 417.1745; found, 417.1748; HPLC: method A, 5.88 minutes (>99%); method B, 12.00 minutes (>99%); Anal. Calcd for $C_{23}H_{26}ClFN_2O_2 \cdot HCl \cdot 0.25H_2O$: C, 60.33; H, 6.05; N, 6.12. Found: C, 60.35; H, 6.08; N, 5.93.

EXAMPLE 45

(a) 6-{trans-4-[3-(4-Chloro-2-fluorophenyl)propylamino]cyclohexyl}-3H-benzoxazol-2-one (b) 6-(trans-4-{[3-(4-Chloro-2-fluorophenyl)propyl]methylamino}cyclohexyl)-3H-benzoxazol-2-one

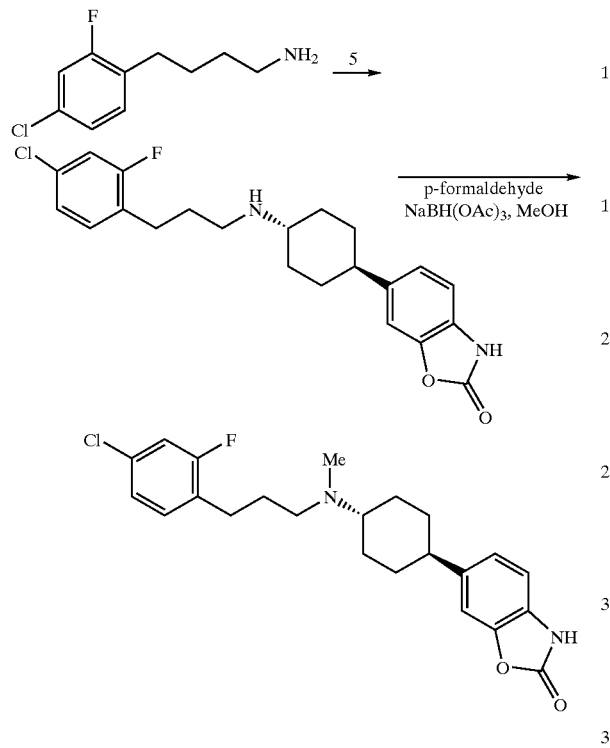

Step 1: Condensation of 3-(4-chloro-2-fluorophenyl)-1-propylamine (1.5 g, 6.5 mmol) and ketone 5 (1.5 g, 6.5 mmol), following the procedure described in Example 1, gave 6-{trans-4-[3-(4-chloro-2-fluorophenyl)-propylamino]cyclohexyl}-3H-benzoxazol-2-one (479 mg, 18%), as a white solid: $^1$H NMR (500 MHz, DMSO-$d_6$): δ 7.36–7.32 (m, 2H), 7.22–7.20 (m, 1H), 7.13 (d, J=1 Hz, 1H), 6.99–6.94 (m, 2H), 3.70–3.00 (br s, 2H), 2.64 (t, J=8 Hz, 2H), 2.57 (t, J=8 Hz, 2H), 2.47–2.38 (m, 2H), 1.94 (br d, J=10 Hz, 2H), 1.77 (br d, J=10 Hz, 2H), 1.70–1.64 (m, 2H), 1.44 (dddd, J=13, 13, 13, 3 Hz, 2H), 1.13 (dddd, J=13, 13, 13, 3 Hz, 2H).

Step 2: Condensation of 6-{trans-4-[3-(4-chloro-2-fluorophenyl)-propylamino]cyclohexyl}-3H-benzoxazol-2-one (460 mg, 1.1 mmol) and p-formaldehyde (0.40 mL of a 37 wt % solution in $H_2O$, 5.3 mmol), following the procedure described in Example 17 followed by conversion to the HCl salt, gave 6-(trans-4-{[3-(4-chloro-2-fluorophenyl)propyl]methylamino}cyclohexyl)-3H-benzoxazol-2-one (351 mg, 70%), as a white solid: mp 274–275° C.; IR (KBr): 2950, 1773, 1490, 1452 cm$^{-1}$; $^1$H NMR (500 MHz, DMSO-$d_6$): δ 11.50 (s, 1H), 10.32 (s, 1H), 7.43–7.38 (m, 2H), 7.28–7.26 (m, 1H), 7.16 (br s, 1H), 7.00 (d, J=1 Hz, 2H), 3.33–3.28 (m, 11H), 3.21–3.14 (m, 1H), 3.07–2.99 (m, 1H), 2.74–2.63 (m, 5H), 2.58–2.52 (m, 1H), 2.18–1.96 (m, 4H), 1.93–1.88 (m, 2H), 1.68–1.51 (m, 4H); ESI (m/z): 417 [M+H]$^+$; HPLC: method A, 5.94 minutes (>99%); method B, 12.09 minutes (>99%); Anal. Calcd for $C_{23}H_{26}ClFN_2O_2 \cdot HCl$: C, 60.93; H, 6.00; N, 6.18. Found: C, 60.76; H, 6.09; N, 6.00.

EXAMPLE 46

(a) 6-{trans-4-[3-(2-Fluorophenyl)propylamino]cyclohexyl}-3H-benzoxazol-2-one (b) 6-(trans-4-{[3-(2-Fluorophenyl)propyl]methylamino}cyclohexyl)-3H-benzoxazol-2-one

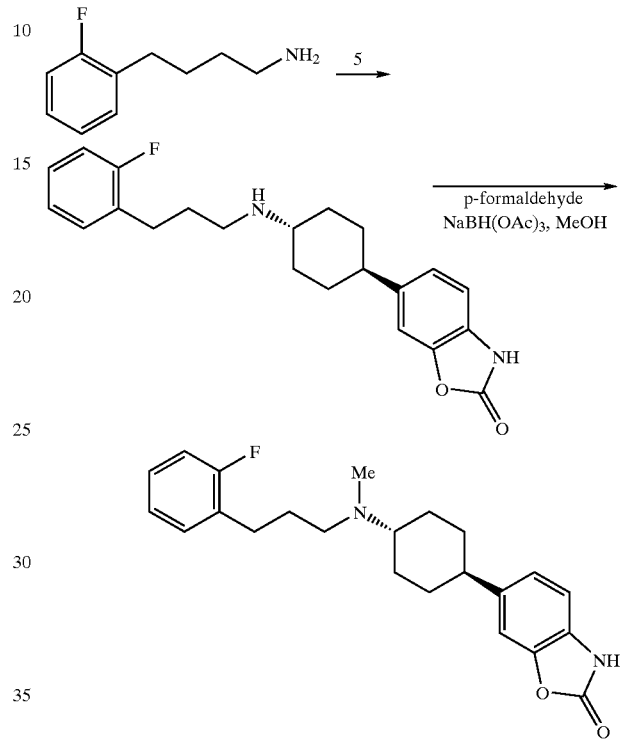

Coupling of ketone 5 and 3-(2-fluorophenyl)-1-propylamine, using the method given in Example 1, gave 6-{trans-4-[3-(2-fluorophenyl)propylamino]-cyclohexyl}-3H-benzoxazol-2-one (1.7 g, 45%) as the HCl salt: $^1$H NMR (500 MHz, DMSO-$d_6$): δ 11.50 (s, 1H), 8.86 (s, 2H), 7.34 (t, J=8 Hz, 1H), 7.35–7.26 (m, 1H), 7.19–7.15 (m, 3H), 7.02–6.97 (m, 2H), 3.10–3.03 (m, 1H), 2.98–2.92 (m, 2H), 2.72 (dd, J=8, 8 Hz, 2H), 2.57–2.50 (m, 1H), 2.18–2.13 (m, 2H), 1.98–1.92 (m, 2H), 1.89–1.85 (m, 2H), 1.57–1.46 (m, 4H).

6-{trans-4-[3-(2-Fluorophenyl)propylamino]cyclohexyl}-3H-benzoxazol-2-one (700 mg, 1.7 mmol) was coupled with p-formaldehyde (0.37 g, 12.3 mmol), following the procedure described in Example 17, gave 6-(trans-4-{[3-(2-fluorophenyl)propyl]methylamino}cyclohexyl)-3H-benzoxazol-2-one (407 mg, 57%), as the HCl salt: mp 242–246° C.; IR (KBr): 2944, 1765 cm$^{-1}$; $^1$H NMR (500 MHz, DMSO-$d_6$): δ 11.52 (s, 1H), 10.42 (s, 1H), 7.39–7.35 (m, 1H), 7.31–7.26 (m, 1H), 7.18–7.15 (m, 3H), 7.00 (s, 2H), 3.34–3.30 (m, 1H), 3.21–3.15 (m, 1H), 3.09–3.01 (m, 1H), 2.69 (d, J=4 Hz, 5H), 2.58–2.51 (m, 1H), 2.18–1.98 (m, 4H), 1.93–1.87 (m, 2H), 1.69–1.51 (m, 4H); ESI-MS (m/z): 383 [M+H]$^+$; HPLC: method A, 5.66 minutes (99.4%); method B, 11.21 minutes (>99%); Anal. Calcd for $C_{23}H_{27}FN_2O_2 \cdot HCl \cdot 0.25H_2O$: C, 65.24; H, 6.78; N, 6.62. Found: C, 65.34; H, 6.65; N, 6.53.

EXAMPLE 47

(a) 6-{trans-4-[3-(3-Fluorophenyl)propylamino]cyclohexyl}-3H-benzoxazol-2-one (b) 6-(trans-4-{[3-(3-Fluorophenyl)propyl]methylamino}cyclohexyl)-3H-benzoxazol-2-one

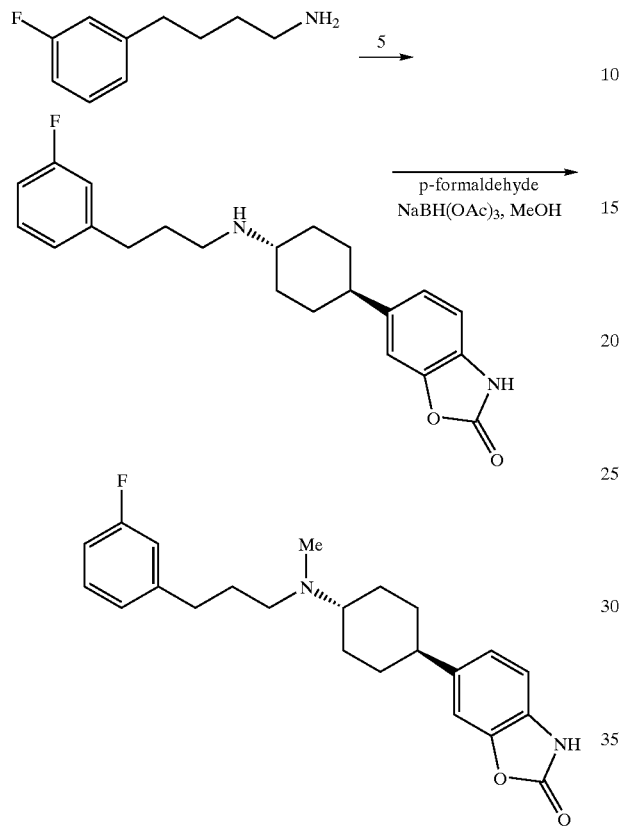

EXAMPLE 48

(a) 6-{trans-4-[3-(3-Fluoro-2-methylphenyl)propylamino]cyclohexyl}-3H-benzoxazol-2-one (b) 6-(trans-4-{[3-(3-Fluoro-2-methylphenyl)propyl]methylamino}cyclohexyl)-3H-benzoxazol-2-one

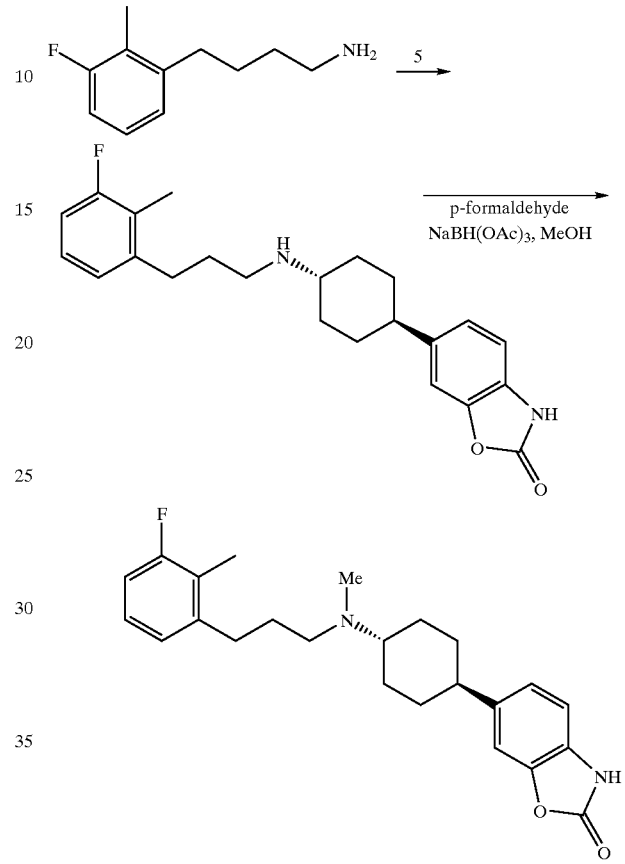

Coupling of ketone 5 and 3-(3-fluorophenyl)-1-propylamine, using the method given in Example 1, gave 6-{trans-4-[3-(3-fluorophenyl)propylamino]-cyclohexyl}-3H-benzoxazol-2-one (1.4 g, 37%) as the HCl salt: $^1$H NMR (500 MHz, DMSO-$d_6$): δ 11.48 (s, 1H), 8.79 (s, 2H), 7.38–7.33 (m, 1H), 7.17 (s, 1H), 7.12–7.08 (m, 2H), 7.06–6.97 (m, 3H), 3.10–3.03 (m, 1H), 2.97–2.89 (m, 2H), 2.71 (dd, J=8, 8 Hz, 2H), 2.57–2.50 (m, 1H), 2.18–2.11 (m, 2H), 1.98–1.92 (m, 2H), 1.89–1.85 (m, 2H), 1.57–1.46 (m, 4H).

6-{trans-4-[3-(3-Fluorophenyl)propylamino]cyclohexyl}-3H-benzoxazol-2-one (700 mg, 1.7 mmol) was coupled with p-formaldehyde (0.37 g, 12.3 mmol), following the procedure described in Example 17, gave 6-(trans-4-{[3-(3-fluorophenyl)propyl]methylamino}cyclohexyl)-3H-benzoxazol-2-one (381 mg, 54%), as the HCl salt: mp 210–238° C.; IR (KBr): 2944, 1763 cm$^{-1}$; $^1$H NMR (500 MHz, DMSO-$d_6$): δ 11.51 (s, 1H), 10.21 (s, 1H), 7.38–7.34 (m, 1H), 7.16 (s, 1H), 7.14–7.09 (m, 2H), 7.04–7.02 (m, 1H), 7.00 (s, 2H), 3.33–3.30 (m, 1H), 3.19–3.11 (m, 1H), 3.05–2.98 (m, 1H), 2.72–2.63 (m, 5H), 2.58–2.51 (m, 1H), 2.18–1.98 (m, 4H), 1.93–1.87 (m, 2H), 1.69–1.51 (m, 4H); ESI-MS (m/z): 383 [M+H]$^+$; HPLC: method A, 5.75 minutes (99.0%); Anal. Calcd for $C_{23}H_{27}FN_2O_2 \cdot HCl$: C, 65.94; H, 6.74; N, 6.69. Found: C, 65.72; H, 6.77; N, 6.68.

Coupling of ketone 5 and 3-(2-methyl-3-fluorophenyl)-1-propylamine, using the method given in Example 1, gave 6-{trans-4-[3-(3-fluoro-2-methylphenyl)propylamino]cyclohexyl}-3H-benzoxazol-2-one (1.4 g, 56%): $^1$H NMR (500 MHz, DMSO-$d_6$): δ 7.16–7.10 (m, 2H), 7.01–6.93 (m, 4H), 2.65 (dd, J=8, 8 Hz, 2H), 2.60 (dd, J=7, 7 Hz, 2H), 2.49–2.39 (m, 2H), 2.18 (d, J=2 Hz, 3H), 1.98–1.93 (m, 2H), 1.81–1.75 (m, 2H), 1.68–1.61 (m, 2H), 1.45 (dddd, J=13, 13, 13, 3 Hz, 2H), 1.13 (dddd, J=13, 13, 13, 3 Hz, 2H).

6-{trans-4-[3-(3-Fluoro-2-methylphenyl)propylamino]cyclohexyl}-3H-benzoxazol-2-one (700 mg, 1.7 mmol) was coupled with p-formaldehyde (1.48 g, 49.3 mmol), following the procedure described in Example 17, gave 6-(trans-4-{[3-(3-fluoro-2-methylphenyl)propyl]methylamino}cyclohexyl)-3H-benzoxazol-2-one (432 mg, 55%), as the HCl salt: mp 264–269° C.; IR (KBr): 2947, 1769 cm$^{-1}$; $^1$H NMR (500 MHz, DMSO-$d_6$): δ 11.50 (s, 1H), 10.02 (s, 1H), 7.21–7.15 (m, 2H), 7.07–6.99 (m, 4H), 3.35–3.30 (m, 1H), 3.25–3.18 (m, 1H), 3.11–3.05 (m, 1H), 2.71 (d, J=5 Hz, 3H), 2.70–2.62 (m, 2H), 2.58–2.51 (m, 1H), 2.20 (d, J=2 Hz, 3H), 2.17–2.07 (m, 2H), 2.00–1.88 (m, 4H), 1.69–1.51 (m, 4H); ESI-MS (m/z): 397 [M+H]$^+$; HPLC: method A, 6.09 minutes (98.3%); method B, 11.66 minutes (>99%); Anal. Calcd for $C_{24}H_{29}FN_2O_2 \cdot HCl \cdot 0.25H_2O$: C, 65.89; H, 7.03; N, 6.40. Found: C, 66.01; H, 6.85; N, 6.35.

EXAMPLE 49

(a) 6-{trans-4-[(3-Cyclohexylpropyl)amino]cyclohexyl}-3H-benzoxazol-2-one (b) 6-{trans-4-[(3-Cyclohexylpropyl)methylamino]cyclohexyl}-3H-benzoxazol-2-one

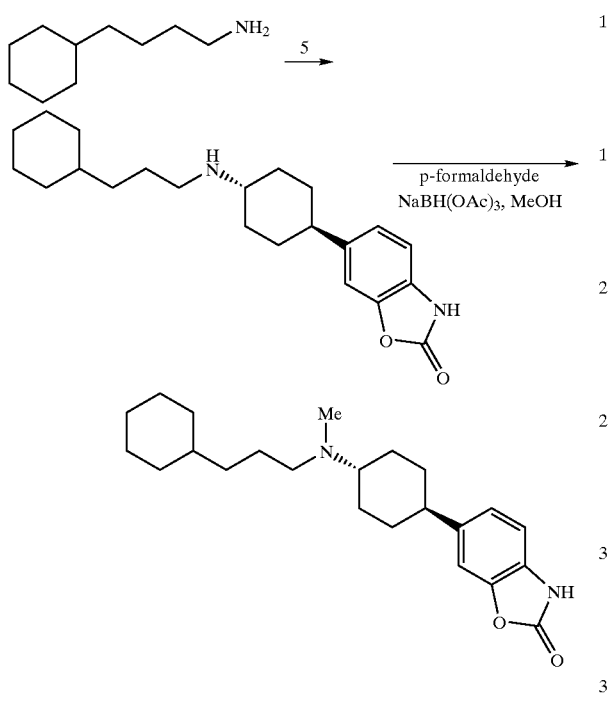

EXAMPLE 50

(a) 6-{trans-[4-(2-Methyl-3-phenylpropylamino)cyclohexyl]}-3H-benzoxazol-2-one (b) 6-(trans-{4-[Methyl(2-methyl-3-phenylpropyl)amino]cyclohexyl})-3H-benzoxazol-2-one

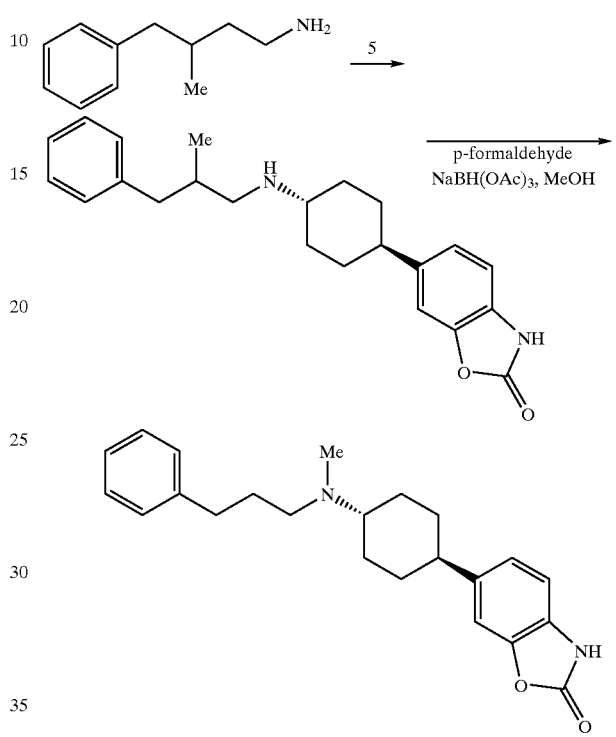

Step 1: Condensation of cyclohexyl-1-propylamine (0.9 g, 6.4 mmol) and ketone 5 (1.5 g, 6.4 mmol), following the procedure described in Example 1, gave 6-{trans-4-[(3-cyclohexylpropyl)amino]cyclohexyl}-3H-benzoxazol-2-one (352 mg, 15%), as a white solid: $^1$H NMR (500 MHz, DMSO-$d_6$): δ 7.12 (br s, 1H), 6.97–6.93 (m, 2H), 3.70–3.10 (br s, 2H), 2.53 (t, J=7 Hz, 2H), 2.48–2.39 (m, 2H), 1.95 (br d, J=12 Hz, 2H), 1.77 (br d, J=12 Hz, 2H), 1.70–1.59 (m, 5H), 1.50–1.38 (m, 4H), 1.23–1.08 (m, 8H), 0.90–0.81 (m, 2H).

Step 2: Condensation of 6-{trans-4-[(3-cyclohexylpropyl)amino]-cyclohexyl}-3H-benzoxazol-2-one (350 mg, 0.98 mmol) and p-formaldehyde (0.40 mL of a 37 wt % solution in $H_2O$, 4.9 mmol), following the procedure described in Example 17 followed by conversion to the HCl salt, gave 6-{trans-4-[(3-cyclohexylpropyl)methylamino]cyclohexyl}-3H-benzoxazol-2-one (235 mg, 58%), as a white solid: mp 247–251° C.; IR (KBr): 2931, 1771, 1502, 1451 cm$^{-1}$; $^1$H NMR (500 MHz, DMSO-$d_6$): δ 11.50 (s, 1H), 10.12 (s, 1H), 7.16 (s, 1H), 7.00 (s, 2H), 3.32–3.25 (m, 1H), 3.11–3.04 (m, 1H), 2.99–2.91 (m, 1H), 2.67 (d, J=5 Hz, 3H), 2.59–2.52 (m, 1H), 2.18–2.08 (m, 2H), 1.94–1.88 (m, 2H), 1.76–1.51 (m, 11 H), 1.29–1.09 (m, 6H), 0.93–0.85 (m, 2H); ESI (m/z): 371 [M+H]$^+$; HRMS-API (m/z): [M+H]$^+$ calcd for $C_{23}H_{34}N_2O_2$, 371.2698; found, 371.2708; HPLC: method A, 6.32 minutes (99.0%); method B, 12.58 minutes (>99%); Anal. Calcd for $C_{23}H_{34}N_2O_2 \cdot HCl \cdot 0.25H_2O$: C, 67.13; H, 8.70; N, 6.81. Found: C, 67.24; H, 8.65; N, 6.73.

Step 1: Condensation of 2-methyl-3-phenylpropylamine (830 mg, 3.97 mmol) and ketone 5 (918 mg, 3.97 mmol), following the procedure described in Example 1, gave compound 6-{trans-[4-(2-methyl-3-phenylpropylamino)-cyclohexyl]}-3H-benzoxazol-2-one (400 mg, 48%): $^1$H NMR (500 MHz, DMSO-$d_6$): δ 7.32–7.21 (m, 2H), 7.19–7.17 (m, 4H), 7.03–6.98 (m, 2H), 2.77 (dd, J=13, 6 Hz, 1H), 2.55–2.34 (m, 7H), 1.99–1.97 (m, 2H), 1.84–1.80 (m, 2H), 1.50–1.47 (m, 2H), 1.18–1.05 (m, 2H), 0.88 (d, J=6 Hz, 3H).

Step 2: Condensation of 6-{trans-[4-(2-methyl-3-phenylpropylamino)-cyclohexyl]}-3H-benzoxazol-2-one (400 mg, 1.10 mmol) and p-formaldehyde (0.50 mL of a 37 wt % solution in $H_2O$, 2.4 mmol), following the procedure described in Example 17, gave 6-(trans-{4-[methyl(2-methyl-3-phenylpropyl)-amino]cyclohexyl})-3H-benzoxazol-2-one (200 mg, 52%), as a white foam: mp 43–48° C.; IR (film): 2927, 1776, 1495, 1450 cm$^{-1}$; $^1$H NMR (500 MHz, DMSO-$d_6$): δ 7.28–7.25 (m, 2H), 7.17–7.15 (m, 4H), 7.00–6.95 (m, 2H), 2.78 (dd, J=13, 5 Hz, 1H), 2.46–2.41 (m, 1H), 2.29–2.14 (m, 6H), 1.83–1.78 (m, 6H), 1.49–1.34 (m, 4H), 0.76 (d, J=6 Hz, 3H); ESI (m/z): 379 [M+H]$^+$; HPLC: method A, 5.96 minutes (>99%); method B, 10.99 minutes (97.1%); Anal. Calcd for $C_{24}H_{30}N_2O_2 \cdot 0.125H_2O$: C, 75.51; H, 8.25; N, 7.34. Found: C, 75.26; H, 7.88; N, 7.20.

EXAMPLE 51

(a) 6-{trans-[4-(3-Phenyl-prop-2-ynylamino)cyclohexyl]}-3H-benzoxazol-2-one (b) 6-(trans-{4-[Methyl(3-phenyl-prop-2-ynyl)amino]cyclohexyl})-3H-benzoxazol-2-one

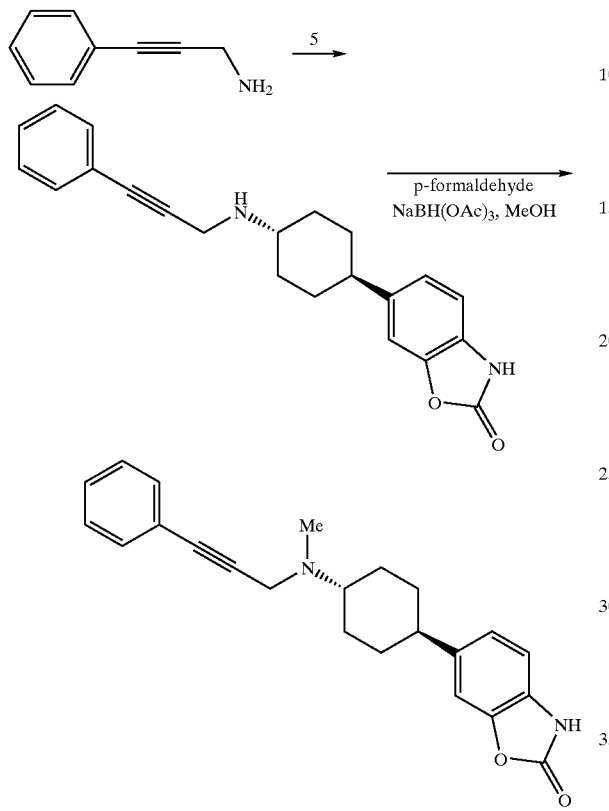

Step 1: Condensation of 3-phenyl-prop-2-ynylamine (1.0 g, 7.6 mmol) and ketone 5 (1.7 g, 7.6 mmol), following the procedure described in Example 1, except THF was used as solvent gave compound 6-{trans-[4-(3-phenyl-prop-2-ynylamino)cyclohexyl]}-3H-benzoxazol-2-one (400 mg, 58%) as a white solid: $^1$H NMR (500 MHz, DMSO-$d_6$): δ 7.45–7.35 (m, 5H), 7.19 (s, 1H), 7.50–6.94 (m, 2H), 3.59 (s, 2H), 3.30 (m, 2H), 2.75–2.61 (m, 1H), 2.06–2.00 (m, 2H), 1.85–1.80 (m, 2H), 1.58–1.41 (m, 2H), 1.25–1.10 (m, 2H).

Step 2: Condensation of 6-{trans-[4-(3-phenyl-prop-2-ynylamino)-cyclohexyl]}-3H-benzoxazol-2-one (400 mg, 1.20 mmol) and p-formaldehyde (180 mg of a 37 wt % solution in $H_2O$, 6.0 mmol), following the procedure described in Example 17, gave 6-(trans-{4-[methyl(3-phenyl-prop-2-ynyl)-amino]cyclohexyl})-3H-benzoxazol-2-one (100 mg, 65%), as a white solid: mp 249–252° C.; IR (KBr): 2938, 2627, 1770 cm$^{-1}$; $^1$H NMR (500 MHz, DMSO-$d_6$): δ 7.55 (d, J=6 Hz, 2H), 7.47–7.43 (m, 2H), 7.20 (s, 1H), 7.03–6.98 (m, 2H), 4.38 (s, 2H), 3.42–3.33 (m, 3H), 2.86 (s, 3H), 2.56–2.50 (m, 1H), 2.22 (m, 2H), 1.94 (brd, J=11 Hz, 2H), 1.71–1.67 (m, 2H), 1.57–1.55 (m, 2H); HRMS-APCI (m/z): [M+H]$^+$ calcd for $C_{23}H_{25}N_2O_2$, 361.1916; found, 361.1914; HPLC: method A, 5.74 minutes (>99%); method B, 11.03 minutes (>99%); Anal. Calcd for $C_{23}H_{24}N_2O_2 \cdot HCl \cdot 0.5H_2O$: C, 68.06; H, 6.46; N, 6.90. Found: C, 67.81; H, 6.65; N, 6.74.

EXAMPLE 52

(a) 6-{trans-4-[4-(3-Thiophen-3-yl)propylamino]cyclohexyl}-3H-benzoxazol-2-one (b) 6-[trans-4-{[3-(3-Thiophen-3-yl)propyl]methylamino}cyclohexyl)-3H-benzoxazol-2-one

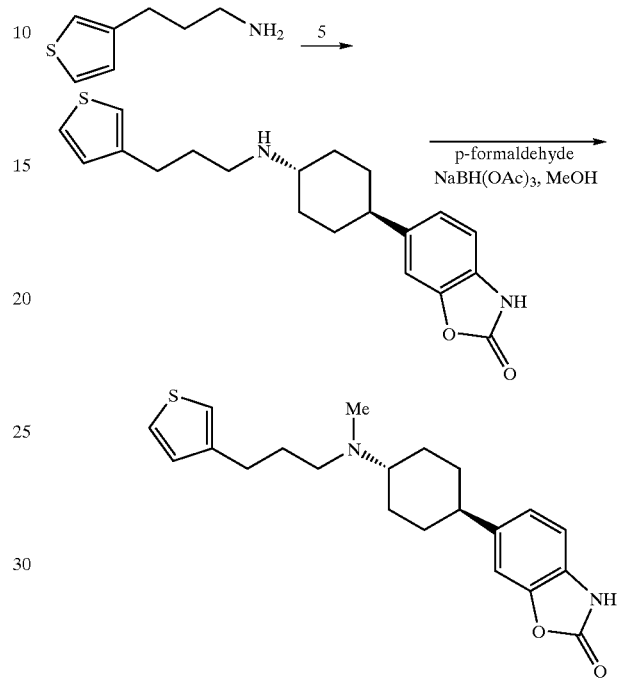

Step 1: Condensation of (3-thienyl)-1-propylamine (2.8 g, 20.0 mmol) and ketone 5 (4.6 g, 20.0 mmol), following the procedure described in Example 1, gave compound 6-{trans-4-[4-(3-thiophen-3-yl)propylamino]cyclohexyl}-3H-benzoxazol-2-one (410 mg, 5%), as a white solid: $^1$H NMR (500 MHz, DMSO-$d_6$): δ 7.43–7.41 (m, 1H), 7.14–7.12 (m, 2H), 7.00–6.93 (m, 3H), 3.60–3.10 (br s, 2H), 2.63 (t, J=7 Hz, 2H), 2.58 (t, J=7 Hz, 2H), 2.49–2.39 (m, 2H), 1.95 (br d, J=11 Hz, 2H), 1.78 (br d, J=11 Hz, 2H), 1.73–1.68 (m, 2H), 1.45 (dddd, J=13, 13, 13, 3 Hz, 2H), 1.13 (dddd, J=13, 13, 13, 3 Hz, 2H).

Step 2: Condensation of 6-{trans-4-[4-(3-thiophen-3-yl)propylamino]-cyclohexyl}-3H-benzoxazol-2-one (400 mg, 1.0 mmol) and p-formaldehyde (0.17 mL of a 37 wt % solution in $H_2O$, 2.0 mmol), following the procedure described in Example 17, followed by conversion to the HCl salt, gave 6-[trans-4-{[3-(3-thiophen-3-yl)propyl]methylamino}cyclohexyl)-3H-benzoxazol-2-one (301 mg, 74%), as a white solid: mp 246–248° C.; IR (KBr): 2950, 1759, 1496, 1451 cm$^{-1}$; $^1$H NMR (500 MHz, DMSO-$d_6$): δ 11.47 (s, 1H), 10.09 (s, 1H), 7.50–7.48 (m, 1H), 7.25–7.24 (m, 1H), 7.16 (s, 1H), 7.05–7.04 (m, 1H), 7.00 (s, 2H), 3.34–3.28 (m, 1H), 3.19–3.10 (m, 1H), 3.05–2.98 (m, 1H), 2.71 (d, J=5 Hz, 3H), 2.69–2.65 (m, 2H), 2.58–2.51 (m, 1H), 2.15–2.00 (m, 4H), 1.94–1.88 (m, 2H), 1.68–1.51 (m, 4H); ESI (m/z): 371 [M+H]$^+$; HPLC: method B, 10.79 minutes (>99%); Anal. Calcd for $C_{21}H_{26}N_2O_2S \cdot HCl$: C, 61.98; H, 6.69; N, 6.88. Found: C, 61.64; H, 6.79; N, 6.70.

EXAMPLE 53

6-(trans-4-{[3-(4-Isopropylphenyl)propyl]methylamino}cyclohexyl)-3H-benzoxazol-2-one

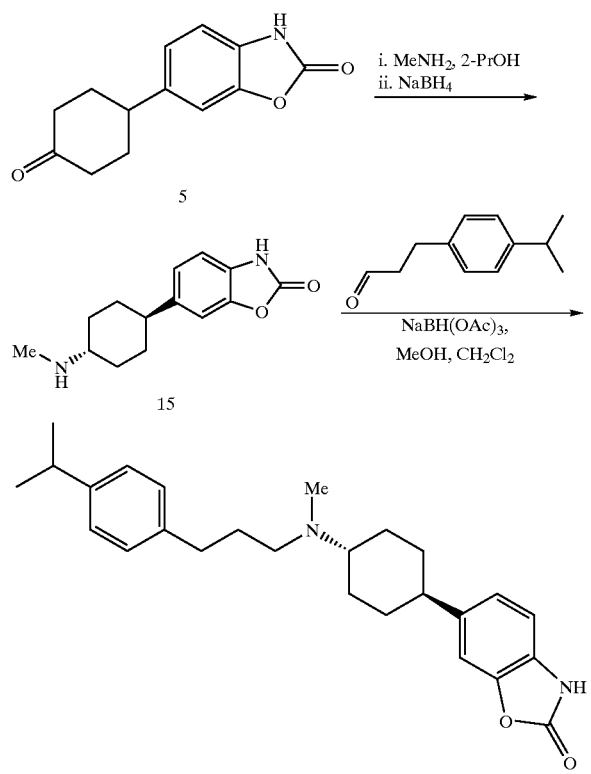

Step 1: To a suspension of ketone 5 (10.4 g, 0.045 mol) in 2-PrOH (520 mL) was added methylamine (33.7 mL of a 2.0 M solution in THF, 0.067 mol). A clear, amber solution formed after ca 15 minutes, and a precipitate gradually formed a few minutes later. After 1.5 hours, the reaction mixture was cooled in an ice/water bath, NaBH$_4$ (2.6 g, 0.067 mol) was added, and stirring was continued at 0° C. for 35 minutes. The reaction mixture was stirred at room temperature for 15 hours. MeOH (ca 2 mL) was added to quench any excess NaBH$_4$ (no gas evolution was observed), and the solvents were removed under reduced pressure. The residue was partitioned between 1N HCl (500 mL) and EtOAc (250 mL). The aqueous layer was separated, adjusted to pH 7–8 with solid NaHCO$_3$, and washed with EtOAc (200 mL). A precipitate formed during the wash, which was collected by vacuum filtration and dried to give 6-[trans-4-(methylamino)cyclohexyl]-3H-benzoxazol-2-one 15 (5.0 g, 46%). The organic layer was separated, and TLC analysis (89:10:1 CH$_2$Cl$_2$:MeOH:NH$_4$OH) showed it contained compound 15. Compound 15 was also shown by TLC analysis to be present in the initial EtOAc extraction. The organic extracts were combined, concentrated under reduced pressure, dissolved in a minimal amount of MeOH, and a solid was precipitated out with diethyl ether. The solid was collected by vacuum filtration and dried to give 15 (1.6 g, 13%) as the HCl salt. To the aqueous layer (ca 1L), which also showed the presence of additional 15 by TLC, was added solid NaCl (ca 80 g), and the solution was concentrated under reduced pressure to approximately half its original volume. A solid formed and was collected by vacuum filtration and dried to give 15 (1.3 g, 12%). The solids were combined to give 6-[trans-4-(methylamino)cyclohexyl]-3H-benzoxazol-2-one 15 (7.9 g, 73%): $^1$H NMR (500 MHz, CD$_3$OD): δ 7.10 (d, J=1.5 Hz, 1H), 7.03 (dd, J=8, 1.5 Hz, 1H), 6.98 (d, J=8 Hz, 1H), 2.67–2.52 (m, 2H), 2.49 (s, 3H), 2.15–2.12 (m, 2H), 1.97–1.94 (m, 2H), 1.61–1.52 (mi, 2H), 1.38–1.30 (m, 2H).

Step 2: To a solution of amine 15 (670 mg, 2.40 mmol) in 1:1 CH$_2$Cl$_2$:MeOH (30 mL) was added solid NaHCO$_3$ (200 mg, 2.40 mmol) and, after 10 minutes, 3-(4-isopropylphenyl)propionaldehyde (420 mg, 2.40 mmol). After stirring for 5 minutes, NaBH(OAc)$_3$ (760 mg, 3.60 mmol) was added, and the mixture was stirred at room temperature for 12 hours. The reaction mixture was brought to pH 8 with solid NaOH and concentrated under reduced pressure. Purification by flash chromatography (silica, 95:5 CH$_2$Cl$_2$:MeOH followed by 89:10:1 CH$_2$Cl$_2$:MeOH:NH$_4$OH), followed by formation of the HCl salt and recrystallization (MeOH:Et$_2$O) gave 6-(trans-4-{[3-(4-isopropylphenyl)-propyl]methylamino}cyclohexyl)-3H-benzoxazol-2-one (514 mg, 48%), as a white solid: mp 179–181° C.; IR (KBr): 2959, 1771, 1498, 1451 cm$^{-1}$; $^1$H NMR (500 MHz, DMSO-d$_6$): δ 11.48 (s, 1H), 10.10 (s, 1H), 7.17–7.15 (m, 5H), 7.00 (br s, 2H), 3.32–3.29 (m, 1H), 3.19–3.11 (m, 1H), 3.06–2.99 (m, 1H), 2.89–2.83 (m, 1H), 2.70 (d, J=4 Hz, 3H), 2.63–2.52 (m, 3H), 2.15–1.95 (m, 4H), 1.93–1.87 (m, 2H), 1.66–1.50 (m, 4H), 1.19 (d, J=7 Hz, 6H); ESI (m/z): 407 [M+H]$^+$; method B, 12.69 minutes (>99%); Anal. Calcd for C$_{26}$H$_{34}$N$_2$O$_2$.HCl: C, 70.49; H, 7.96; N, 6.32. Found: C, 70.29; H, 8.05; N, 6.28.

EXAMPLE 54

6-(trans-4-{[3-(2,4-Dichlorophenyl)propyl]methylamino}cyclohexyl)-3H-benzoxazol-2-one

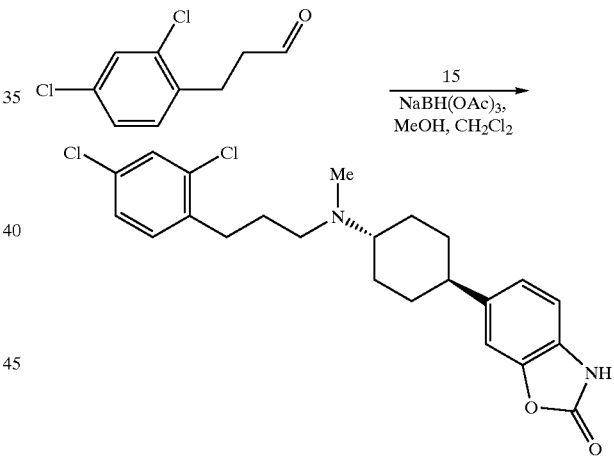

Condensation of 15 (550 mg, 1.9 mmol) and 3-(2,4-dichlorophenyl)-propionaldehyde (390 mg, 1.9 mmol) following the procedure described in Example 45, Step 2, followed by conversion to the HCl salt, gave 6-(trans-4-{[3-(2,4-dichlorophenyl)propyl]methylamino}cyclohexyl)-3H-benzoxazol-2-one (446 mg, 50%), as an off-white solid: mp 273–279° C.; IR (KBr): 2949, 1775, 1500, 1474 cm$^{-1}$; $^1$H NMR(500 MHz, DMSO-d$_6$): δ 11.49 (s, 1H), 10.01 (s, 1H), 7.61 (d, J=2 Hz, 1H), 7.47–7.41 (m, 2H), 7.17 (s, 1H), 7.00 (s, 2H), 3.34–3.29 (m, 1H), 3.22–3.17 (m, 1H), 3.11–3.03 (m, 1H), 2.79–2.73 (m, 2H), 2.71 (d, J=5 Hz, 3H), 2.59–2.48 (m, 1H), 2.14–2.06 (m, 2H), 2.03–1.97 (m, 2H), 1.94–1.88 (m, 2H), 1.69–1.50 (m, 4H); ESI (m/z): 433 [M+H]$^+$; HPLC: method A, 6.78 minutes (>99%); Anal. Calcd for C$_{23}$H$_{26}$Cl$_2$N$_2$O$_2$.HCl: C, 58.80; H, 5.79; N, 5.96. Found: C, 58.62; H, 5.76; N, 5.89.

EXAMPLE 55
6-(trans-4-{[3-(2,3,4-Trifluorophenyl)propyl]methylamino}cyclohexyl)-3H-benzoxazol-2-one

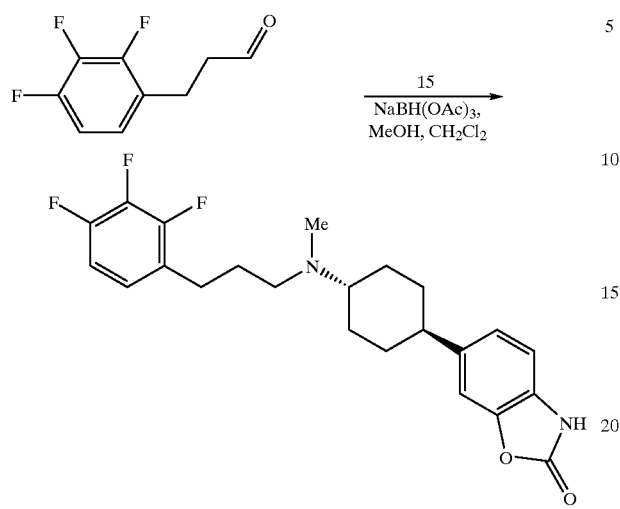

Condensation of 15 (420 mg, 1.5 mmol) and 3-(2,3,4-trifluorophenyl)-propionadehyde (280 mg, 1.5 mmol), following the procedure described in Example 45, Step 2, followed by conversion to the HCl salt, gave 6-(trans-4-{[3-(2,3,4-trifluorophenyl)propyl]methylamino}cyclohexyl)-3H-benzoxazol-2-one (257 mg, 33%), as an off-white solid: mp 269–274° C.; IR (KBr): 2950, 1768, 1513, 1485 cm$^{-1}$; $^1$H NMR (500 MHz, DMSO-d$_6$): δ 11.50 (s, 1H), 10.17 (s, 1H), 7.23–7.21 (m, 2H), 7.17 (br s, 1H), 7.00 (d, J=1 Hz, 2H), 3.33–3.26 (m, 1H), 3.21–3.14 (m, 1H), 3.08–3.01 (m, 1H), 2.79–2.71 (m, 2H), 2.69 (d, J=5 Hz, 3H), 2.59–2.50 (m, 1H), 2.16–1.98 (m, 4H), 1.94–1.87 (m, 2H), 1.68–1.50 (m, 4H); HRMS-APCI (m/z): [M+H]$^+$ calcd for C$_{23}$H$_{25}$F$_3$N$_2$O$_2$, 419.1946; found, 419.1948; HPLC: method A, 8.31 minutes (97.7%); method B, 11.85 minutes (97.8%); Anal. Calcd for C$_{23}$H$_{25}$F$_3$N$_2$O$_2$.HCl.0.25H$_2$O: C, 60.13; H, 5.81; N, 6.10. Found: C, 60.14; H, 5.70; N, 6.08.

EXAMPLE 56
6-(trans-4-{[3-(4-Isobutylphenyl)propyl]methylamino}cyclohexyl)-3H-benzoxazol-2-one

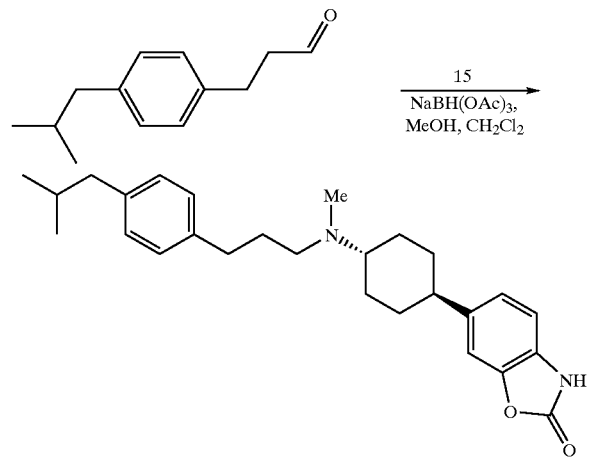

Condensation of 15 (1.0 g, 3.6 mmol) and 3-(4-isobutylphenyl)-propionaldehyde (700 mg, 3.6 mmol), following the procedure described in Example 45, Step 2, followed by conversion to the HCl salt, gave 6-(trans-4-{[3-(4-isobutylphenyl)propyl]methylamino}cyclohexyl)-3H-benzoxazol-2-one (977 mg, 61%), as an off-white solid: mp 162–165° C.; IR (KBr): 2953, 1773, 1498, 1451 cm$^{-1}$; $^1$H NMR (300 MHz, DMSO-d$_6$): δ 11.55 (s, 1H), 10.00 (s, 1H), 7.17–7.08 (m, 5H), 7.00 (s, 2H), 3.32–3.28 (m, 1H), 3.21–3.08 (m, 1H), 3.08–2.95 (m, 1H), 2.70 (d, J=5 Hz, 3H), 2.65–2.52 (m, 3H), 2.41 (d, J=7 Hz, 2H), 2.14–1.73 (m, 7H), 1.68–1.49 (m, 4H), 0.85 (d, J=7 Hz, 6H); HRMS-API (m/z): [M+H]$^+$ calcd for C$_{27}$H$_{36}$N$_2$O$_2$, 421.2855; found, 421.2858; HPLC: method A, 7.49 minutes (>99%); method B, 13.59 minutes (>99%); Anal. Calcd for C$_{27}$H$_{36}$N$_2$O$_2$.HCl.0.5H$_2$O: C, 69.58; H, 8.22; N, 6.01. Found: C, 69.23; H, 8.20; N, 5.87.

EXAMPLE 57
6-(trans-4-{[3-(2,4,6-Trifluorophenyl)propyl]methylamino}cyclohexyl)-3H-benzoxazol-2-one

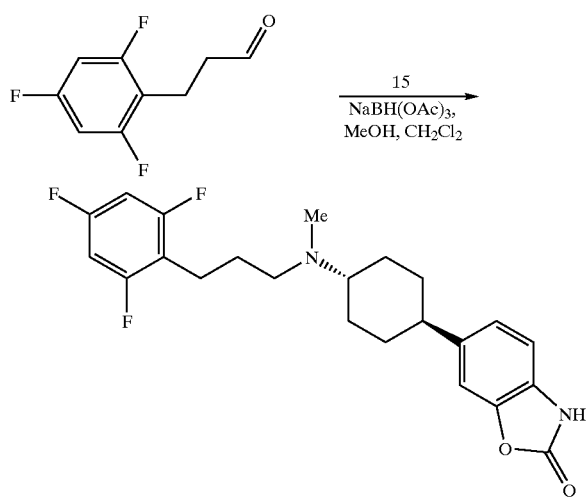

Condensation of 15 (460 mg, 1.9 mmol) and 3-(2,4,6-trifluorophenyl)-propionaldehyde (360 mg, 1.9 mmol), following the procedure described in Example 45, Step 2, followed by conversion to the HCl salt, gave 6-(trans-4-{[3-(2,4,6-trifluorophenyl)propyl]methylamino}cyclohexyl)-3H-benzoxazol-2-one (275 mg, 32%), as a white solid: mp 235–238° C.; IR (KBr): 2949, 1772, 1632, 1603 cm$^{-1}$; $^1$H NMR (300 MHz, DMSO-d$_6$): δ 11.54 (s, 1H), 9.78 (s, 1H), 7.26–7.18 (m, 3H), 7.00 (s, 2H), 3.32–3.27 (m, 1H), 3.26–3.04 (m, 2H), 2.71 (d, J=5 Hz, 3H), 2.58–2.54 (m, 1H), 2.66–2.62 (m, 2H), 2.12–1.86 (m, 6H), 1.68–1.48 (m, 4H); ESI (m/z): 419 [M+H]$^+$; HPLC: method A, 6.30 minutes (98.8%); Anal. Calcd for C$_{23}$H$_{25}$F$_3$N$_2$O$_2$.HCl: C, 60.73; H, 5.76; N, 6.16. Found: C, 60.43; H, 5.71; N, 5.99.

EXAMPLE 58
6-(4-{[3(trans-4-Dimethylaminophenyl)propyl]methylamino}cyclohexyl)-3H-benzoxazol2-one

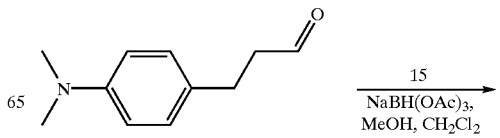

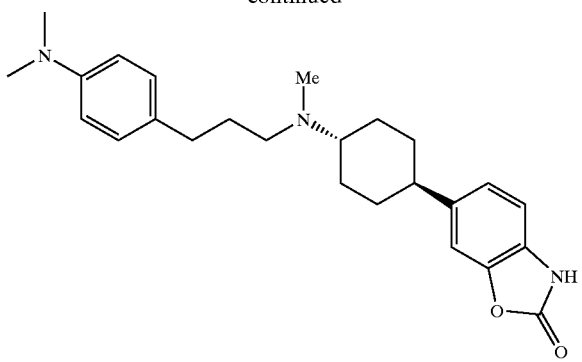

Condensation of 15 (2.22 g, 8.41 mmol) and 3-(4-dimethylaminophenyl)-propionaldehyde (910 mg, 5.14 mmol), following the procedure described in Example 45, Step 2, gave 6-(4-{[3-(trans-4-dimethylaminophenyl)propyl]-methylamino}cyclohexyl)-3H-benzoxazol-2-one (1.63 g, 78%), as an off-white solid: mp 182–184° C.; IR (KBr): 2930, 1772, 1491, 1448 cm$^{-1}$; $^1$H NMR (500 MHz, DMSO-d$_6$): δ 11.4 (br s, 1H), 7.15 (s, 1H), 7.02–6.95 (m, 4H), 6.66 (d, J=9 Hz, 2H), 2.84 (s, 6H), 2.54–2.44 (m, 6H), 2.20 (s, 1H), 1.83–1.81 (m, 4H), 1.68–1.63 (m, 2H), 1.50–1.32 (m, 4H); ESI (m/z): 408 [M+H]$^+$; HPLC: method A, 4.23 minutes (>99%); method B, 8.36 minutes (>99%); Anal. Calcd for C$_{25}$H$_{33}$N$_3$O$_2$·0.5H$_2$O: C, 72.08; H, 8.23; N, 10.09. Found: C, 72.48; H, 8.09; N, 10.09.

EXAMPLE 59

6-{trans-4-[Methyl(3-thiazol-2-ylpropyl)amino]cyclohexyl}-3H-benzoxazol-2-one

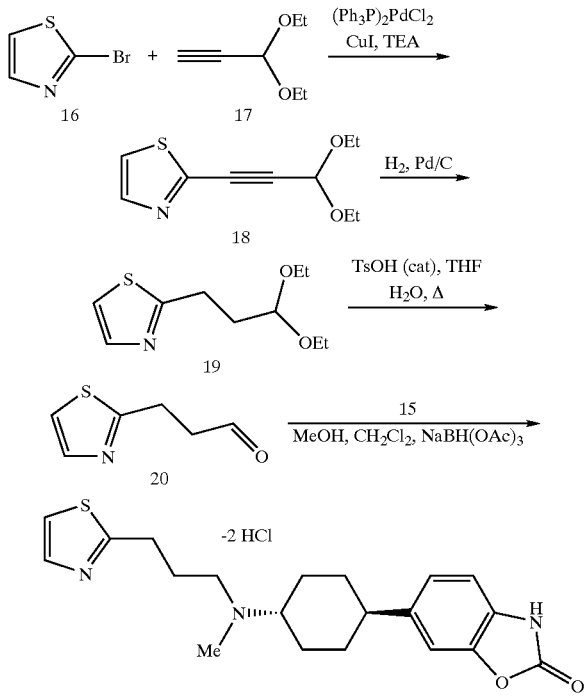

Step 1: To 2-bromothiazole 16 (5.0 g, 30 mmol) in DMF (40 mL) was added propiolaldehyde diethyl acetal 17 (4.4 g, 34 mmol), CuI (170 mg, 0.90 mmol), and triethylamine (8.4 mL, 60 mmol). The reaction mixture was deoxygenated with argon for 15 minutes, bis(triphenylphosphine)palladium (II) chloride (640 mg, 0.10 mmol) was added, and the mixture was deoxygenated again with argon for 15 minutes. After stirring at ambient temperature for 12 hours and then at 100° C. for 2.5 hours, the reaction was cooled to ambient temperature, diluted with EtOAc (500 mL), washed with water (3×150 mL), dried (Na$_2$SO$_4$), filtered, and concentrated under reduced pressure. Purification by flash chromatography (silica, 75:25 hexanes:EtOAc) gave alkyne 18 (3.4 g, 54%): $^1$H NMR (300 MHz, CDCl$_3$): δ 7.85 (d, J=3 Hz, 1H), 7.39 (d, J=3 Hz, 1H), 5.52 (s, 1H), 3.88–3.77 (m, 2H), 3.73–3.63 (m, 2H), 1.28 (t, J=7 Hz, 6H).

Step 2: A mixture of alkyne 18 (1.1 g, 5.0 mmol) and 10% Pd/C (100 mg) in EtOH (20 mL) were shaken under a H$_2$ atmosphere at 50 psi for 5 hours. The solution was filtered through Celite and concentrated under reduced pressure. The residue was dissolved in EtOH (20 mL), 10% Pd/C 100 mg) was added, and the mixture was shaken again under a H$_2$ atmosphere at 50 psi for 5 hours. The solution was filtered through Celite and concentrated under reduced pressure to give acetal 19 (900 mg, 84%): $^1$H NMR (300 MHz, CDCl$_3$): δ 7.68 (d, J=3 Hz, 1H), 7.19 (d, J=3 Hz, 1H), 4.57 (t, J=6 Hz, 1H), 3.74–3.63 (m, 2H), 3.57–3.45 (m, 2H), 3.11 (t, J=7 Hz, 2H), 2.14 (dt, J=14, 6 Hz, 2H), 1.21 (t, J=7 Hz 6H).

Step 3: To acetal 19 (450 mg, 2.1 mmol) in THF (10 mL) was added p-toluenesulfonic acid (20 mg, 0.10 mmol) and H$_2$O (0.20 mL). The reaction mixture was heated at reflux for 45 minutes, cooled to ambient temperature, and concentrated under reduced pressure. Purification by flash chromatography (silica, 75:25 hexanes:EtOAc) gave aldehyde 20 (200 mg, 30%): $^1$H NMR (300 MHz, CDCl$_3$): δ 9.88 (s, 1H), 7.67 (d, J=3 Hz, 1H), 7.22 (d, J=3 Hz, 1H), 7.22 (d, J=3 Hz, 1H), 3.36 (t, J=7 Hz, 2H), 3.04 (t, J=7 Hz, 2H).

Step 4: Condensation of 15 (200 mg, 1.40 mmol) and aldehyde 20 (340 mg, 1.40 mmol), following the procedure described in Example 45, Step 2, followed by conversion to the HCl salt, gave 6-{trans-4-[methyl(3-thiazol-2-ylpropyl)-amino]cyclohexyl}-3H-benzoxazol-2-one (311 mg, 50%), as an off-white solid: mp 237–239° C.; IR (KBr): 2948, 1767, 1499, 1449 cm$^{-1}$; $^1$H NMR (500 MHz, CD$_3$OD): δ 8.04 (dd, J=4, 1 Hz, 1H), 7.87 (dd, J=4, 1 Hz, 1H), 7.14 (s, 1H), 7.08–6.99 (m, 2H), 3.53–3.20 (m, 5H), 2.89 (s, 3H), 2.69–2.61 (m, 1H), 2.40–2.26 (m, 2H), 2.24–2.14 (m, 2H), 2.10–2.01 (m, 2H), 1.86–1.61 (m, 4H); APCI (m/z): 372 [M+H]$^+$; HPLC: method A, 5.34 minutes (>99%); Anal. Calcd for C$_{20}$H$_{25}$N$_3$O$_2$S·2HCl: C, 54.05; H, 6.12; N, 9.46. Found: C, 53.82; H, 6.21; N, 9.22.

EXAMPLE 60

6-(trans-4-{Methyl-[2-(Methylphenylamino)ethyl]amino}cyclohexyl)-3H-benzoxazol-2-one

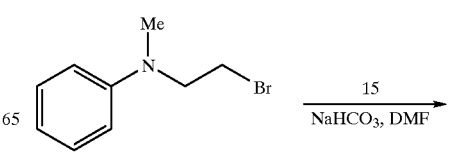

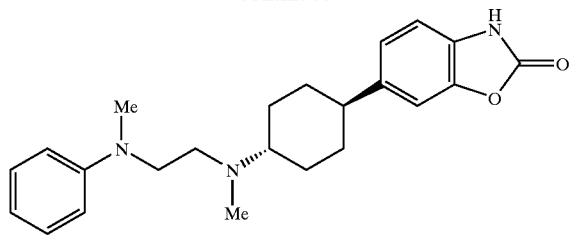

Step 1: To a solution of amine 2 (780 mg, 3.2 mmol) in DMF (15 mL) was added NaHCO$_3$ (560 mg, 6.7 mmol) and (2-bromoethyl)methylphenylamine (690 mg, 3.2 mmol). The reaction mixture was gradually heated to 100° C., held at 100° C. for 2.5 hours, and then stirred at 50° C. for 12 hours. The suspension was cooled to room temperature, diluted with H$_2$O (35 mL), and extracted with EtOAc (3×50 mL). The combined organics were washed with saturated NaCl (50 mL), dried (Na$_2$SO$_4$), filtered, and concentrated under reduced pressure. Purification by flash chromatography (silica, 89:10:1 CH$_2$Cl$_2$:MeOH:NH$_4$OH) followed by formation of the HCl salt and recrystallization (MeOH:Et$_2$O) gave 6-(trans-4-{methyl-[2-(methylphenylamino)ethyl]amino}cyclohexyl)-3H-benzoxazol-2-one (350 mg, 24%), as a white solid: mp 240–243° C.; IR (KBr): 2950, 1765, 1499, 1451 cm$^{-1}$; $^1$H NMR (500 MHz, DMSO-d$_6$): δ 8.72 (br s, 2H), 7.19–7.07 (m, 5H), 6.64 (d, J=8 Hz, 2H), 6.57 (t, J=11 Hz, 1H), 3.97 (t, J=6 Hz, 2H), 3.67 (t, J=6 Hz, 2H), 3.02–2.96 (m, 1H), 2.84 (s, 3H), 2.55 (m, 4H), 2.13 (br d, J=10 Hz, 2H), 1.88 (br d, J=10 Hz, 2H), 1.54–1.42 (m, 4H); HRMS-API (m/z): [M+H]$^+$ calcd for C$_{23}$H$_{29}$N$_3$O$_2$, 380.2338; found, 380.2339; HPLC: method A, 6.37 minutes (93.4%); method B, 11.60 minutes (93.0%); Anal. Calcd for C$_{23}$H$_{29}$N$_3$O$_2$.2HCl.0.25H$_2$O: C, 60.46; H, 6.95; N, 9.20. Found: C, 60.65; H, 6.98; N, 9.12.

Scheme 4
Preparation of 6-(4-Oxocyclohexyl)-3H-benzothiazol-2-one 25

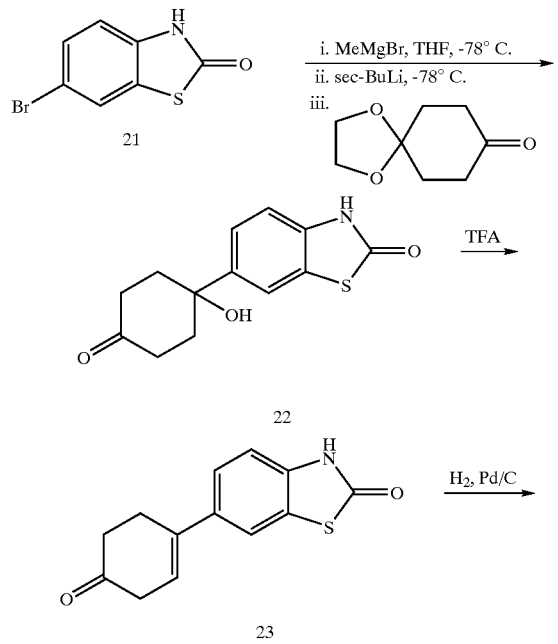

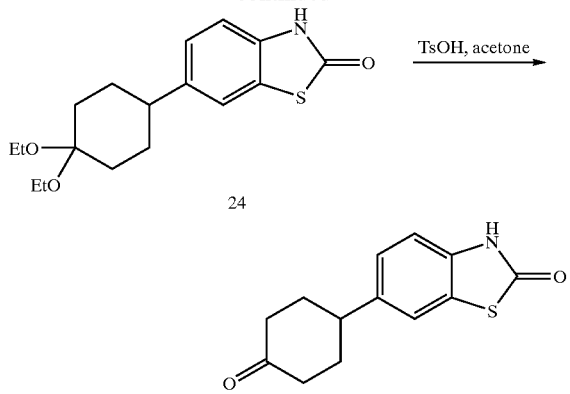

Step 1: Bromide 21 (2.88 g, 12.52 mmol) was dissolved in anhydrous THF (50 mL), and the solution was cooled to −78° C. Solutions of MeMgBr (4.59 mL of a 3.0 M solution in Et$_2$O, 13.77 mmol), sec-BuLi (10.59 mL of a 1.3 M solution in cyclohexane, 13.77 mmol), and 1,4-cyclohexanedione mono-ethylene ketal (1.95 g, 12.52 mmol) in anhydrous THF (10 mL) were added sequentially at 30-minute intervals. After the final addition, the reaction mixture was allowed to warm to room temperature. The reaction was quenched by the addition of 1N HCl (25 mL). The reaction mixture was diluted with EtOAc (300 mL), washed with saturated NaCl (250 mL), dried (Na$_2$SO$_4$), filtered, and concentrated under reduced pressure. Purification by silica gel chromatography (eluent 1:1 Hexanes:EtOAc) gave alcohol 22 (1.81 g, 47%), as a white solid: $^1$H NMR (500 MHz, CDCl$_3$): δ 8.48 (br s, 1H), 7.59 (s, 1H), 7.31 (d, J=5 Hz, 1H), 7.04 (d, J=5 Hz, 1H), 2.17–2.04 (m, 4H), 1.81 (d, J=8 Hz, 2H), 1.77 (d, J=8 Hz, 2H).

Step 2: Alcohol 22 (1.81 g, 5.90 mmol) was stirred in TFA (8 mL) at room temperature for 20 minutes. The red solution was poured into CHCl$_3$ (200 mL), and the organic layer was washed with H$_2$O (2×100 mL), saturated NaHCO$_3$ and saturated NaCl, dried (Na$_2$SO$_4$), filtered, and concentrated under reduced pressure to give ketone 23 (1.22 g, 85%), as a white solid: $^1$H NMR (500 MHz, DMSO-d$_6$): δ 7.42 (s, 1H), 7.34 (d, J=6 Hz, 1H), 7.08 (d, J=6 Hz, 1H), 6.11 (t, J=5 Hz, 1H), 3.04 (d, J=2 Hz, 2H), 2.87 (t, J=7 Hz, 2H), 2.57 (m, 2H).

Step 3: A solution of ketone 23 (1.22 g, 4.98 mmol) and 10% Pd/C (0.25 g) in a 3:2 mixture of EtOAc:EtOH (150 mL) was shaken under a H$_2$ atmosphere at 50 psi for 4 hours. The solution was filtered through Celite and concentrated under reduced pressure. Purification by flash chromatography (eluent 1.5:1 Hexanes:EtOAc) gave ketal 24 (1.44 g, 98%) as a white solid: $^1$H NMR (500 MHz, CD$_3$OD): δ 7.31 (s, 1H), 7.13 (d, J=6 Hz, 1H), 7.04 (d, J=6 Hz, 1H), 3.53 (q, J=7 Hz, 2H), 3.48 (q, J=7 Hz, 2H), 2.57 (m, 1H), 2.10 (d, J=10 Hz, 2H), 1.76–1.51 (m, 4H), 1.47 (m, 2H), 1.21 (t, J=7 Hz, 3H), 1.18 (t, J=7 Hz, 3H).

Step 4: Ketal 24 (0.6 g, 1.9 mmol) and TsOH (0.36 g, 1.89 mmol) were stirred in acetone (20 mL) overnight. The reaction mixture was diluted with EtOAc (100 mL) and washed with H$_2$O (50 mL) and saturated NaHCO$_3$ (50 mL). The organic layer was concentrated under reduced pressure to give 6-(4-oxocyclohexyl)-3H-benzothiazol-2-one 25 (0.48 g, 98%) as a white solid: $^1$H NMR (500 MHz, CD$_3$OD): δ 7.41 (s, 1H), 7.21 (d, J=6 Hz, 1H), 7.06 (d, J=6 Hz, 1H), 3.13 (m, 1H), 2.53 (m, 2H), 2.31 (m, 2H), 2.14 (m, 2H), 1.96 (m, 2H).

EXAMPLE 61

(a) 6-{trans-4-[3-(4-Fluorophenyl)propylamino] cyclohexyl}-3H-benzthiazol-2-one (b) 6-(trans-4-{[3-(4-Fluorophenyl)propyl] methylamino}cyclohexyl)-3H-benzthiazol-2-one

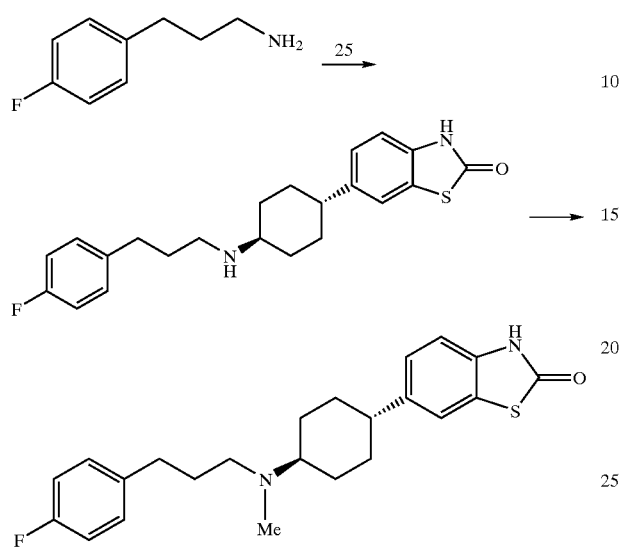

Step 1: To a solution of ketone 25 (2.3 g, 9.3 mmol) in 2-propanol (30 mL) was added 4 Å molecular sieves and 3-(4-fluorophenyl)-1-propylamine (1.76 g, 9.3 mmol). The reaction mixture was stirred for 4 hours. Sodium borohydride (0.49 g, 13.03 mmol) was added, and the reaction mixture was stirred overnight, quenched with MeOH, and concentrated under reduced pressure. Purification by flash chromatography (silica, 9.5:5:1 $CH_2Cl_2$:MeOH:$NH_4OH$) gave 6-{trans-4-[3-(4-fluorophenyl)propylamino] cyclohexyl}-3H-benzthiazol-2-one (0.24 g, 7%): $^1$H NMR (500 MHz, DMSO-$d_6$): δ 7.39 (s, 1H), 7.25–7.06 (m, 6H), 3.01 (m, 1H), 2.86 (t, J=8 Hz, 2H), 2.61 (t, J=8 Hz, 2H), 2.37 (m, 1H), 2.01 (m, 2H), 1.92–1.81 (m, 4H), 1.49–1.36 (m, 4H).

Step 2: To a stirred solution of 6-{trans-4-[3-(4-fluorophenyl)-propylamino]cyclohexyl}-3H-benzthiazol-2-one (0.24 g, 0.67 mmol) in MeOH (10 mL) containing $H_2O$ (0.5 mL) was added p-formaldehyde (0.1 g, 3.3 mmol). The reaction mixture was stirred for 3 hours. Sodium triacetoxyborohydride (0.2 g, 0.9 mmol) was added, and the mixture was stirred overnight. Solid NaOH was added until the solution became clear. The reaction mixture was concentrated under reduced pressure to give a yellow oil. Purification by flash chromatography (eluent 9.5:1:1 $CH_2Cl_2$:MeOH:$NH_4OH$) gave 6-(trans-4-{[3-(4-fluorophenyl)-propyl]methylamino}cyclohexyl)-3H-benzthiazol-2-one (55 mg, 15%), as a pale yellow solid: mp 256–261° C.; IR (KBr): 2942, 1683, 1509 cm$^{-1}$; $^1$H NMR (500 MHz, DMSO-$d_6$): δ 7.41 (s, 1H), 7.31–7.03 (m, 6H), 3.29 (m, 2H), 3.01 (m, 2H), 2.70 (s, 3H), 2.64 (m, 2H), 2.11 (m, 1H), 2.08 (m, 1H), 1.99 (m, 2H), 1.87 (m, 2H), 1.98–1.61 (m, 4H); API-MS (m/z): 399 [M+H]$^+$; calcd for $C_{23}H_{27}FN_2OS$, 399.1906; found, 399.1909; HPLC: method A, 5.85 minutes (>99%); method B, 11.48 minutes (>99%); Anal. Calcd for $C_{23}H_{27}FN_2OS \cdot HCl \cdot 0.75NaCl$: C, 57.69; H, 5.89; N, 5.85. Found: C, 57.72; H, 5.96; N, 5.51.

Scheme 5
Preparation of 5-(4-Oxocyclohexyl)-1,3-dihydrobenzoimidazol-2-one 29

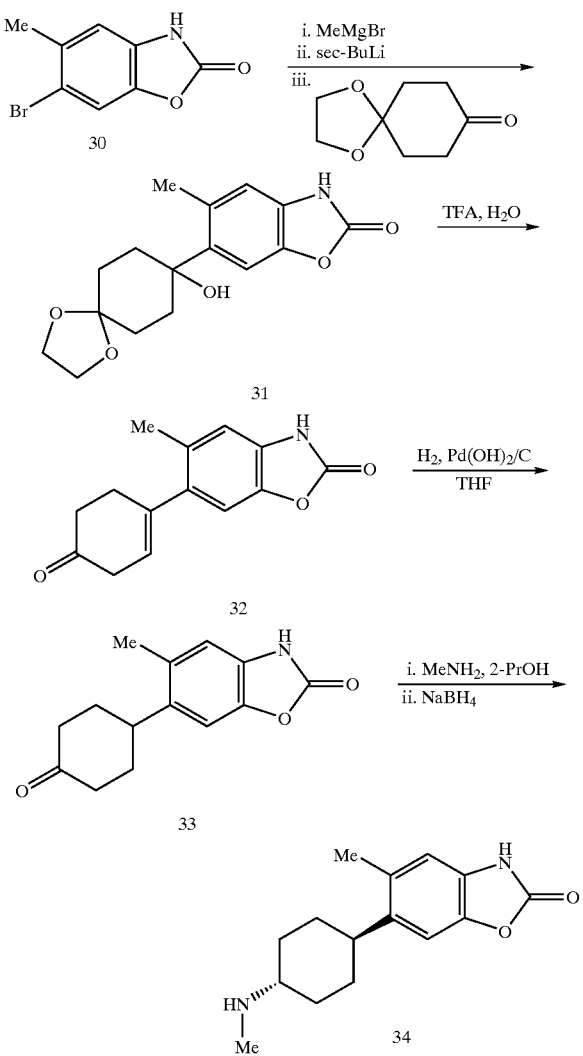

Step 1: N-Bromosuccinimide (112.0 g, 0.63 mol) was added to a stirred solution of 2-hydroxybenzimidazole 26 (84.4 g, 0.63 mol) in glacial acetic acid (930 mL), and the mixture was stirred at room temperature for 12 hours. The reaction mixture was poured into $H_2O$ (3 L), and the yellow solid that formed was collected. Trituration with hot EtOH (1.5 L) gave bromide 27 (113.2 g, 85%), as yellow solid: $^1$H NMR (300 MHz, DMSO-$d_6$): δ 10.75 (s, 2H), 7.11–7.05 (m, 2H), 6.87 (d, J=9 Hz, 2H).

Step 2: Bromide 27 (25.0 g, 0.12 mol) was dissolved in anhydrous THF (1.5 L) and the solution was cooled in a −78° C. dry ice/2-PrOH bath. A solution of MeMgBr (43.0 mL of a 3.0 M solution in $Et_2O$, 0.13 mol) was added dropwise over 10 minutes, (internal temperature maintained −60° C.). After stirring at −78° C. for 1 hour, t-BuLi (289.4 mL of a 1.7 M solution in pentane, 0.49 mol) was added dropwise over 0.5 hours (again, temperature was maintained below −60° C.). After 0.75 hours, 1,4-Cyclohexanedione mono-ethylene ketal (37.5 g, 0.24 mol) in anhydrous THF (120 mL) was added over 10 minutes. After 0.5 hours, the reaction mixture was warmed to 0° C. The reaction was quenched by the addition of saturated aqueous $NH_4Cl$ (210 mL), and the solution was warmed to room temperature.

Most of the THF was removed under reduced pressure, 1N HCl (500 mL) was added, and mixture was extracted with EtOAc (5×200 mL). The combined organics were dried (Na$_2$SO$_4$), filtered, and concentrated under reduced pressure. The residue was slurried in EtOAc, and the resulting solid was collected by vacuum filtration and dried (21.4 g). This solid was stirred in TFA (50 mL) at room temperature for 20 minutes. The red solution was poured into CHCl$_3$ (400 mL) and H$_2$O (400 mL). A gelatinous solid formed which was collected by vacuum filtration, rinsed with H$_2$O (150 mL), and dried to give crude 28 (25.5 g, 92%). $^1$H NMR (300 MHz, DMSO-d$_6$): δ 10.78 (s, 1H), 10.60 (s, 1H), 7.01–6.85 (m, 3H), 6.05–6.00 (m, 1H), 3.05–3.00 (m, 2H), 2.88–2.79 (m, 2H), 2.59–2.52 (m, 2H).

Step 3: A mixture of crude 28 (0.85 g, 3.7 mmol) and 10% Pd/C (0.15 g) in EtOH (30 L) was shaken under a H$_2$ atmosphere at 50 psi for 3 hours. The solution was filtered through Celite and concentrated under reduced pressure to give crude 5-(4-oxocyclohexyl)-1,3-dihydrobenzimidizol-2-one 29 (850 mg, 99%): $^1$H NMR (300 MHz, DMSO-d$_6$): δ 6.95–6.80 (m, 3H), 3.07–2.95 (m, 1H), 2.67–2.48 (m, 2H), 2.32–2.22 (m, 2H), 2.09–1.97 (m, 2H), 1.90–1.65 (m, 2H).

EXAMPLE 62
5-{trans-4-[3-(4-Fluorophenyl)propylamino]cyclohexyl}-1,3-dihydrobenzoimidazol-2-one

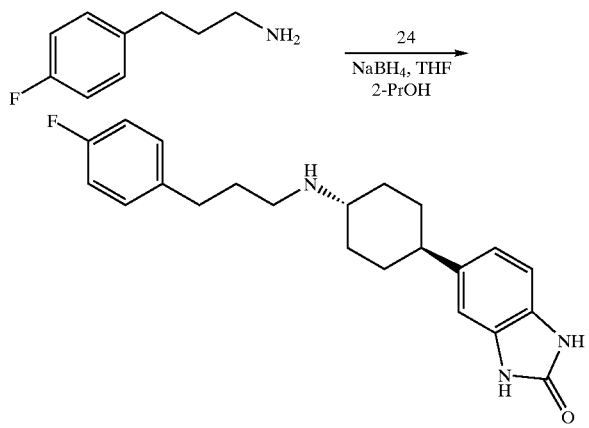

To a solution of (4-fluorophenyl)-1-propylamine (1.9 g, 10.0 mmol) in 2-propanol (90 mL) and THF (25 mL) was added Et$_3$N (1.5 mL, 11.0 mmol), ketone 24 (2.3 g, 10.0 mmol), and 3 Å molecular sieves. The reaction mixture was stirred at room temperature for 3 hours. Sodium borohydride (950 mg, 25.1 mmol) was added, and the reaction mixture was stirred for 12 hours. Additional sodium borohydride (500 mg, 13.2 mmol) was added, and the reaction mixture was stirred for 12 hours. Methanol was added to quench the excess NaBH$_4$, and the resultant solution was filtered through a pad of Celite and concentrated under reduced pressure. Purification by flash chromatography (silica, 90:10 CH$_2$Cl$_2$:MeOH followed by 95:4.5:0.5 CH$_2$Cl$_2$:MeOH:NH$_4$OH), followed by formation of the HCl salt and recrystallization (MeOH:Et$_2$O), gave 5-{trans-4-[3-(4-fluorophenyl)-propylamino]cyclohexyl}-1,3-dihydrobenzoimidazol-2-one (162 mg, 4%) as a white solid: mp 336–339° C.; IR (KBr): 2943, 1727, 1686, 1510 cm$^{-1}$; $^1$H NMR (500 MHz, DMSO-d$_6$): δ 10.45 (s, 1H), 10.39 (s, 1H), 8.55 (s, 2H), 7.29–7.27 (m, 2H), 7.15–7.12 (m, 2H), 6.83–6.76 (m, 3H), 3.13–3.06 (m, 1H), 2.97–2.89 (m, 2H), 2.68 (t, J=8 Hz, 2H), 2.48–2.44 (m, 1H), 2.15–2.08 (m, 2H), 1.97–1.82 (m, 4H), 1.54–1.43 (m, 4H); API (m/z): 368 [M+H]$^+$; HPLC: method A, 5.07 minutes (98.8%); method B, 11.00 minutes (98.9%); Anal. Calcd for C$_{22}$H$_{26}$FN$_3$O.HCl.0.25H$_2$O: C, 64.70; H, 6.79; N, 10.29. Found: C, 64.79; H, 6.74; N, 10.12.

EXAMPLE 63
5-(trans-4-{[3-(4-Fluorophenyl)propyl]methylamino}cyclohexyl)-1,3-dihydrobenzoimidazol-2-one

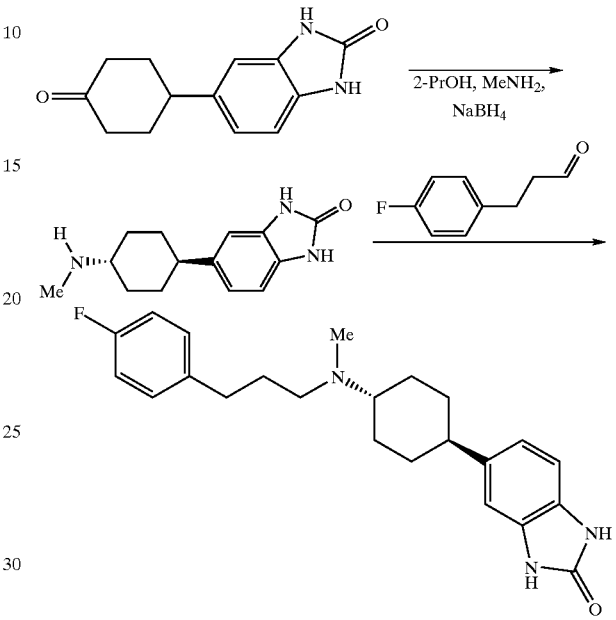

Step 1: To a suspension of ketone 29 (2.15 mg, 9.4 mmol) in 2-PrOH (115 mL, HPLC grade) was added methylamine (7.1 mL of a 2.0 M solution in THF, 14.2 mmol). After 1 hour, the reaction mixture was cooled in an ice/water bath and sodium borohydride (530 mg, 14.0 mmol) was added. The mixture was allowed to warm to room temperature and stirred for 12 hours. Methanol (ca 2 mL) was added to quench any excess sodium borohydride, and the solvents were removed under reduced pressure. Purification by flash chromatography (silica, 89:10:1 CH$_2$Cl$_2$:MeOH:NH$_4$OH) followed by formation of the HCl salt and recrystallization (MeOH:Et$_2$O) gave 5-(4-methylaminocyclohexyl)-1,3-dihydrobenzoimidazol-2-one (402 mg, 13%): $^1$H NMR (500 M, DMSO-d$_6$): δ 10.58 (s, 1H), 10.51 (s, 1H), 8.81 (s, 2H), 6.99–6.71 (m, 3H), 3.05–2.90 (m, 1H), 2.20–2.09 (m, 2H), 2.48–2.50 (m, 4H), 1.95–1.85 (m, 2H), 1.57–1.39 (m, 4H).

Step 2: To a suspension of 5-(4-methylaminocyclohexyl)-1,3-dihydrobenzoimidazol-2-one (400 mg, 1.4 mmol) in 1:1 CH$_2$Cl$_2$:MeOH (32 mL) was added 3-(4-fluorophenyl)propionaldehyde (220 mg, 1.4 mmol) and, after 5 minutes, NaBH(OAc)$_3$ (420 mg, 2.0 mmol). After 12 hours NaBH(OAc)$_3$ (300 mg, 1.4 mmol) was added and stirring continued for 8.25 hours. The reaction mixture was brought to pH 8 with solid NAOH and concentrated under reduced pressure. Purification by flash chromatography (silica, 95:4.5:0.5 CH$_2$Cl$_2$:MeOH:NH$_4$OH) and formation formation of the HCl salt gave 5-(trans-4-({[3-(4-fluorophenyl)propyl]methylamino}cyclohexyl)-1,3-dihydrobenzoimidazol-2-one (330 mg, 56%), as an off-white foam: IR (KBr): 2949, 1696 cm$^{-1}$; $^1$H NMR (500 MHz, DMSO-d$_6$): δ 10.52 (s, 1H), 10.48 (s, 1H), 10.42 (s, 1H), 7.31–7.28 (m, 2H), 7.17–7.11 (m, 2H), 6.87–6.76 (m, 3H), 3.35–3.25 (m, 1H), 3.18–3.09 (m, 1H), 3.02–2.59 (m, 1H), 2.71–2.61 (m, 5H), 2.48–2.45 (m, 1H), 2.19–1.99 (m, 4H), 1.92–1.85 (m, 2H), 1.68–1.49

(m, 4H); ESI (m/z) 382 [M+H]+; HRMS-API (m/z): [M+H]+ calcd for $C_{23}H_{28}FN_3O$, 382.2294; found, 382.2292; method A, 5.64 minutes (>99%); method B, 10.82 minutes (>99%); Anal. Calcd for $C_{23}H_{28}FN_3O·HCl·0.75H_2O$: C, 64.03; H, 7.13; N, 9.74. Found: C, 63.89; H, 7.22; N, 9.50.

Scheme 6
Preparation of 5-Methyl-6-
(trans-4-methylaminocyclohexyl)-3H-benzoxazol-2-one 34

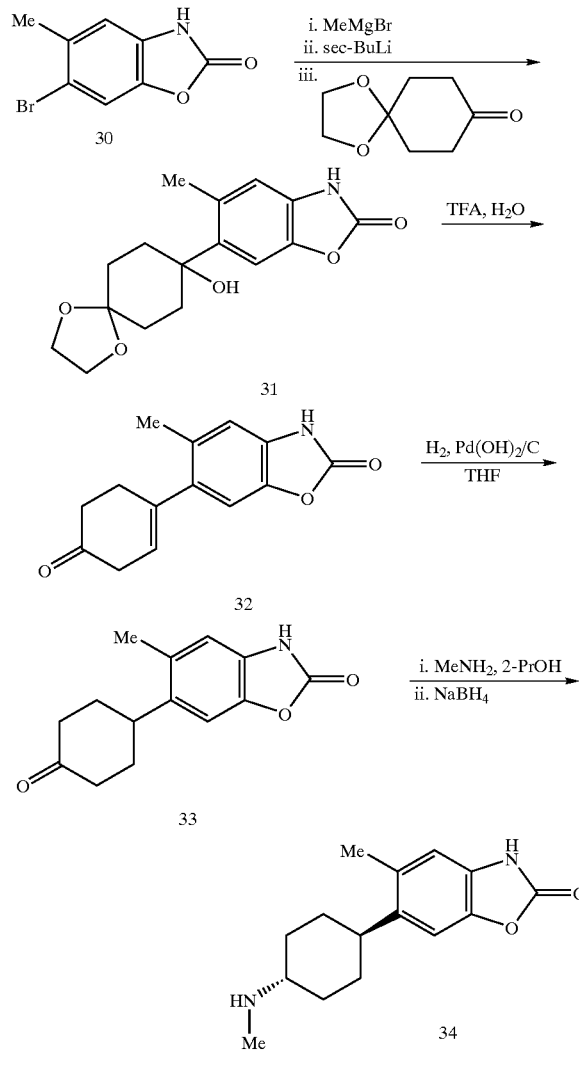

Step 1: Bromide 30 (5.0 g, 21.9 mmol) was dissolved in anhydrous THF (85 mL), and the solution was cooled to −78° C. Solutions of MeMgBr (8.03 mL of a 3.0 M solution in Et$_2$O, 24.1 mmol), sec-BuLi (18.5 mL of a 1.3 M solution in cyclohexane, 24.1 mmol), and 1,4-cyclohexanedione monoethylene ketal (3.76 g, 24.1 mmol) in anhydrous THF (20 mL) were added sequentially at 30-minute intervals. After the final addition, the reaction mixture was allowed to warm to room temperature. The reaction mixture was diluted with EtOAc (500 mL), washed with saturated NaCl (200 mL), and the water layer was extracted with EtOAc (200 mL) and CH$_2$Cl$_2$ (200 mL). The combined organic layers were dried (Na$_2$SO$_4$), filtered, and concentrated under reduced pressure to provide a crude solid which was purified by flash chromatography (silica, 10% MeOH:CH$_2$Cl$_2$) to yield 31 (2.96 g, 44%) as a white solid: $^1$H NMR (500 MHz, CDCl$_3$): δ 8.85 (br s, 1H), 7.38 (s, 1H), 6.83 (s, 1H), 4.03–3.90 (m, 4H), 2.61 (s, 3H), 2.23 (dt, J=13, 4 Hz, 2H), 2.12 (dt, J=13, 4 Hz, 2H), 1.96–1.90 (m, 2H), 1.73–1.61 (m, 2H).

Step 2: Compound 31 was stirred in TFA (12 mL) and H$_2$O (3 mL) and slowly warmed from 0° C. to room temperature over 3.5 hours. The red solution was poured into CHCl$_3$ (300 mL), and the organic layer was washed with H$_2$O (2×100 mL), saturated NaHCO$_3$, and saturated NaCl, dried (Na$_2$SO$_4$), filtered, and concentrated under reduced pressure to give 32 (2.13 g, 91%), as a white solid: $^1$H NMR (500 MHz, CD$_3$OD): δ 6.98 (s, 1H), 6.91 (s, 1H), 5.68 (t, J=3 Hz, 1H), 3.06–3.02 (m, 2H), 2.73–2.65 (m, 2H), 2.64–2.61 (m, 2H), 2.34 (s, 3H).

Step 3: A mixture of 32 (1.64 g, 6.74 mmol) in THF (100 mL) and 20% Pd(OH)$_2$/C (490 mg) was shaken under a H$_2$ atmosphere at 50 psi for 12 hours. The solution was filtered through Celite and concentrated under reduced pressure to give 33 (1.70 g, 100%) as a pale yellow solid: $^1$H NMR (500 MHz, CD$_3$OD): δ 7.11 (s, 1H), 6.90 (s, 1H), 3.36 (tt, J=13, 3 Hz, 1H), 2.65 (dt, J=13, 6 Hz, 2H), 2.45–2.39 (m, 5H), 2.15–2.08 (m, 2H), 1.90 (ddd, J=17, 13, 4 Hz, 2H).

Step 4: Condensation of 33 (1.65 g, 6.74 mmol) with methylamine (5.06 mL, 10.1 mmol) and NaBH$_4$ (382 mg, 10.1 mmol) in 2-propanol (28 mL), following the procedure described in Example 63, Step 1, gave 5-methyl-6-(trans-4-methylaminocyclohexyl)-3H-benzoxazol-2-one (34) (207 mg, 12%), as a white solid: $^1$H NMR (500 MHz, DMSO-d$_6$): δ 7.08 (s, 1H), 6.82 (s, 1H), 2.63 (tt, J=12, 3 Hz, 1H), 2.35 (tt, J=11, 4 Hz, 1H), 2.32 (s, 3H), 2.28 (s, 3H), 1.98 (br d, J=12 Hz, 2H), 1.68 (br d, J=12 Hz, 2H), 1.44 (ddd, J=16, 13, 3 Hz, 2H), 1.13 (ddd, J=16, 13, 3 Hz, 2H).

EXAMPLE 64

6-(4-{[3-(4-Fluorophenyl)propyl]methyl-amino}cyclohexyl)-5-methyl-3H-benzoxazol-2-one

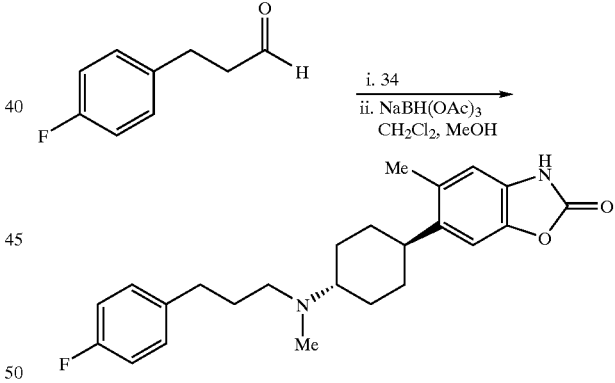

Condensation of 5-methyl-6-(trans-4-methylaminocyclohexyl)-3H-benzoxazol-2-one 34 (0.20 g, 0.77 mmol) with 3-(4-fluorophenyl)-propionaldehyde 25 (0.13 g, 0.85 mmol) and NaBH(OAc)$_3$ (229 mg, 1.08 mmol) in CH$_2$Cl$_2$ (4 mL) and MeOH (4 mL), following the procedure described in Example 63, Step 2, gave 6-(4-{[3-(4-fluorophenyl)propyl]methyl-amino}cyclohexyl)-5-methyl-3H-benzoxazol-2-one (190 mg, 62%), as a white solid: mp 264–267° C.; IR (KBr): 2953, 1765, 1510, 1491 cm$^{-1}$; $^1$H NMR (500 MHz, DMSO-d$_6$): δ 11.40 (s, 1H), 10.01 (s, 1H), 7.31 (dd, J=8, 6 Hz, 2H), 7.14 (t, J=9 Hz, 2H), 7.11 (s, 1H), 6.88 (s, 1H), 3.35–3.28 (m, 1H), 3.19–3.12 (m, 1H), 3.05–2.98 (m, 1H), 2.72 (d, J=5 Hz, 3H), 2.69–2.62 (m, 2H), 2.53–2.46 (m, 1H), 2.29 (s, 3H), 2.14–1.97 (m, 4H), 1.85–1.78 (m, 2H), 1.72–1.50 (m, 4H); ESI (m/z): 397 [M+H]+; HPLC: method A, 6.37 minutes (>99%); Anal.

Calcd for $C_{24}H_{29}FN_2O_2 \cdot HCl$: C, 66.58; H, 6.98; N, 6.47. Found: C, 66.47; H, 7.02; N, 6.32.

Scheme 7
Preparation of 5-Methoxy-6-(4-methylaminocyclohexyl)-3H-benzoxazol-2-one 42

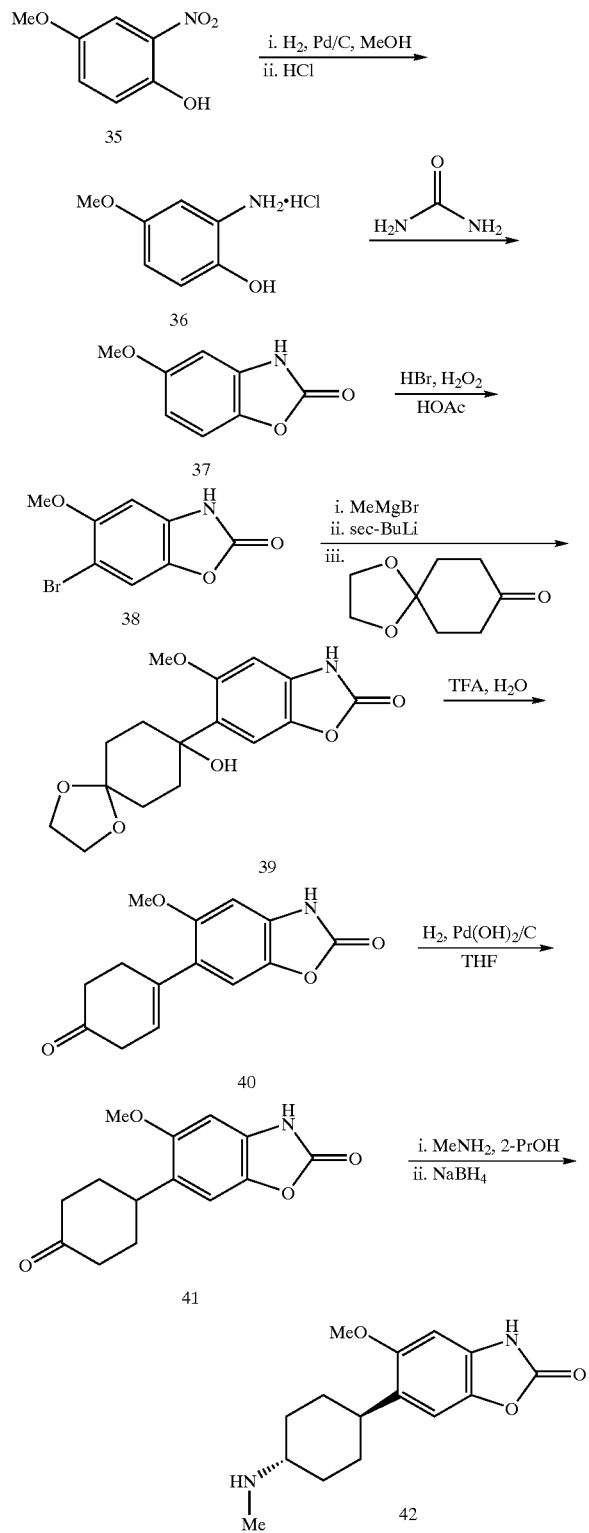

Step 1: To a solution of 4-methoxy-2-nitrophenol 35 (10.0 g, 59.1 mmol) in MeOH (500 mL) was added 10% Pd/C (1.0 g), and the reaction was stirred under a $H_2$ atmosphere at balloon pressure for 4 hours. The reaction was acidified with HCl (60 mL of a 1N solution in $Et_2O$, 60 mmol), and then filtered through Celite. Concentration under reduced pressure gave 36 (10.4 g, 100%), which was used without further purification: $^1$H NMR (500 MHz, $CD_3OD$): δ 6.96–6.87 (m, 3H), 3.75 (s, 3H).

Step 2: A mixture of salt 36 (10.3 g, 58.7 mmol) and urea (5.64 g, 93.9 mmol) was heated at 180° C. for 2 hours. After the reaction was cooled to room temperature, 1N HCl was added, and the water layer was extracted with EtOAc. The organic layer was dried ($Na_2SO_4$) and filtered. Concentration under reduced pressure gave 37 (7.46 g, 77%), which was used without further purification: $^1$H NMR (300 MHz, $CD_3OD$): δ 7.14–7.06 (m, 1H) 6.68–6.62 (m, 2H), 3.78 (s, 3H).

Step 3: To a solution of 37 (8.27 g, 50.1 mmol) in HOAc (30 mL) were added hydrogen bromide (22.9 mL, 115 mmol) and hydrogen peroxide (6.55 mL, 64.1 mmol) at 10° C. The reaction was allowed to warm to room temperature and then stirred 1 hour. Water (50 mL) was added to the reaction mixture. The dark gray solid which formed was collected by filtration, and then washed with $H_2O$ (50 mL). The crude solid was dissolved in hot EtOH, and hexane was added until a precipitate formed. The precipitate was collected by filtration to 38 (9.44 g, 77%): $^1$H NMR (300 MHz, $CD_3OD$): δ 7.42 (s, 1H), 6.83 (s, 1H), 3.84 (s, 3H).

Step 4: Condensation of 38 (3.36 g, 13.8 mmol) with 1,4-cyclohexanedione monoethylene ketal (2.37 g, 15.2 mmol), following the procedure described in Step 2, Scheme 2, gave 39 (3.12 g, 70%), as a brown foam: $^1$H NMR (500 MHz, $CDCl_3$): δ 9.80 (br s, 1H), 7.22 (s, 1H), 6.74 (s, 1H), 4.02–3.93 (m, 4H), 3.92 (s, 3H), 3.49 (s, 1H), 2.22–2.13 (m, 2H), 2.09–2.05 (m, 4H), 1.70–1.65 (m, 2H).

Step 5: The reaction of 39 (3.12 g, 9.71 mmol) in TFA (12 mL) and $H_2O$ (3 mL), following the procedure described in Step 3, Scheme 2, gave 40 (2.50 g, 99%) as a pale yellow solid: $^1$H NMR (500 MHz, $CD_3OD$): δ 7.04 (s, 1H), 6.75 (s, 1H), 5.78 (t, J=3 Hz, 1H), 3.83 (s, 3H), 3.06–3.02 (m, 2H), 2.80–2.75 (m, 2H), 2.58 (t, J=7 Hz, 2H).

Step 6: A mixture of 40 (2.50 g, 9.64 mmol) in THF (150 mL) and 20% $Pd(OH)_2/C$ (700 mg) was shaken under a $H_2$ atmosphere at 50 psi for 12 hours. The solution was filtered through Celite and concentrated under reduced pressure to give 41 (1.56 g, 62%), as a mustard-colored solid: $^1$H NMR (500 MHz, $CD_3OD$):: δ 7.10 (s, 1H), 6.77 (s, 1H), 3.86 (s, 3H), 3.52 (tt, J=9, 3 Hz, 1H), 2.60 (ddd, J=14, 14, 6 Hz, 2H), 2.40 (dt, J=15, 2 Hz, 2H), 2.15–2.08 (m, 2H), 1.91–1.85 (m, 2H).

Step 7: Condensation of 41 (2.49 g, 9.53 mmol) with methylamine (7.2 mL, 14.3 mmol) and $NaBH_4$ (541 mg, 14.3 mmol) in 2-propanol (40 mL), following the procedure described in Example 63, Step 1, gave 5-methoxy-6-(4-methylaminocyclohexyl)-3H-benzoxazol-2-one 42 (200 mg, 12%), as a white solid: $^1$H NMR (500 MHz, DMSO-$d_6$): δ 7.05 (s, 1H), 6.67 (s, 1H), 3.78 (s, 3H), 2.83 (tt, J=9, 3 Hz, 1H), 2.36–2.31 (m, 1H), 2.30 (s, 3H), 1.98 (br d, J=12 Hz, 2H), 1.70 (br d, J=12 Hz, 2H), 1.47–1.35 (m, 2H), 1.15–1.05 (m, 2H).

EXAMPLE 65

6-(trans-4-{[3-(4-Fluorophenyl)propyl]methylamino}cyclohexyl)-5-methoxy-3H-benzoxazol-2-one

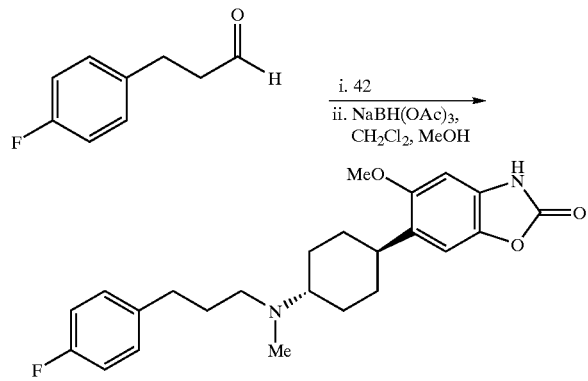

Condensation of 5-methoxy-6-(4-methylaminocyclohexyl)-3H-benzoxazol-2-one 42 (0.20 g, 0.72 mmol) with 3-(4-fluorophenyl)-propionaldehyde 25 (0.12 g, 0.79 mmol) and NaBH(OAc)$_3$ (214 mg, 1.01 mmol) in CH$_2$Cl$_2$ (4 mL) and MeOH (4 mL), following the procedure described in Example 63, Step 2, gave 6-(trans-4-{[3-(4-fluorophenyl)propyl]methylamino}-cyclohexyl)-5-methoxy-3H-benzoxazol-2-one (236 mg, 79%), as an off-white solid: mp 239–242° C.; IR (KBr): 3435, 2945, 1767, 1510, 1495 cm$^{-1}$; $^1$H NMR (500 MHz, DMSO-d$_6$): δ 11.50 (s, 1H), 10.35 (br s, 1H), 7.29 (dd, J=9, 6 Hz, 2H), 7.13 (t, J=9 Hz, 2H), 7.08 (s, 1H), 6.72 (s, 1H), 3.35–3.30 (m, 1H), 3.28 (s, 3H), 3.19–3.12 (m, 1H), 3.02–2.95 (m, 1H), 2.90 (tt, J=12, 9 Hz, 3H), 2.68 (d, J=5 Hz, 3H), 2.68–2.62 (m, 2H), 2.15–1.95 (m, 4H), 1.85–1.77 (m, 2H), 1.69–1.45 (m, 4H); ESI (m/z): 413 [M+H]$^+$; HPLC: method A, 6.31 minutes (>99%), method B, 11.6 minutes (>99%),; Anal. Calcd for C$_{24}$H$_{29}$FN$_2$O$_3$·HCl·H$_2$O: C, 61.73; H, 6.91; N, 6.00. Found: C, 61.85; H, 6.96; N, 5.87.

Scheme 8
General Procedure for the Preparation of Aryl Amines and Aldehydes

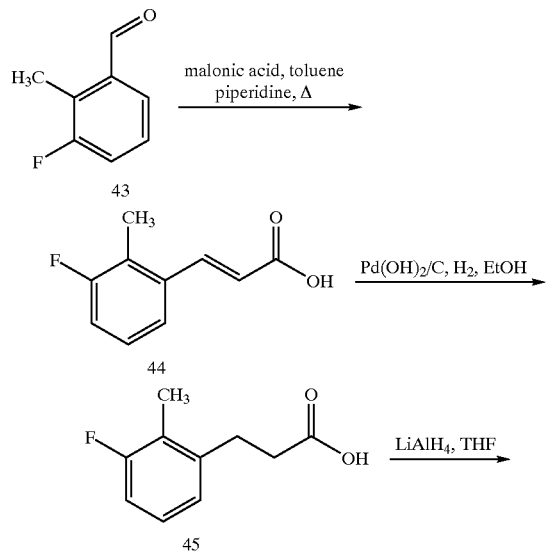

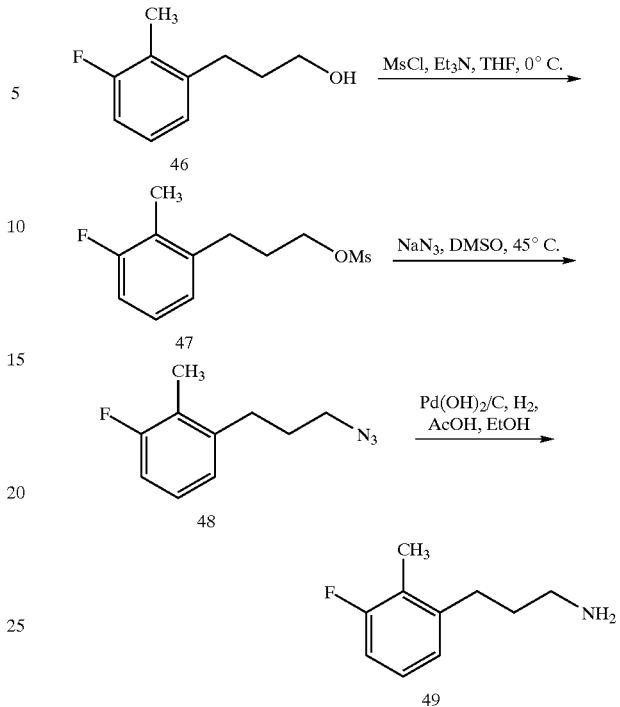

Step 1: A mixture of 3-fluoro-2-methylbenzaldehyde (10 g, 72 mmol), malonic acid (8.3 g, 80 mmol), piperidine (0.35 mL, 3.6 mmol), and toluene (150 mL) was heated to reflux (flask equipped with a Dean-stark trap) for 22 hours. After cooling to ambient temperature, the reaction mixture was extracted with saturated NaHCO$_3$ (2×30 mL), brought to pH 3 with 1N HCl, and extracted with EtOAc (3×50 mL). The combined organic extracts were dried (Na$_2$SO$_4$), filtered, and concentrated under reduced pressure to give cinnamic acid 44 (5.2 g, 40%) which was used without further purification: $^1$H NMR (500 MHz, DMSO-d$_6$): δ 12.48 (s, 1H), 7.79 (d, J=16 Hz, 1H), 7.53 (d, J=8 Hz, 1H), 7.26 (dd, J=8, 8 Hz, 1H), 7.19 (dd, J=8, 8 Hz, 1H), 6.45 (d, J=16 Hz, 1H), 2.26 (s, 3H).

Step 2: A mixture of cinnamic acid 44 (5.2 g, 29 mmol) and 29% Pd(OH)$_2$/C (100 mg) in EtOH (150 mL) was shaken under a H$_2$ atmosphere (balloon) for 22 hours. The solution was filtered through Celite and concentrated under reduced pressure to give acid 45 (5.2 g, 100%), which was used without further purification: $^1$H NMR (500 MHz, DMSO-d$_6$): δ 12.15 (s, 1H), 7.14 (dd, J=8, 8 Hz, 1H), 7.00 (d, J=8 Hz, 1H), 6.97 (dd, J=8, 8 Hz, 1H), 2.84 (dd, J=8, 7 Hz, 2H), 2.48 (dd, J=8, 7 Hz, 2H), 2.17 (d, J=2 Hz, 3H).

Step 3: To an ice-cold, stirred solution of acid 45 (5.1 g, 28 mmol) in THF (50 mL) was added LiAlH$_4$ (1.1 g, 28 mmol) portionwise over 10 minutes. After stirring for 1 hour, the reaction mixture was carefully quenched with methanol, diluted with EtOAc, filtered through Celite, and the filtrate was concentrated under reduced pressure. The residue was taken up in EtOAc, washed with 1N HCl, H$_2$O, saturated NaCl, dried (Na$_2$SO$_4$), filtered, and concentrated under reduced pressure. Purification by flash chromatography (silica, 95:5 methylene chloride/methanol) gave alcohol 46 (4.8 g, 100%): $^1$H NMR (500 MHz, DMSO-d$_6$): δ 7.14 (dd, J=8, 8 Hz, 1H), 7.00–6.92 (m, 2H), 4.44 (dd, J=7, 7 Hz, 1H), 3.54–3.41 (m, 2H), 2.66 (dd, J=8, 8 Hz, 2H), 2.16 (s, 3H), 1.67–1.62 (m, 2H).

Step 4: To an ice-cold, stirred solution of alcohol 46 (4.8 g, 29 mmol) in THF (150 mL) was added Et$_3$N (5.8 mL, 42 mmol) and then methanesulfonyl chloride (2.7 mL, 34 mmol). The reaction mixture was stirred for 10 minutes and then diluted with EtOAc (300 mL). The organic layer was washed with 1N HCl (100 mL), H₂O (100 mL), saturated NaHCO₃ (100 mL), saturated NaCl (100 mL), dried (Na₂SO₄), and filtered. Concentration under reduced pressure gave the desired mesylate 47 (7.5 g, 100%) which was used without further purification: ¹H NMR (500 MHz, DMSO-d₆): δ 7.14 (dd, J=8, 8 Hz, 1H), 7.02–6.95 (m, 2H), 4.23 (dd, J=7, 6 Hz, 2H), 3.17 (s, 1H), 2.70 (dd, J=8, 7 Hz, 2H), 2.17 (s, 3H), 1.94–1.88 (m, 2H).

Step 5: A mixture of mesylate 47 (7.1 g, 29 mmol), NaN₃ (2.8 g, 43 mmol), and tetrabutylammonium hydrogen sulfate (0.98 g, 2.9 mmol) in DMSO (50 mL) was heated to 45° C. for 16 hours. After cooling, the reaction mixture was diluted with EtOAc (300 mL) and washed with H₂O (3×100 mL), saturated NaCl (100 mL), dried (Na₂SO₄), filtered, and concentrated under reduced pressure. Purification by flash chromatography (silica, 90:10 hexanes:EtOAc) gave azide 48 (3.9 g, 70%): ¹H NMR (500 MHz, DMSO-d₆): δ 7.15 (dd, J=8, 8 Hz, 1H), 7.00–6.96 (m, 2H), 3.37 (dd, J=8, 7 Hz, 2H), 2.66 (dd, J=8, 7 Hz, 2H), 2.17 (s, 3H), 1.79–1.73 (m, 2H).

Step 6: A mixture of azide 48 (3.9 g, 20 mmol), acetic acid (1.1 mL, 20 mmol), and 20% Pd(OH)₂/C (150 mg) in EtOH (60 mL) was shaken under a H₂ atmosphere (balloon) for 30 hours. The solution was filtered through Celite and concentrated under reduced pressure. The residue was triturated with Et₂O, and the resulting solid was collected by filtration to afford 3-(2-methyl-3-fluorophenyl)-1-propylamine 49 (2.3 g, 51%), as the AcOH salt: ¹H NMR (500 MHz, DMSO-d₆): δ 7.14 (dd, J=8, 8 Hz, 1H), 7.00–6.94 (m, 2H), 6.20 (br s, 3H), 2.67–2.62 (m, 4H), 2.16 (d, J=2 Hz, 3H), 1.78 (s, 3H), 1.69–1.63 (m, 2H).

Scheme 9
Preparation of 3-(2,4-Dimethylphenyl)-1-propylamine 56

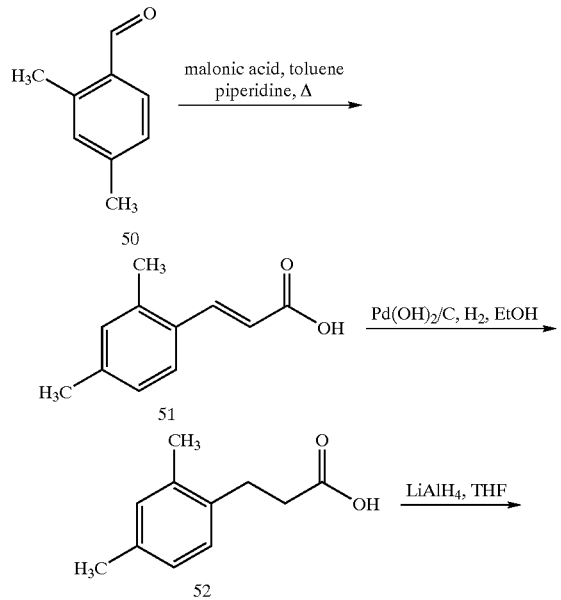

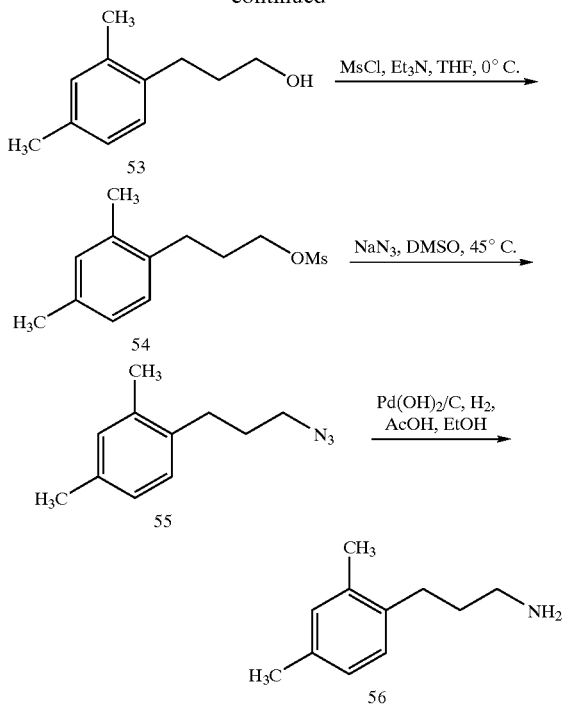

Step 1: Reaction of 2,4-dimethylbenzaldehyde (10 g, 75 mmol), malonic acid (8.5 g, 82 mmol), piperidine (0.37 mL, 3.7 mmol), and toluene (150 mL), following the procedure described in the General Procedure, Scheme 8, Step 1, gave cinnamic acid 51 (6.5 g, 49%): ¹H NMR (500 MHz, CD₃OD): δ 7.96 (d, J=16 Hz, 1H), 7.50 (d, J=8 Hz, 1H), 7.04–7.01 (m, 2H), 6.33 (d, J=16 Hz, 1H), 2.37 (s, 3H), 2.29 (s, 3H).

Step 2: Hydrogenation of cinnamic acid 51 (6.5 g, 37 mmol), following the procedure described in the General Procedure, Scheme 8, Step 2, gave acid 52 (6.6 g, 100%): ¹H NMR (500 MHz, CD₃OD): δ 7.03–6.88 (m, 3H), 2.86 (dd, J=8, 8 Hz, 2H), 2.51 (dd, J=8, 8 Hz, 2H), 2.26 (s, 3H), 2.23 (s, 3H).

Step 3: Reduction of acid 52 (6.6 g, 38 mmol) with LiAlH₄ (1.4 g, 38 mmol), following the procedure described in the General Procedure, Scheme 8, Step 3, gave alcohol 53 (6.3 g, 100%): ¹H NMR (500 MHz, CD₃OD): δ 7.00–6.86 (m, 3H), 3.57 (dd, J=7, 7 Hz, 2H), 2.61 (dd, J=8, 8 Hz, 2H), 2.25 (s, 3H), 2.23 (s, 3H), 1.79–1.69 (m, 2H).

Step 4: Reaction of alcohol 53 (6.3 g, 38 mmol) with methanesulfonyl chloride (3.5 mL, 46 mmol), following the procedure described in the General Procedure, Scheme 8, Step 4, gave mesylate 54 (8.6 g, 93%): ¹H NMR (500 MHz, DMSO-d₆): δ 7.01–6.90 (m, 3H), 4.23 (dd, J=8, 8 Hz, 2H), 3.04 (s, 3H), 2.69 (dd, J=8, 8 Hz, 2H), 2.26 (s, 3H), 2.24 (s, 3H), 2.00–1.95 (m, 2H).

Step 5: Reaction of mesylate 54 (8.6 g, 35 mmol) with NaN₃ (2.8 g, 43 mmol) in DMSO (40 mL), following the procedure described in the General Procedure, Scheme 8, Step 5, gave azide 55 (6.3 g, 95%): ¹H NMR (500 MHz, CD₃OD): δ 6.98–6.89 (m, 3H), 3.31–3.28 (m, 2H), 2.64 (dd, J=8, 8 Hz, 2H), 2.25 (s, 3H), 2.24 (s, 3H), 1.81–1.78 (m, 2H).

Step 6: Hydrogenation of azide 55 (3.4 g, 18 mmol), following the procedure described in the General Procedure, Scheme 8, Step 6, gave 3-(2,4-dimethylphenyl)-1-propylamine 56 (1.9 g, 47%), as the AcOH salt: ¹H NMR (500 MHz, CD$_3$OD): δ 7.01 (d, J=8 Hz, 1H), 6.96 (s, 1H), 6.82 (d, J=8 Hz, 1H), 2.95–2.91 (m, 2H), 2.66 (dd, J=8, 8 Hz, 2H), 2.27 (s, 3H), 2.24 (s, 3H), 1.88 (s, 3H), 1.89–1.87 (m, 2H).

Scheme 10
Preparation of 3-(3,4-Difluorophenyl)-1-propylamine 62

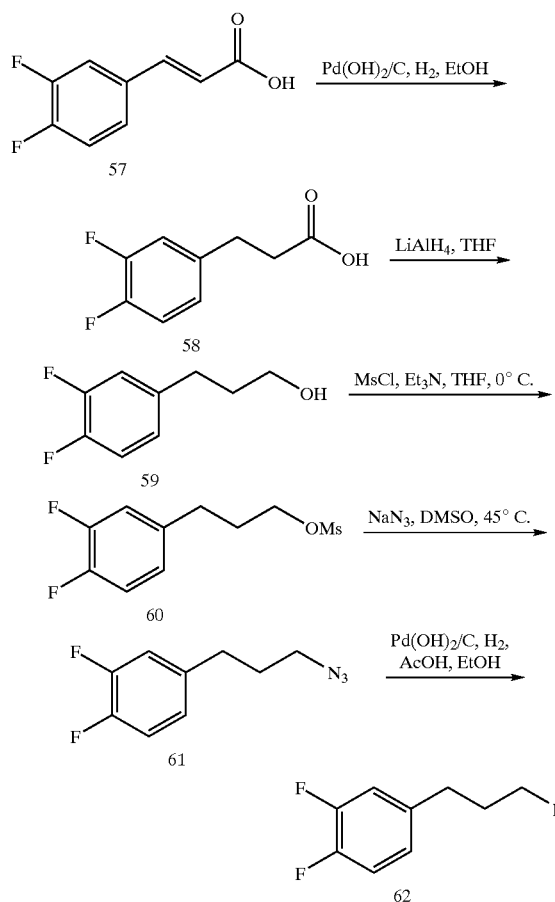

Step 1: Hydrogenation of cinnamic acid 57 (5.0 g, 27 mmol), following the procedure described in the General Procedure, Scheme 8, Step 2, gave acid 58 (5.0 g, 100%): $^1$H NMR (500 MHz, CD$_3$OD): δ 7.15–7.09 (m, 2H), 7.01–6.99 (m, 1H), 2.88 (dd, J=8, 8 Hz, 2H), 2.58 (dd, J=8, 8 Hz, 2H).

Step 2: Reduction of acid 58 (5.0 g, 27 mmol) with LiAlH$_4$ (1.1 g, 29 mmol), following the procedure described in the General Procedure, Scheme 8, Step 3, gave alcohol 59 (3.2 g, 70%): $^1$H NMR (500 MHz, DMSO-d$_6$): δ 7.35–7.22 (m, 2H), 7.05–7.01 (m, 1H), 4.50 (br s, 1H), 3.39 (dd, J=7, 7 Hz, 2H), 2.60 (dd, J=8, 8 Hz, 2H), 1.74–1.64 (m, 2H).

Step 3: Reaction of alcohol 59 (8.1 g, 47 mmol) with methanesulfonyl chloride (4.4 mL, 56 mmol), following the procedure described in the General Procedure, Scheme 8, Step 4, gave mesylate 60 (11.5 g, 98%): $^1$H NMR (500 MHz, CD$_3$OD): δ 7.16–7.10 (m, 2H), 7.02–6.99 (m, 1H), 4.22 (dd, J=8, 8 Hz, 2H), 3.04 (s, 3H), 2.72 (dd, J=8, 8 Hz, 2H), 2.05–1.99 (m, 2H).

Step 4: Reaction of mesylate 60 (12 g, 50 mmol) with NaN$_3$ (3.6 g, 55 mmol) in DMSO (60 mL), following the procedure described in the General Procedure, Scheme 8, Step 5, gave azide 61 (8.8 g, 89%): $^1$H NMR (500 MHz, CD$_3$OD): δ 7.16–7.09 (m, 2H), 7.02–6.99 (m, 1H), 3.29 (dd, J=8, 8 Hz, 2H), 2.67 (dd, J=8, 8 Hz, 2H), 1.90–1.81 (m, 2H).

Step 5: Hydrogenation of azide 61 (8.8 g, 45 mmol), following the procedure described in the General Procedure, Scheme 8, Step 6, gave 3-(3,4-difluorophenyl)-1-propylamine 62 (1.9 g, 47%), which was converted to the HCl salt: $^1$H NMR (500 MHz, DMSO-d$_6$): δ 8.09 (br s, 3H), 7.37–7.29 (m, 2H), 7.09–7.06 (m, 1H), 2.75–2.72 (m, 2H), 2.66 (dd, J=8, 8 Hz, 2H), 1.89–1.83 (m, 2H).

Scheme 11
Preparation of 3-(2-Chloro-4-fluorophenyl)-1-propylamine 69

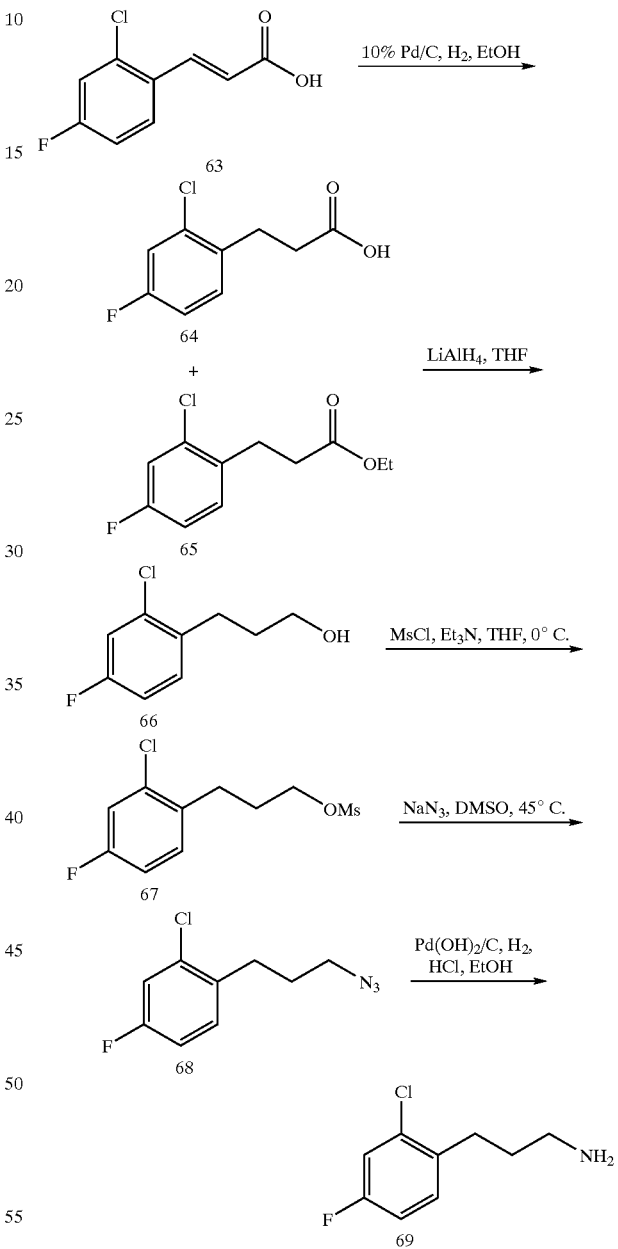

Step 1: Hydrogenation of cinnamic acid 63 (10 g, 52 mmol), following the procedure described in the General Procedure, Scheme 8, Step 2, except 10% Pd/C was used as catalyst, gave a mixture of acid 64 and ethyl ester 65 (11 g). Reduction of the mixture with LiAlH$_4$ (1.8 g, 48 mmol), following the procedure described in the General Procedure, Scheme 8, Step 3, gave alcohol 66 (9.7 g, 100%): $^1$H NMR (500 MHz, CD$_3$OD): δ 7.30 (dd, J=9, 7 Hz, 1H), 7.20–7.14 (m, 1H), 7.00–6.96 (m, 1H), 3.58 (dd, J=7, 7 Hz, 2H), 2.78 (dd, J=7, 7 Hz, 2H), 1.84–1.78 (m, 2H).

Step 2: Reaction of alcohol 66 (9.1 g, 48 mmol) with methanesulfonyl chloride (4.5 mL, 58 mmol), following the procedure described in the General Procedure, Scheme 8, Step 4, gave mesylate 67 (13 g, 100%): $^1$H NMR (500 MHz, CD$_3$OD): δ 7.34 (dd, J=7, 7 Hz, 1H), 7.19 (dd, J=9, 3 Hz, 1H), 7.02 (ddd, J=9, 7, 3 Hz, 1H), 4.26 (dd, J=7, 7 Hz, 2H), 3.06 (s, 3H), 2.86 (dd, J=8, 8 Hz, 2H), 2.06–2.01 (m, 2H).

Step 3: Reaction of mesylate 67 (13 g, 49 mmol) with NaN$_3$ (3.4 g, 53 mmol) in DMSO (50 mL), following the procedure described in the General Procedure, Scheme 8, Step 5, gave azide 68 (9.9 g, 96%): $^1$H NMR (500 MHz, CD$_3$OD): δ 7.32–7.28 (m, 1H), 7.21–7.16 (m, 1H), 7.02–6.97 (m, 1H), 3.33 (dd, J=8, 8 Hz, 2H), 2.82–2.79 (m, 2H), 1.90–1.83 (m, 2H).

Step 4: Hydrogenation of azide 68 (10 g, 48 mmol), following the procedure described in the General Procedure, Scheme 8, Step 6, except HCl was used in place of AcOH, gave 3-(2-chloro-4-fluorophenyl)-1-propylamine 69 (7.8 g, 72%), as the HCl salt: $^1$H NMR (500 MHz, DMSO-d$_6$): δ 8.20 (br s, 3H), 7.45 (dd, J=7, 7 Hz, 1H), 7.40 (dd, J=9, 3 Hz, 1H), 7.19 (ddd, J=9, 7, 3 Hz, 1H), 2.84–2.74 (m, 4H), 1.91–1.84 (m, 2H).

Scheme 12
Preparation of 3-(4-Chloro-2-fluorophenyl)-1-propylamine 76

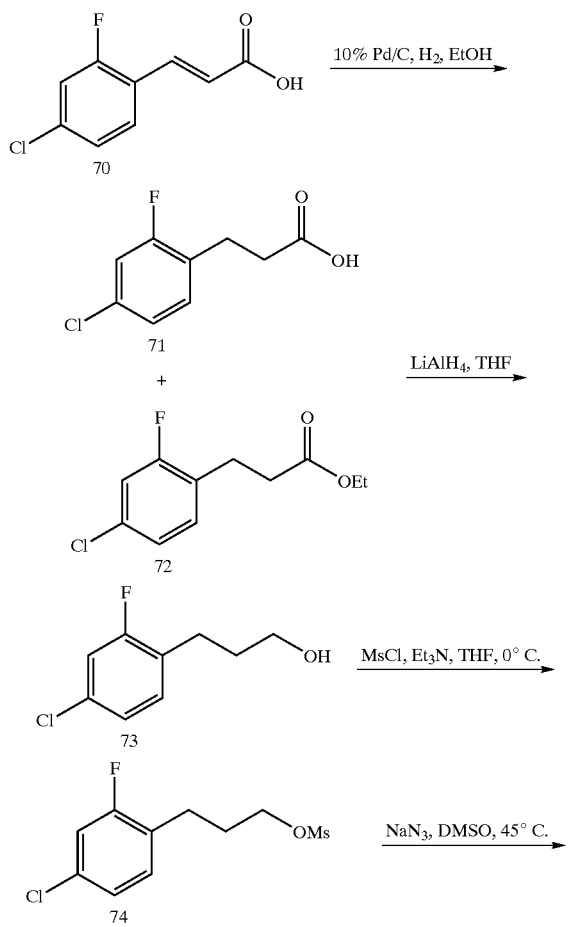

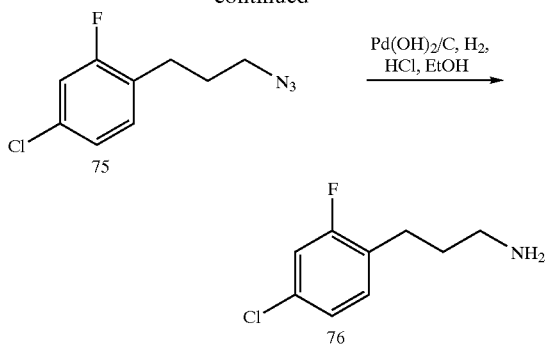

Step 1: Hydrogenation of cinnamic acid 70 (12 g, 60 mmol), following the procedure described in the General Procedure, Scheme 8, Step 2, except Pd/C was used, gave a mixture of acid 71 and ethyl ester 72 (12 g). Reduction of the mixture with LiAlH$_4$ (1.9 g, 50 mmol), following the procedure described in the General Procedure, Scheme 8, Step 3, gave alcohol 73 (9.4 g, 100%): $^1$H NMR (500 MHz, CD$_3$OD): δ 7.26–7.22 (m, 1H), 7.12–7.09 (m, 2H), 3.57 (dd, J=7, 7 Hz, 2H), 2.70 (dd, J=7, 7 Hz, 2H), 1.84–1.77 (m, 2H).

Step 2: Reaction of alcohol 73 (9.4 g, 50 mmol) with methanesulfonyl chloride (4.6 mL, 60 mmol), following the procedure described in the General Procedure, Scheme 8, Step 4, gave mesylate 74 (13 g, 100%): $^1$H NMR (500 MHz, CD$_3$OD): δ 7.28 (dd, J=7, 7 Hz, 1H), 7.15–7.13 (m, 2H), 4.24 (dd, J=7, 7 Hz, 2H), 3.06 (s, 3H), 2.77 (dd, J=8, 8 Hz, 2H), 2.06–2.00 (m, 2H).

Step 3: Reaction of mesylate 74 (13 g, 50 mmol) with NaN$_3$ (3.6 g, 55 mmol) in DMSO (50 mL), following the procedure described in the General Procedure, Scheme 8, Step 5, gave azide 75 (11 g, 96%): $^1$H NMR (500 MHz, CD$_3$OD): δ 7.26–7.22 (m, 1H), 7.14–7.09 (m, 2H), 3.31 (dd, J=7, 7 Hz, 2H), 2.70 (dd, J=7, 7 Hz, 2H), 1.90–1.83 (m, 2H).

Step 4: Hydrogenation of azide 75 (11 g, 50 mmol), following the procedure described in the General Procedure, Scheme 8, Step 6, except HCl was used in place of AcOH, gave 3-(4-chloro-2-fluorophenyl)-1-propylamine 76 (7.4 g, 66%), as the HCl salt: $^1$H NMR (500 MHz, DMSO-d$_6$): δ 8.18 (br s, 3H), 7.41–7.36 (m, 2H), 7.26–7.31 (m, 1H), 2.84–2.77 (m, 2H), 2.69 (dd, J=8, 8 Hz, 2H), 1.90–1.83 (m, 2H).

Scheme 13
Preparation of 3-(4-Fluoro-2-methylphenyl)-1-propylamine 79

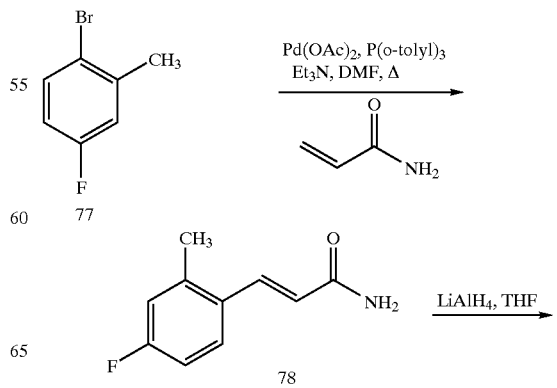

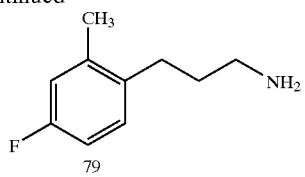

Step 1: A mixture of 2-bromo-5-fluorotoluene (2.0 g, 11 mmol), acrylamide (1.5 g, 21 mmol), P(o-tolyl)$_3$ (320 mg, 1.1 mmol), and Et$_3$N (2.9 mL, 21 mmol), in toluene (25 mL) was deoxygenated by bubbling a stream of Ar through the solution for 15 minutes. Palladium(II) acetate (120 mg, 0.53 mmol) was added to the reaction mixture, and a stream of Ar was again passed through the mixture for 15 minutes. The reaction was heated to 140° C. for 2.25 hours, then cooled to ambient temperature, diluted with EtOAc, and filtered through Celite. The filtrate was washed with H$_2$O, 1N HCl, H$_2$O, dried (Na$_2$SO$_4$), filtered, and concentrated under reduced pressure to give amide 78 (1.7 g, 86%) which was used without further purification: $^1$H NMR (500 MHz, DMSO-d$_6$): δ 7.60–7.52 (m, 3H), 7.15–7.04 (m, 3H), 6.46 (d, J=16 Hz, 1H), 2.37 (s, 3H).

Step 2: To amide 78 (2.3 g, 13 mmol) in THF (25 mL) was added LiAlH$_4$ 970 mg, 25 mmol) portionwise over 5 minutes. The reaction mixture was heated to reflux for 1 hour, cooled in an ice/H$_2$O bath, carefully quenched with methanol, filtered through Celite, and the filtrate was concentrated under reduced pressure. The residue was purified by flash chromatography (silica, 90:9.5:0.5 methylene chloride:methanol:NH$_4$OH) gave 3-(4-fluoro-2-methylphenyl)-1-propylamine 79 (580 mg, 22%), as the HCl salt: $^1$H NMR (500 MHz, DMSO-d$_6$): δ 8.05 (br s, 3H), 7.20–7.14 (m, 1H), 7.03–6.91 (m, 2H), 2.80 (dd, J=8, 6 Hz, 2H), 2.63 (dd, J=8, 8 Hz, 2H), 2.29 (s, 3H), 1.88–1.76 (m, 2H).

Scheme 14
Preparation of 3-(4-Dimethylaminophenyl) propionaldehyde 82

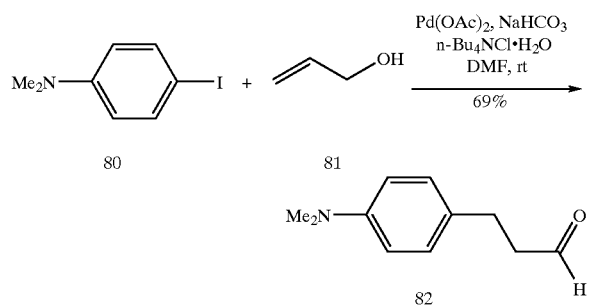

Alcohol 81 (2.80 mL, 56.5 mmol), (1-iodophenyl) dimethylamine 80 (5.04 g, 20.4 mmol), sodium bicarbonate (4.30 g, 51.2 mmol), and tetrabutylammonium chloride hydrate (5.68 g, 20.4 mmol) were combined in DMF (25 mL). The reaction mixture was deoxygenated by passing a stream of argon through the solution for 15 minutes. Palladium(II) acetate (59 mg, 0.24 mmol) was added, and a stream of argon was again bubbled through the mixture for 10 minutes. After stirring under an argon atmosphere for 62 hours, the reaction mixture was partitioned between EtOAc (300 mL) and water (200 mL). The organic layer was separated, washed with water (3×200 mL) and saturated NaCl (200 mL), dried (Na$_2$SO$_4$), filtered, and concentrated under reduced pressure. Purification by chromatography (silicia, 9:1 to 3:2 hexanes:EtOAc) gave 3-(4-dimethylaminophenyl)propionaldehyde 82 (910 mg, 25%): $^1$H NMR (300 MHz, CDCl$_3$): δ 9.82 (s, 1H), 7.08 (d, J=8 Hz, 2H), 6.70 (d, J 8 Hz, 2H), 2.91 (s, 6H), 2.90–2.85 (m, 2H), 2.73 (dd, J=8, 7 Hz, 2H).

Scheme 15
Preparation of 3-(2, 3, 4-Trifluorophenyl) propionaldehyde 86

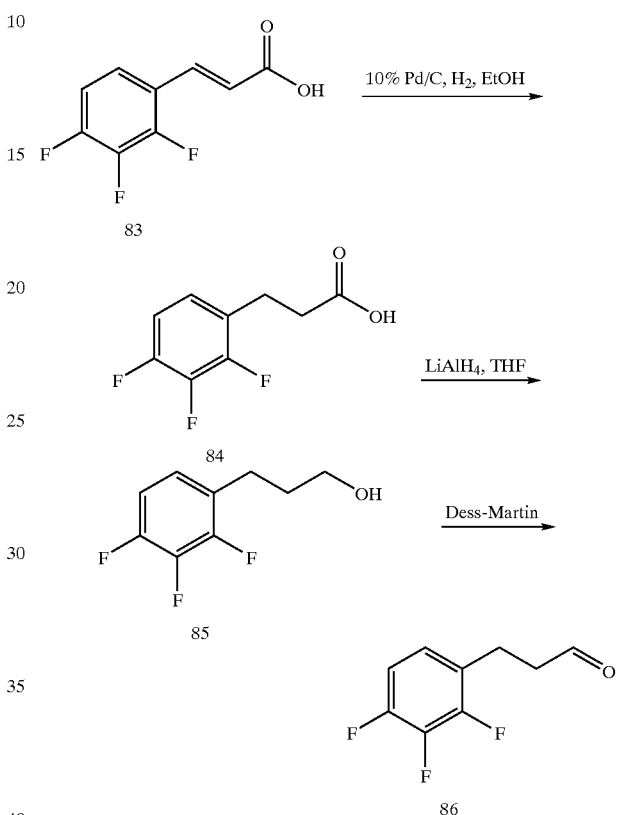

Step 1: Hydrogenation of cinnamic acid 83 (5.0 g, 25 mmol), following the procedure described in the General Procedure, Scheme 8, Step 2, except 10% Pd/C was used, gave acid 84 (5.0 g, 99%): $^1$H NMR (300 MHz, DMSO-d$_6$): δ 7.25–7.14 (m, 2H), 2.85 (dd, J=8, 7 Hz, 2), 2.54 (dd, J=8, 7 Hz, 2H).

Step 2: Reduction of acid 84 (5.0 g, 24 mmol) with LiAlH$_4$ (930 mg, 24 mmol), following the procedure described in the General Procedure, Scheme 8, Step 3, gave alcohol 85 (4.6 g, 100%): $^1$H NMR (300 MHz, DMSO-d$_6$): δ 7.23–7.11 (m, 2H), 4.45 (t, J=5 Hz, 1H), 3.42 (dd, J=6, 6 Hz, 2H), 2.66 (dd, J=8, 8 Hz, 2H), 1.70–1.63 (m, 2H).

Step 3: A mixture of alcohol 85 (1.0 g, 5.3 mmol), Dess-Martin periodane (4.5 g, 11.0 mmol), and water (0.1 mL) in CH$_2$Cl$_2$ (50 mL) was stirred for 4 hours. The reaction mixture was diluted with CH$_2$Cl$_2$ (40 mL), filtered through Celite, and the resulting filtrate concentrated under reduced pressure. Purification by chromatography (silica, 9:1 hexanes:EtOAc) gave 3-(2,3,4-trifluorophenyl)-propionaldehyde 86 (280 mg, 28%) as an oil: $^1$H NMR (300 MHz, DMSO-d$_6$): δ 9.71 (s, 1H), 7.34–7.17 (m, 2H), 2.89–2.81 (m, 4H).

Scheme 16
Preparation of 3-(2, 4, 6-Trifluorophenyl) propionaldehyde 91

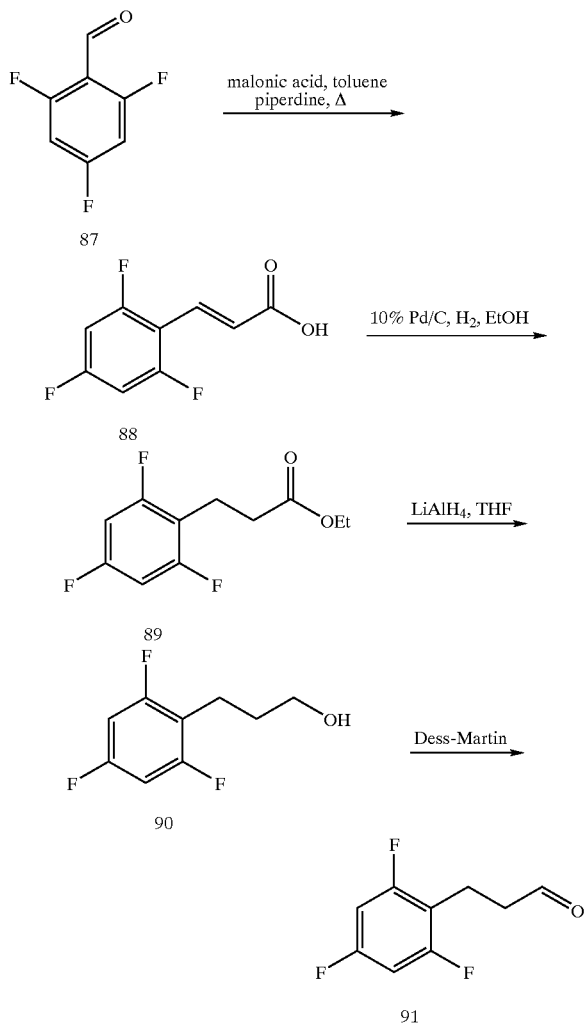

Step 1: Reaction of 2,4,6-trifluorobenzaldehyde (4.7 g, 29 mmol), malonic acid (3.4 g, 32 mmol), piperidine (0.14 mL, 1.4 mmol), and toluene (75 mL), following the procedure described in the General Procedure, Scheme 8, Step 1, gave cinnamic acid 88 (2.2 g, 37%): $^1$H NMR (300 MHz, CDCl$_3$): δ 7.80 (dd, J=16 Hz, 1H), 6.79–6.65 (m, 3H), 6.97 (dd, J=8, 8 Hz, 1H).

Step 2: Hydrogenation of cinnamic acid 88 (2.2 g, 11 mmol), following the procedure described in the General Procedure, Scheme 8, Step 2, except 10% Pd/C was used, gave ethyl ester 89 (2.2 g, 88%): $^1$H NMR (300. MHz, CDCl$_3$): δ 6.72–6.62 (m, 2H), 3.73 (q, J=14, 7 Hz, 2H), 3.02–2.94 (m, 2H), 2.64 (dd, J=7, 7 Hz, 2H), 1.25 (t, J=7 Hz, 3H).

Step 3: Reduction of ester 89 (2.2 g, 11 mmol) with LiAlH$_4$ (410 mg, 11 mmol), following the procedure described in the General Procedure, Scheme 8, Step 3, gave alcohol 90 (470 mg, 26%): $^1$H NMR (500 MHz, DMSO-d$_6$): δ 7.19–7.07 (m, 2H), 4.47 (t, J=5 Hz, 1H), 6.83 (dd, J=8, 6 Hz, 2H), 2.61 (dd, J=8, 8 Hz, 2H), 1.66–1.61 (m, 2H).

Step 4: A mixture of alcohol 90 (470 mg, 2.50 mmol), Dess-Martin periodane (2.1 g, 4.90 mmol), and water (0.04 mL) in CH$_2$Cl$_2$ (25 mL) was stirred for 3 hours. The reaction mixture was filtered through Celite and the resulting filtrate concentrated under reduced pressure. Purification by chromatography (silica, 5:1 hexanes:EtOAc) gave 3-(2,4,6-trifluorophenyl)-propionaldehyde 91 (360 mg, 76%) as an oil: $^1$H NMR (300 MHz, DMSO-d$_6$): δ 9.67 (s, 1H), 7.22–7.13 (m, 2H), 2.82–2.80 (m, 2H), 2.75–2.72 (m, 2H).

Electrophysiological Assays at NMDA Receptor Subunits

Preparation of RNA. cDNA clones encoding the NR1A, NR2A, NR2B, and NR2C rat NMDA receptor subtypes were used (see, Moriyoshi, supra., 1991; Kutsuwada et al., supra., 1992; Monyer et al., supra, 1992; Ikeda et al., *FEBS Lett.*, 1992;313:34–38; Ishii et al., *J. Biol. Chem.*, 1993;268:2836–2843 for details of these clones or their mouse homologs). The clones were transformed into appropriate host bacteria and plasmid preparations were made with conventional DNA purification techniques. A sample of each clone linearized by restriction enzyme digestion of cRNA was synthesized with T3 RNA polymerase. The cRNA was diluted to 400 ng/µL and stored in 1-µL aliquots at –80° C. until injection.

The Xenopus oocyte expression system. Mature female *Xenopus laevis* were anaesthetized (20–40 minutes) using 0.15% 3-aminobenzoic acid ethyl ester (MS-222), and 2 to 4 ovarian lobes were surgically removed. Oocytes at developmental stages IV–VI (Dumont J. N., *J. Morphol.*, 1972;136:153–180) were dissected from the ovary still surrounded by enveloping ovarian tissues. Follicle-enclosed oocytes were microinjected with 1:1 mixtures of NR1A:NR2A, 2B or 2C; injecting 1 to 10 ng of RNA encoding each receptor subunit. NR1A encoding RNA was injected alone at ~20 ng. Oocytes were stored in Barth's medium containing (in mM): NaCl, 88; KCl, 1; CaCl$_2$, 0.41; Ca(NO$_3$)$_2$, 0.33; MgSO$_4$, 0.82; NaHCO$_3$, 2.4; HEPES 5; pH 7.4, with 0.11 mg/mL gentamicin sulphate. While oocytes were still surrounded by enveloping ovarian tissues, the Barth's medium was supplemented with 0.1% bovine serum. Oocytes were defolliculated 1 to 2 days following injections by treatment with collagenase (0.5 mg/mL Sigma Type I for 0.5–1 hr)-(Miledi and Woodward, *J. Phsyiol.*, (*Lond*) 1989;416:601–621) and subsequently stored in serum-free medium.

Electrical recordings were made using a conventional two-electrode voltage clamp (Dagan TEV-200) over periods ranging between 3 to 21 days following injection (Woodward et al., *Mol. Pharmacol.*, 1992;41:89–103). Oocytes were placed in a 0.1-mL recording chamber continuously perfused (5 mL–15 mL min$^{-1}$) with frog Ringer's solution containing (in mM): NaCl, 115; KCL, 2; BaCl$_2$, 1.8; HEPES, 5; and pH 7.4. Drugs were applied by bath perfusion. Using oocytes expressing different subunit combinations of NMDA receptor, NMDA currents were activated by co-application of glutamate (100 µM) and glycine (1–100 µM). Inhibitory potency of the novel antagonists was assessed on responses elicited by fixed concentrations of glutamate and glycine, by measuring reductions in current induced by progressively increasing concentrations of antagonist.

Concentration-inhibition curves were fit with Equation 1.

$$I/I_{control}=1/(1+([\text{antagonist}]/10^{-pIC_{50}})^n) \quad \text{Eq. 1}$$

In which $I_{control}$ is the current evoked by agonists alone, $pIC_{50}=-\log IC_{50}$, $IC_{50}$ is the concentration of antagonist that produced half maximal inhibition, and n is the slope factor (De Lean et al., *Am. J. Physiol.*, 1978;235:E97–102). For incomplete curves, analysis by fitting was unreliable and $IC_{50}$ values were calculated by simple regression over linear portions of the curves (Origin: Microcal Software).

The electrophysiological assay results are set forth in Table 1.

6-OHDA Lesioned Rat Assay

6-Hydroxydopamine-lesioned rats were used (see Ungerstedt U., Arbuthnott G. W., Quantitative recording of rotational behavior in rats after 6-hydroxy-dopamine lesions of the nigrostraiatal dopamine system. *Brain Res.*, 1971;24(3):485–93). Adult male Sprague-Dawley rats were anesthetized with chloral hydrate and unilateral lesions of the nigrostriatal dopamine system were accomplished by infusion of 8 µg of 6-hydroxydopamine HBr (6-OHDA) into the right medial forebrain bundle. Rats were pretreated 30 minutes before surgery with desipramine HCl 25 mg/kg intraperitoneally (IP) to protect noradrenegic neurons, and pargyline 25 mg/kg IP to potentiate the effects of 6-OHDA. A minimum of 3 weeks after surgery, the rotational behavior induced by apomorphine HCL 50 µg/kg subcutaneously (SC) was assessed. Only rats demonstrating more than 100 contraversive turns/hour to apomorphine were used for the present experiments.

Rotational behavior was measured using an automatic rotometer system (Rotorat Rotational Activity System, MED Associates, Georgia, Vt.). Anti-parkinsonian activity was assessed as the ability of the compound to potentiate the contraversive rotation induced by L-DOPA methyl ester, 10 mg/kg SC, over a 6-hour period. Experiments were conducted using a crossover paradigm where each rat received either a vehicle plus L-DOPA, or the test compound plus L-DOPA, in randomized order. Rats were tested at 7-day intervals. In experiments in which the compound was tested orally, rats were food deprived for 16 hours. Statistical analysis between treatment groups were performed using a paired t-test. The results were reported in Table 1 as the minimum effective dose (MED) of compound (mg/kg) required to produce a statistically-significant increase in total contraversive rotations compared to rats receiving L-DOPA only.

[$^3$H]Ifenprodil Binding Assay Protocol

MATERIALS AND METHODS

All buffers and reagents used in assay incubations or to dissolve drugs were prepared using water purified through a Milli-Q reverse osmosis system (Millipore Corp, Bedford, Mass.) and treated with UV emissions. Prior to use in the assays, buffers were further filtered through a sterile Corning filtration unit (Corning Glass Works, Corning, N.Y.) containing a 0.2-micron filter. Buffer used to rinse the membranes on the assay filters was prepared with purified water, but was not refiltered and was stored no longer than 5 days. Stock solutions of the drugs (usually 10 mM) were dissolved in 20 mM HEPES-KOH buffer pH 7.4 (assay buffer) with the addition of 1 to 5 µL of glacial AcOH, if needed to keep them in solution. For eliprodil the stock solution was buffered with the addition of 10% DMSO. All subsequent dilutions from stock were made in buffer.

Membrane Preparation

An extensively washed buffy coat membrane fraction was prepared from frozen adult rat forebrains (Zivic-Miller Laboratories, Inc., Zelienople, Pa.) as described previously (Coughenour L. L., Cordon, J. J., *J. Pharmacol. Exp. Ther.*, 1997;280:584–592) and stored at −80° C. On the day of the assay, pellets were resuspended in 35 mL of assay buffer at pH 7.4 using a Polytron setting 6. After incubation at 37° C. for 30 minutes in a shaking water bath, the homogenate was centrifuged 40,000×g for 10 minutes at 4° C. The pellets were resuspended in fresh buffer and centrifuged 3 more times before final suspension for use in the assay.

Binding Studies

[$^3$H]Ifenprodil Binding. Triplicate incubations were carried out in a volume of 0.5 mL in 1.3 mL polypropylene tubes (Marsh Biomedical Products Inc., Rochester, N.Y.) for 2 hours at room temperature. Incubations contained test agents, membranes (100–200 µg protein) and 4 nM[$^3$H]-ifenprodil in 20 mM HEPES-KOH buffer, pH 7.4 (assay buffer). Assays were started by addition of the membranes. Bound radioligand was separated by filtration under reduced pressure using a Tomtec Mach II, 96-well cell harvester (Tomtec Inc., Orange, Colo.). Filtration was through Whatman GF/B glass fiber filters (Whatman Ltd, Maidstone, England), which had been soaked for at least 15 minutes in 0.3% polyethylenimine and allowed to air dry. The filters were rinsed with 3 mL of ice cold assay buffer within 6 seconds. Air was allowed to pass through the filters for an additional 10 seconds to remove residual moisture. The filter mat was supported on a cold (−20° C.) teflon support, and filters from individual wells were separated and placed in Mini Poly-Q vials (Beckman Instruments Inc., Fullerton, Calif.) and filled with 4 mL of scintillation cocktail (Beckman Ready Protein$^+$). Radioactivity retained on the filter was determined by liquid scintillation spectrophotometry. Nonspecific binding was defined as the binding in the presence of 1 mM ifenprodil. Specific binding was 90%.

[$^3$H]-TCP binding. Binding assays were carried out essentially as described for [$^3$H]ifenprodil binding. Incubations contained test agents, 100 to 200 µg protein, 2 nM [$^3$H]-TCP, and 10 µM glutamate, glycine and spermidine. Incubations were for 10 minutes to allow assays to be carried out under nonequilibrium conditions for the detection of binding selective to NMDA receptors of the NR2B subtype. Specific binding was defined as the binding displaced by 100 µM (+)MK-801 and was 90% of the total binding.

Data analysis. Binding curves were statistically analyzed for a best one or two site competition fit using GraphPad Prism software (GraphPad Software Inc., San Diego, Calif.). The normalized data was fit by nonweighted nonlinear regression to either $$y = \text{Bottom} + \frac{(\text{Top} - \text{Bottom})}{1 + 10^{x-\text{Log}EC50}}$$

or $$y = \text{Bottom} + (\text{Top} - \text{Bottom})\frac{\text{Fraction} - 1}{1 + 10^{x-\text{Log}EC50\_1}} + \frac{1 - \text{Fraction} - 1}{1 + 10^{x-\text{Log}EC50\_2}}$$

Control data was entered as 100%, and no parameters were constrained. Inhibition curves were compared by ANOVA with post test comparisons of the logIC$_{50}$ using Dunnett's multiple comparisons post test or Student's nonpaired, two-tailed t-test (GraphPad InStat software).

Materials. TCP, [piperidyl-3,4-$^3$H(N)]-(specific activity, 45–50 Ci/mmol) and ifenprodil, [phenyl-$^3$H]-(specific activity, 66.2 Ci/mmol) were purchased from Dupont NEN Research Products (Boston, Mass.). Ifenprodil tartrate, trifluperidol hydrochloride, and GBR-12909 dihydrochloride were purchased from Research Biochemicals International (Natick, Mass.). Spermidine trihydrochloride was purchased from United States Biochemical Corp (Cleveland, Ohio). HEPES, glutamate, and glycine were purchased from Sigma Chemical Co, (St. Louis, Mo.). Haloperidol was obtained from McNeil Laboratories (Raritan, N.J.) or Research Biochemicals International. Eliprodil was synthesized by Thomas Malone (Parke-Davis Pharmaceutical Research, Ann Arbor Mich.), and (+)MK-801 was synthesized by Leonard Lescosky (Parke-Davis Pharmaceutical Research, Ann Arbor, Mich.).

TABLE 1

| Example | NR1A/NR2B Oocyte IC$_{50}$ ($\mu$M) | [$^3$H]Ifenprodil IC$_{50}$ ($\mu$M) | 6-OHDA MED (mg/kg) |
|---|---|---|---|
| 1 | 0.03 | 0.004 | 30 (active) |
| 2 | 0.10 | 0.040 | 10.0 (active) |
| 3 | 0.10 | 0034 | 10.0 (active) |
| 4a | 0.02 | 0.007 | 10.0 (inactive) |
| 5a | 0.02 | 0.004 | |
| 5b | | 0.021 | |
| 6 | | 0.009 | |
| 7 | 0.09 | 0.037 | |
| 8 | 0.02 | | |
| 9 | 0.06 | 0.015 | |
| 10 | 0.11 | 0.049 | |
| 11a | 55.00 | >1 | |
| 11b | 10 | >1 | |
| 12 | 70 | 22.5 | |
| 13a | 0.08 | 0.038 | |
| 13b | 0.02 | 0.005 | |
| 14 | | 0.128 | |
| 15 | 0.46 | 0.092 | |
| 16 | 2.50 | 1.730 | |
| 17 | | 0.010 | 10 (active) |
| 18 | 0.065 | 0.009 | 10 (active) |
| 19 | | 0.185 | |
| 20 | | 0.025 | 30 (active) |
| 21 | | 0.016 | 10 (active) |
| 22 | | 0.053 | 10 (active) |
| 23 | | 0.038 | 10 (active) |
| 24b | | 0.014 | |
| 25 | | 0.079 | 10 (active) |
| 26 | | 0.188 | |
| 27 | | 0.132 | |
| 28 | | 0.184 | |
| 29 | | 0.018 | |
| 30 | | 0.219 | |
| 31 | | 0.465 | |
| 32 | | 0.158 | |
| 33 | | >1 $\mu$M | |
| 34 | | 0.152 | |
| 35 | | 0.170 | |
| 36b | | >1 $\mu$M | |
| 37b | | 0.032 | |
| 38b | | 0.007 | |
| 39b | | 0.037 | |
| 40b | | 0.029 | |
| 41b | | 0.068 | |
| 42b | | 0.980 | |
| 43b | | 0.056 | |
| 44b | | 0.007 | |
| 45b | | 0.007 | |
| 46b | | 0.009 | |
| 47b | | 0.015 | |
| 48b | | 0.020 | |
| 49b | | 0.022 | |
| 50b | | 0.351 | |
| 51b | | 0.550 | |
| 52b | | 0.003 | |
| 53 | | 0.002 | |
| 54 | | 0.034 | |
| 55 | | 0.005 | |
| 56 | | 0.071 | |
| 57 | | 0.006 | |
| 58 | | 0.357 | |
| 59 | | 0.316 | |
| 60 | | >1 $\mu$M | |
| 61b | | 0.012 | |
| 62 | | 0.017 | |
| 63 | | 0.002 | |
| 64 | | 0.045 | |
| 65 | | 0.067 | |

While the forms of the invention exemplified herein such as, for example, the named species of Formulas I–III and the recitation of treatment of Parkinson's constitute presently preferred embodiments, many others are possible. It is not intended that said recited species of Formulas I–III and preferred methods of use should, in any manner, limit or restrict the invention from the full scope claimed herein. It is not intended herein to name all of the possible equivalent forms or ramifications of the invention. It is understood that the terms used herein are merely descriptive, rather than limiting. For example, the term "Parkinson's disease" is merely descriptive, and not limiting, of the term "neurodegenerative disease."

What is claimed is:

1. Bicycle-substituted cyclohexyl amines of Formula 1 and their pharmaceutically acceptable salts thereof

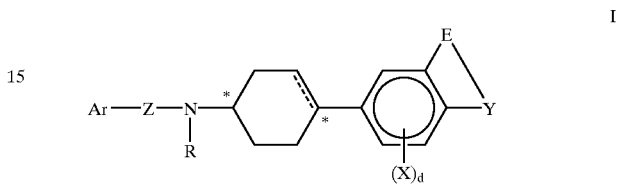

wherein:

Ar is substituted 1 to 3 times or unsubstituted aryl wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, and $N(CH_3)_2$;

Z is

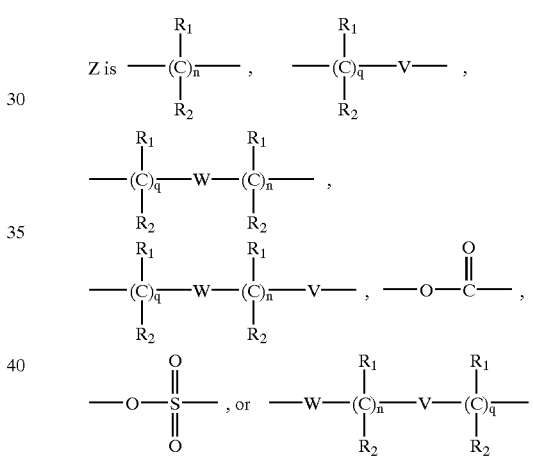

wherein V is —$(CH_2)_n$—,

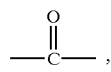

—S(O)—, or —S(O)$_2$—,

W is —$(CH_2)_n$—,

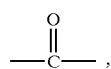

—S(O)—, —S(O)$_2$—, —O—, —S—, —C≡C—, or entgegen or zusammen —CH($R_1$)=CH($R_2$)—, d is an integer from 0 to 2;
n is an integer from 1 to 6;
q is an integer from 0 to 6;
$R_1$ and $R_2$ are independently selected from the group consisting of hydrogen, alkyl, OH, hydroxyalkyl, aminoalkyl, aralkyl, and $N(R_4)(R_5)$ where in $R_4$ and $R_5$ are independently selected from hydrogen, alkyl, aralkyl, heteroaryl, heteroaralkyl, aminoalkyl, hydroxyalkyl, and thioalkyl;

R is hydrogen, alkyl, C(O)R$_6$, C(O)OR$_6$, C(O)NHR$_6$, -alkyl-C(O)NH$_2$, aralkyl, (C$_3$–C$_7$ cycloalkyl)-alkyl, hydroxyalkyl, aminoalkyl, amino(hydroxy)alkyl, carboxyalkyl, heteroaralkyl, alkenylalkyl, or OH wherein R$_6$ is alkyl or aralkyl;

X is independently selected from hydrogen and an electron withdrawing group selected from halogen, nitro, cyano, alkyl, CF$_3$, C(O)CH$_3$, P(O)(O—R$_9$)$_2$, SO$_2$—R$_9$, SO$_2$NHR$_9$, C(O)NR$_9$R$_9$, wherein R$_9$ is independently selected from C$_1$–C$_6$ alkyl or unsubstituted or substituted phenyl, —(C=NH)—NH$_2$, —(C=NH)—O-alkyl, methoxymethyl, or haloalkyl, wherein the substituents may be F, C$_l$, Br, I, OH, NH$_2$, SH, CN, NO$_2$, OCH$_3$, OC(O)CH$_3$, CF$_3$, OCH$_2$CH$_2$OH, NHC(O)CH$_3$, NHCH$_3$, or N(CH$_3$)$_2$;

—E—Y— is
—O—C(O)—NH—,
- - - denotes a single or double bond; and
* denotes cis or trans or a mixture thereof.

2. A compound according to claim 1 wherein:

X is independently selected from hydrogen and an electron withdrawing group selected from the group consisting of halogen, nitro, cyano, aminoalkyl CF$_3$, C(O)CH$_3$, and haloalkyl.

3. A compound of claim 1 wherein:

Ar is unsubstituted or substituted phenyl;

X is independently selected from hydrogen and an electron withdrawing group selected from the group consisting of halogen, nitro, cyano, aminoalkyl, CF$_3$, C(O)CH$_3$, and haloalkyl;

—E—Y— is

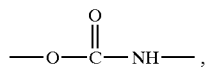

and
* denotes trans.

4. A compound according to claim 1 wherein;

Ar is unsubstituted or substituted phenyl;

Z is a group whereby Ar and the nitrogen atom in Formula I are separated by from 2 to 4 atoms;

X is independently selected from hydrogen and an electron withdrawing group selected from the group consisting of halogen, nitro, cyano, aminoalkyl, CF$_3$, C(O)CH$_3$, and haloalkyl;

—E—Y— is

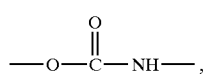

and
* denotes trans.

5. A compound according to claim 1 wherein:

Ar is unsubstituted or substituted phenyl;

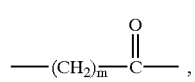

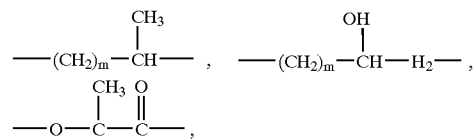

—C≡C—(CH$_2$)$_2$— wherein m is an integer 2 or 3;

R is hydrogen, H$_2$NC(O)alkyl, alkenylalkyl, methyl, heteroaralkyl, (C$_3$–C$_7$ cycloalkyl)alkyl, or C(O)CH$_3$;

—E—Y— is —O—C(O)—NH—;

X is hydrogen; and
* denotes trans.

6. A compound according to claim 1 selected from:

6-[trans-4-(3-Phenylpropylamino)cyclohexyl]-3H-benzoxazol-2-one;

6-{trans-4-[2-(4-Fluorophenoxy)ethylamino]cyclohexyl}-3H-benzoxazol-2-one;

6-[trans-4-(2-Phenoxyethylamino)cyclohexyl]-3H-benzoxazol-2-one;

6-{trans-4-[3-(4-Fluorophenyl)propylamino]cyclohexyl}-3H-benzoxazol-2-one;

6-{cis-4-[3-(4-Fluorophenyl)propylamino]cyclohexyl}-3H-benzoxazol-2-one;

6-[trans-4-(2-Phenylsulfanylethylamino)cyclohexyl]-3H-benzoxazol-2-one;

6-[cis-4-(2-Phenylsulfanylethylamino)cyclohexyl]-3H-benzoxazol-2-one;

6-[4-(3-Phenylpropylamino)cyclohex-1-enyl]-3H-benzoxazol-2-one;

6-{trans-4-[2-(4-Fluorophenylsulfanyl)ethylamino]cyclohexyl}-3H-benzoxazol-2-one;

6-{trans-4-[(R)-1-Methyl-3-phenylpropylamino]cyclohexyl}-3H-benzoxazol-2-one;

6-{trans-4-[(S)-1-Methyl-3-phenylpropylamino]cyclohexyl}-3H-benzoxazol-2-one;

6-{trans-4-[(1S,2S)-2-Hydroxy-2-(4-methoxyphenyl)-1-methylethylamino]cyclohexyl}-3H-benzoxazol-2-one;

6-{cis-4-[(1S,2S)-2-Hydroxy-2-(4-methoxyphenyl)-1-methylethylamino]-cyclohexyl}-3H-benzoxazol-2-one;

6-{trans-4-[(1S,2R)-2-Hydroxy-1-methyl-2-phenylethylamino]-cyclohexyl}-3H-benzoxazol-2-one;

6-[cis-4-(3-p-Tolylpropylamino)cyclohexyl]-3H-benzoxazol-2-one;

6-[trans-4-(3-p-Tolylpropylamino)cyclohexyl]-3H-benzoxazol-2-one;

6-[trans-4-(2-Benzenesulfinylethylamino)cyclohexyl]-3H-benzoxazol-2-one;

6-[trans-4-(2-Benzenesulfonylethylamino)cyclohexyl]-3H-benzoxazol-2-one;

6-{trans-4-[Methyl(3-phenylpropyl)amino]cyclohexyl}-3H-benzoxazol-2-one;

6-(trans-4-{[3-(4-Fluorophenyl)propyl]methylamino}cyclohexyl)-3H-benzoxazol-2-one;

6-(cis-4-{[3-(4-Fluorophenyl)propyl]methylamino}cyclohexyl)-3H-benzoxazol-2-one;

6-{trans-[4-(2-Methyl-3-phenylpropylamino)cyclohexyl]}-3H-benzoxazol-2-one;

6-{trans-4-[Methyl(2-methyl-3-phenylpropyl)amino]cyclohexyl}-3H-benzoxazol-2-one;
6-{trans-[4-(3-Phenyl-prop-2-ynylamino)cyclohexyl]}-3H-benzoxazol-2-one;
6-{trans-4-[Methyl(3-phenylprop-2-ynyl)amino]cyclohexyl}-3H-benzoxazol-2-one;
6-{trans-4-[2-(4-Fluorophenylsulfanylethyl)methylamino]cyclohexyl}-3H-benzoxazol-2-one;
6-{trans-4-[3-(4-Trifluoromethylphenyl)propylamino]cyclohexyl}-3H-benzoxazol-2-one;
6-{trans-4-[Methyl-3-(p-tolylpropyl)amino]cyclohexyl}-3H-benzoxazol-2-one;
6-{trans-4-[Methyl(2-phenoxyethyl)amino]cyclohexyl}-3H-benzoxazol-2-one;
6-{trans-4-[Methyl-3-(4-tifluoromethylphenyl)propylamino]cyclohexyl}-3H-benzoxazol-2-one;
6-{trans-4-[3-(2,4-Difluorophenyl)propylamino]cyclohexyl}-3H-benzoxazol-2-one;
6-(trans-4-{[3-(2,4-Difluorophenyl)propyl]methylamino}cyclohexyl)-3H-benzoxazol-2-one;
6-(trans-4-{[3-(4-Isopropylphenyl)propyl]methylamino}cyclohexyl)-3H-benzoxazol-2-one;
6-(trans-4-{[3-(4-Isobutylphenyl)propyl]methylamino}cyclohexyl)-3H-benzoxazol-2-one;
6-(trans-4-{[Ethyl-[3-(4-fluorophenyl)propyl]amino}cyclohexyl)-3H-benzoxazol-2-one;
6-(trans-4-{Ethyl-[3-(4-trifluoromethylphenyl)propyl]amino}cyclohexyl)-3H-benzoxazol-2-one;
6-(trans-4-{Ethyl-[(R)-1-methyl-3-phenylpropyl]amino}cyclohexyl)-3H-benzoxazol-2-one;
6-(trans-4-{Ethyl-[(S)-1-methyl-3-phenylpropyl]amino}cyclohexyl)-3H-benzoxazol-2-one;
6-{trans-4-[[3-(4-Fluorophenyl)propyl]-(2-hydroxyethyl)amino]-yclohexyl}-3H-benzoxazol-2-one;
6-(trans-4-{Cyclopropylmethyl-[3-(4-fluorophenyl)propyl]amino}-cyclohexyl)-3H-benzoxazol-2-one;
6-(trans-4-{[3-(4-Fluorophenyl)propyl]furan-3-cylmethylamino}cyclohexyl)-3H-benzoxazol-2-one;
6-(trans-4-{Allyl-[3-(4-Fluorophenyl)propyl]amino}cyclohexyl)-3H-benzoxazol-2-one;
6-(trans-4-{[3-(4-Fluorophenyl)propyl]isobutylamino}cyclohexyl)-3H-benzoxazol-2-one;
6-(trans-4-{(2-Aminoethyl)-[3-(4-fluorophenyl)propyl]amino}-cyclohexyl)-3H-benzoxazol-2-one;
(S)-6-{trans-4-[1-(4-Fluorophenylsulfanyl)pentan-2-ylamino]cyclohexyl}3H-benzoxazol-2-one;
(S)-6-{trans-4-[Ethyl(1-(4-fluorophenylsulfanyl)pentan-2-yl)amino]-cyclohexyl}-3H-benzoxazol-2-one;
6-[trans-4-(3-Phenylbutylamino)cyclohexyl]-3H-benzoxazol-2-one;
6-[trans-4-(Methyl-3-phenylbutylamino)cyclohexyl]-3H-benzoxazol-2-one;
6-{trans-4-[3-(4-Chlorophenyl)propylamino]cyclohexyl}-3H-benzoxazol-2-one;
6-(trans-4-{[3-(4-Chlorophenyl)propyl]methylamino}cyclohexyl)-3H-benzoxazol-2-one;
6-(trans-4-{[3-(2,4-Dichlorophenyl)propyl]methylamino}cyclohexyl)-3H-benzoxazol-2-one;
6-(trans-4-[3-(3,5-Difluorophenyl)propylamino]cyclohexyl}-3H-benzoxazol-2-one;
6-(trans-4-{[3-(3,5-Difluorophenyl)propyl]methylamino}cyclohexyl)-3H-benzoxazol-2-one;
6-(trans-4-[3-(3,4-Difluorophenyl)propylamino]cyclohexyl}-3H-benzoxazol-2-one;
6-(trans-4-{[3-(3,4-Difluorophenyl)propyl]methylamino}cyclohexyl)-3H-benzoxazol-2-one;
6-(trans-4-{[3-(2,3,4-Trifluorophenyl)propyl]methylamino}cyclohexyl)-3H-benzoxazol-2-one;
6-(4-{[3-(trans-4-Dimethylaminophenyl)propyl]methylamino}-cyclohexyl)-3H-benzoxazol-2-one;
6-(trans-4-{[3-(2,4,6-Trifluorophenyl)propyl]methylamino}cyclohexyl)-3H-benzoxazol-2-one;
6-(trans-4-[3-(2,4-Dimethylphenyl)propylamino]cyclohexyl}-3H-benzoxazol-2-one;
6-(trans-{4-[Methyl(2,4-dimethylphenylpropyl)amino]cyclohexyl})-3H-benzoxazol-2-one;
6-{trans-4-[3-(2-Chloro-4-fluorophenyl)propylamino]cyclohexyl}-3H-benzoxazol-2-one;
6-(trans-4-{[3-(2-Chloro-4-fluorophenyl)propyl]methylamino}-cyclohexyl)-3H-benzoxazol-2-one;
6-{trans-4-[3-(4-Chloro-2-fluorophenyl)propylamino]cyclohexyl}-3H-benzoxazol-2-one;
6-(trans-4-{[3-(4-Chloro-2-fluorophenyl)propyl]methylamino}-cyclohexyl)-3H-benzoxazol-2-one;
6-(trans-4-[3-(4-Fluoro-2-methylphenyl)propylamino]cyclohexyl}-3H-benzoxazol-2-one;
6-(trans-{4-[Methyl(4-fluoro-2-methylphenylpropyl)amino]cyclohexyl})-3H-benzoxazol-2-one;
6-{trans-4-[3-(3-Fluoro-2-methylphenyl)propylamino]cyclohexyl}-3H-benzoxazol-2-one;
6-(trans-4-{[3-(3-Fluoro-2-methylphenyl)propyl]methylamino}-cyclohexyl)-3H-benzoxazol-2-one;
6-{trans-4-[3-(2-Fluorophenyl)propylamino]cyclohexyl}-3H-benzoxazol-2-one;
6-(trans-4-{[3-(2-Fluorophenyl)propyl]methylamino}cyclohexyl)-3H-benzoxazol-2-one;
6-{trans-4-[3-(3-Fluorophenyl)propylamino]cyclohexyl}-3H-benzoxazol-2-one;
6-(trans-4-{[3-(3-Fluorophenyl)propyl]methylamino}cyclohexyl)-3H-benzoxazol-2-one;
6-{trans-4-[(3-Cyclohexylpropyl)amino]cyclohexyl}-3H-benzoxazol-2-one;
6-{trans-4-[(3-Cyclohexylpropyl)methylamino]cyclohexyl}-3H-benzoxazol-2-one;
6-{trans-4-[4-(3-Thiophen-3-yl)propylamino]cyclohexyl}-3H-benzoxazol-2-one;
6-[trans-4-{[3-(3-Thiophen-3-yl)propyl]methylamino}cyclohexyl)-3H-benzoxazol-2-one;
6-{trans-4-[Methyl(3-thiazol-2-ylpropyl)amino]cyclohexyl}-3H-benzoxazol-2-one;
6-(trans-4-{Methyl-[2-(methylphenylamino)ethyl]amino}cyclohexyl)-3H-benzoxazol-2-one;
6-(4-{[3-(4-Fluorophenyl)propyl]methylamino}cyclohexyl)-5-methyl-3H-benzoxazol-2-one; and
6-(trans-4-{[3-(4-Fluorophenyl)propyl]methylamino}cyclohexyl)-5-methoxy-3H-benzoxazol-2-one.

7. A pharmaceutical composition useful for treating disorders responsive to the selective blockade of N-methyl-D-aspartate receptor subtypes selected from the group consisting of stroke, cerebral ischemia, trauma, hypoglycemia, Parkinson's disease, anxiety, depression, migraine headache, convulsions, aminoglycoside antibiotics-induced hearing loss, psychosis, glaucoma, CMV retinitis, opioid tolerance or withdrawal, chronic pain and urinary incontinence the compositions comprising a pharmaceutically acceptable carrier or diluent and a therapeutically effective amount of at least one compound of claim 1 or claim 3.

8. A pharmaceutical composition according to claim 7 wherein the disorder is Parkinson's disease.

9. A pharmaceutical composition according to claim 7, further comprising a dopamine agonist or precursor thereof in amount effective to treat Parkinson's disease.

10. A method for treating disorders responsive to the selective blockade of N-methyl-D-aspartate receptor subtypes selected from the group consisting of stroke, cerebral ischemia, trauma, hypoglycemia, Parkinson's disease, anxiety, depression, migraine headache, convulsions, aminoglycoside antibiotics-induced hearing loss, psychosis, glaucoma, CMV retinitis, opioid tolerance or withdrawal, chronic pain and urinary incontinence in a mammal suffering thereof which comprises administering in unit dosage form at least one compound represented by Formula I of claim 1.

11. A method according to claim 10, wherein the disorder is Parkinson's disease.

12. A method according to claim 10, further comprising administering in unit dosage form a compound of Formula I to a mammal suffering from Parkinson's disease.

* * * * *